United States Patent
Takahashi et al.

(10) Patent No.: US 8,710,022 B2
(45) Date of Patent: Apr. 29, 2014

(54) CELL PROLIFERATION INHIBITOR

(75) Inventors: Takashi Takahashi, Aichi (JP); Tomoya Yamaguchi, Aichi (JP); Shuta Tomida, Aichi (JP)

(73) Assignee: National University Corporation Nagoya University, Aichi (JP)

( * ) Notice: Subject to any disclaimer, the term of this patent is extended or adjusted under 35 U.S.C. 154(b) by 75 days.

(21) Appl. No.: 13/054,288

(22) PCT Filed: Jul. 17, 2009

(86) PCT No.: PCT/JP2009/062975
§ 371 (c)(1),
(2), (4) Date: Dec. 14, 2011

(87) PCT Pub. No.: WO2010/008069
PCT Pub. Date: Jan. 21, 2010

(65) Prior Publication Data
US 2012/0082986 A1    Apr. 5, 2012

(30) Foreign Application Priority Data
Jul. 18, 2008  (JP) ................................. 2008-187857

(51) Int. Cl.
C12N 15/113    (2010.01)
(52) U.S. Cl.
USPC ....................................................... 514/44 A
(58) Field of Classification Search
None
See application file for complete search history.

(56) References Cited

FOREIGN PATENT DOCUMENTS

| WO | 2004/045543 A2 | 6/2004 |
|---|---|---|
| WO | 2005/100605 A1 | 10/2005 |
| WO | 2007/051077 A2 | 5/2007 |
| WO | 2007/146957 A2 | 12/2007 |

OTHER PUBLICATIONS

MacKeigan, Jeffrey P. et al., "Sensitized RNAi screen of human kinases adn phosphatases identifies new regulators of apoptosis and chemoresistance," Nature Cell Biology, vol. 7(6):591-600 (2005).
Tanaka, Hisaaki et al., "Lineage-Specific Dependency of Lung Adenocarcinomas on the Lung Development Regulator TTF-1," Cancer Res., vol. 67(13):6007-6011 (2007).
Fukuda, Tetsuya et al., "Antisera induced by infusions of autologous Ad-CD154-leukemia B cells identify ROR1 as an oncofetal antigen and receptor for Wnt5a," PNAS, vol. 105(8):3047-3052 (2008).
Masiakowski, Piotr et al., "A Novel Family of Cell Surface Receptors with Tyrosine Kinase-like Domain," The Journal of Biological Chemistry, vol. 267(36):26181-26190 (1992).
Paganoni, Sabrina et al., "Neurite extension in central neurons: a novel role for the receptor tyrosine kinases Ror1 and Ror2," J. Cell Sci., vol. 118(Pt. 2):433-446 (2005).
International Search Report for Application No. PCT/JP2009/062975, 7 pages, dated Oct. 27, 2009.
International Preliminary Report on Patentability for Application No. PCT/JP2009/062975, 6 pages, dated Jan. 18, 2011.
Supplementary European Search Report for Application No. 09797993.4, 6 pages, dated Mar. 6, 2013.

*Primary Examiner* — Tracy Vivlemore
(74) *Attorney, Agent, or Firm* — Nelson Mullins Riley & Scarborough LLP; Jeanne M. DiGiorgio

(57) ABSTRACT

The present inventors revealed a TTF-1-specific oncogenic process by elucidating the molecular mechanism regulated by the master regulatory factor TTF-1. The present inventors focused on the elucidation of the essence of the lineage-specific survival signal which is a novel canceration signal. Thus, the present inventors found that the expression of ROR1, which is a receptor tyrosine kinase, is induced by the master regulatory factor TTF-1, and demonstrated the presence of a characteristic canceration signal transduction system.

6 Claims, 19 Drawing Sheets

SEQUENCE LISTING

<160> NUMBER OF SEQ ID NOS: 471

<210> SEQ ID NO 1
<211> LENGTH: 3382
<212> TYPE: DNA
<213> ORGANISM: Homo sapiens

<400> SEQUENCE: 1

```
gttgagcgag agagggagcg tggagagctg gagcagccgc caccgccgcc gccgagggag      60
ccccgggacg gcagcccctg ggcgcagggt gcgctgttct cggagtccga cccagggcga     120
ctcacgccca ctggtgcgac ccggacagcc tgggactgac ccgccggccc aggcgaggct     180
gcagccagag ggctgggaag ggatcgcgct cgcggcatcc agaggcggcc aggcggaggc     240
gagggagcag gttagaggga caaagagctt tgcagacgtc cccggcgtcc tgcgagcgcc     300
agcggccggg acgaggcggc cgggagcccg ggaagagccc gtggatgttc tgcgcgcggc     360
ctgggagccg ccgccgccgc cgcctcagcg agaggaggaa tgcaccggcc gcgccgccgc     420
gggacgcgcc cgccgctcct ggcgctgctg gccgcgctgc tgctggccgc acgcggggct     480
gctgcccaag aaacagagct gtcagtcagt gctgaattag tgcctacctc atcatggaac     540
atctcaagtg aactcaacaa agattcttac ctgaccctcg atgaaccaat gaataacatc     600
accacgtctc tgggccagac agcagaactg cactgcaaag tctctgggaa tccacctccc     660
accatccgct ggttcaaaaa tgatgctcct gtggtccagg agcccggag gctctccttt     720 cggtccacca tctatggctc tcggctgcgg attagaaacc tcgacaccac agacacaggc     780
tacttccagt gcgtggcaac aaacggcaag gaggtggttt cttccactgg agtcttgttt     840
gtcaagtttg gccccctcc cactgcaagt ccaggatact cagatgagta tgaagaagat     900
ggattctgtc agccatacag agggattgca tgtgcaagat ttattggcaa ccgcaccgtc     960
tatatggagt ctttgcacat gcaagggaa atagaaaatc agatcacagc tgccttcact    1020
atgattggca cttccagtca cttatctgat aagtgttctc agttcgccat tccttccctg    1080
tgccactatg ccttcccgta ctgcgatgaa acttcatccg tcccaaagcc ccgtgacttg    1140
tgtcgcgatg aatgtgaaat cctggagaat gtcctgtgtc aaacagagta cattttgca    1200 agatcaaatc ccatgattct gatgaggctg aaactgccaa actgtgaaga tctcccccag    1260
```

-continued

```
ccagagagcc cagaagctgc gaactgtatc cggattggaa ttcccatggc agatcctata    1320
aataaaaatc acaagtgtta taacagcaca ggtgtggact accggggggac cgtcagtgtg    1380
accaaatcag ggcgccagtg ccagccatgg aattcccagt atccccacac acacactttc    1440
accgcccttc gtttcccaga gctgaatgga ggccattcct actgccgcaa cccagggaat    1500
caaaaggaag ctccctggtg cttcaccttg gatgaaaact ttaagtctga tctgtgtgac    1560
atcccagcgt gcgattcaaa ggattccaag gagaagaata aaatggaaat cctgtacata    1620
ctagtgccaa gtgtggccat tccctggcc attgctttac tcttcttctt catttgcgtc    1680
tgtcggaata accagaagtc atcgtcggca ccagtccaga ggcaaccaaa acacgtcaga    1740
ggtcaaaatg tagagatgtc aatgctgaat gcatataaac ccaagagcaa ggctaaagag    1800
ctacctcttt ctgctgtacg ctttatggaa gaattgggtg agtgtgcctt tggaaaaatc    1860
tataaaggcc atctctatct cccaggcatg gaccatgctc agctggttgc tatcaagacc    1920
ttgaaagact ataacaaccc ccagcaatgg acggaatttc aacaagaagc ctccctaatg    1980
gcagaactgc accaccccaa tattgtctgc cttctaggtg ccgtcactca ggaacaacct    2040
gtgtgcatgc ttttgagta tattaatcag ggggatctcc atgagttcct catcatgaga    2100
tccccacact ctgatgttgg ctgcagcagt gatgaagatg ggactgtgaa atccagcctg    2160
gaccacggag attttctgca cattgcaatt cagattgcag ctggcatgga ataccttgtct    2220
agtcacttct ttgtccacaa ggaccttgca gctcgcaata ttttaatcgg agagcaactt    2280
catgtaaaga tttcagactt ggggctttcc agagaaattt actccgctga ttactacagg    2340
gtccagagta agtccttgct gcccattcgc tggatgcccc ctgaagccat catgtatggc    2400
aaattctctt ctgattcaga tatctggtcc tttggggttg tcttgtggga gattttcagt    2460
tttggactcc agccatatta tggattcagt aaccaggaag tgattgagat ggtgagaaaa    2520
cggcagctct taccatgctc tgaagactgc ccacccagaa tgtacagcct catgacagag    2580
tgctggaatg agattccttc taggagacca agatttaaag atattcacgt ccggcttcgg    2640
tcctgggagg gactctcaag tcacacaagc tctactactc cttcaggggg aaatgccacc    2700
acacagacaa cctccctcag tgccagccca gtgagtaatc tcagtaaccc cagatatcct    2760
aattacatgt tcccgagcca gggtattaca ccacagggcc agattgctgg tttcattggc    2820
ccgccaatac ctcagaacca gcgattcatt cccatcaatg gataccccaat acctcctgga    2880
tatgcagcgt ttccagctgc ccactaccag ccaacaggtc ctcccagagt gattcagcac    2940
tgcccacctc ccaagagtcg gtccccaagc agtgccagtg ggtcgactag cactggccat    3000
gtgactagct tgccctcatc aggatccaat caggaagcaa atattccttt actaccacac    3060
atgtcaattc caaatcatcc tggtggaatg ggtatcaccg tttttggcaa caaatctcaa    3120
aaaccctaca aaattgactc aaagcaagca tctttactag gagacgccaa tattcatgga    3180
cacaccgaat ctatgatttc tgcagaactg taaaatgcac aacttttgta aatgtggtat    3240
acaggacaaa ctagacggcc gtagaaaaga tttatattca aatgttttta ttaaagtaag    3300
gttctcattt agcagacatc gcaacaagta ccttctgtga agtttcactg tgtcttacca    3360
agcaggacag acactcggcc ag                                              3382
```

<210> SEQ ID NO 2
<211> LENGTH: 937
<212> TYPE: PRT
<213> ORGANISM: Homosapiens

<400> SEQUENCE: 2

```
Met His Arg Pro Arg Arg Arg Gly Thr Arg Pro Leu Leu Ala Leu
1               5                   10                  15

Leu Ala Ala Leu Leu Ala Ala Arg Gly Ala Ala Gln Glu Thr
            20                  25                  30

Glu Leu Ser Val Ser Ala Glu Leu Val Pro Thr Ser Ser Trp Asn Ile
        35                  40                  45

Ser Ser Glu Leu Asn Lys Asp Ser Tyr Leu Thr Leu Asp Glu Pro Met
50                  55                  60

Asn Asn Ile Thr Thr Ser Leu Gly Gln Thr Ala Glu Leu His Cys Lys
65                  70                  75                  80

Val Ser Gly Asn Pro Pro Thr Ile Arg Trp Phe Lys Asn Asp Ala
                85                  90                  95

Pro Val Val Gln Glu Pro Arg Arg Leu Ser Phe Arg Ser Thr Ile Tyr
            100                 105                 110

Gly Ser Arg Leu Arg Ile Arg Asn Leu Asp Thr Thr Asp Thr Gly Tyr
        115                 120                 125

Phe Gln Cys Val Ala Thr Asn Gly Lys Glu Val Val Ser Ser Thr Gly
    130                 135                 140

Val Leu Phe Val Lys Phe Gly Pro Pro Thr Ala Ser Pro Gly Tyr
145                 150                 155                 160

Ser Asp Glu Tyr Glu Glu Asp Gly Phe Cys Gln Pro Tyr Arg Gly Ile
                165                 170                 175

Ala Cys Ala Arg Phe Ile Gly Asn Arg Thr Val Tyr Met Glu Ser Leu
            180                 185                 190

His Met Gln Gly Glu Ile Glu Asn Gln Ile Thr Ala Ala Phe Thr Met
        195                 200                 205

Ile Gly Thr Ser Ser His Leu Ser Asp Lys Cys Ser Gln Phe Ala Ile
    210                 215                 220

Pro Ser Leu Cys His Tyr Ala Phe Pro Tyr Cys Asp Glu Thr Ser Ser
225                 230                 235                 240

Val Pro Lys Pro Arg Asp Leu Cys Arg Asp Glu Cys Glu Ile Leu Glu
                245                 250                 255

Asn Val Leu Cys Gln Thr Glu Tyr Ile Phe Ala Arg Ser Asn Pro Met
            260                 265                 270

Ile Leu Met Arg Leu Lys Leu Pro Asn Cys Glu Asp Leu Pro Gln Pro
        275                 280                 285

Glu Ser Pro Glu Ala Ala Asn Cys Ile Arg Ile Gly Ile Pro Met Ala
    290                 295                 300

Asp Pro Ile Asn Lys Asn His Lys Cys Tyr Asn Ser Thr Gly Val Asp
305                 310                 315                 320

Tyr Arg Gly Thr Val Ser Val Thr Lys Ser Gly Arg Gln Cys Gln Pro
                325                 330                 335

Trp Asn Ser Gln Tyr Pro His Thr His Thr Phe Thr Ala Leu Arg Phe
            340                 345                 350

Pro Glu Leu Asn Gly Gly His Ser Tyr Cys Arg Asn Pro Gly Asn Gln
        355                 360                 365

Lys Glu Ala Pro Trp Cys Phe Thr Leu Asp Glu Asn Phe Lys Ser Asp
    370                 375                 380

Leu Cys Asp Ile Pro Ala Cys Asp Ser Lys Asp Ser Lys Glu Lys Asn
385                 390                 395                 400

Lys Met Glu Ile Leu Tyr Ile Leu Val Pro Ser Val Ala Ile Pro Leu
                405                 410                 415

Ala Ile Ala Leu Leu Phe Phe Ile Cys Val Cys Arg Asn Asn Gln
            420                 425                 430
```

```
Lys Ser Ser Ser Ala Pro Val Gln Arg Gln Pro Lys His Val Arg Gly
        435                 440                 445

Gln Asn Val Glu Met Ser Met Leu Asn Ala Tyr Lys Pro Lys Ser Lys
    450                 455                 460

Ala Lys Glu Leu Pro Leu Ser Ala Val Arg Phe Met Glu Glu Leu Gly
465                 470                 475                 480

Glu Cys Ala Phe Gly Lys Ile Tyr Lys Gly His Leu Tyr Leu Pro Gly
                485                 490                 495

Met Asp His Ala Gln Leu Val Ala Ile Lys Thr Leu Lys Asp Tyr Asn
            500                 505                 510

Asn Pro Gln Gln Trp Thr Glu Phe Gln Gln Glu Ala Ser Leu Met Ala
        515                 520                 525

Glu Leu His His Pro Asn Ile Val Cys Leu Leu Gly Ala Val Thr Gln
        530                 535                 540

Glu Gln Pro Val Cys Met Leu Phe Glu Tyr Ile Asn Gln Gly Asp Leu
545                 550                 555                 560

His Glu Phe Leu Ile Met Arg Ser Pro His Ser Asp Val Gly Cys Ser
                565                 570                 575

Ser Asp Glu Asp Gly Thr Val Lys Ser Ser Leu Asp His Gly Asp Phe
            580                 585                 590

Leu His Ile Ala Ile Gln Ile Ala Ala Gly Met Glu Tyr Leu Ser Ser
        595                 600                 605

His Phe Phe Val His Lys Asp Leu Ala Ala Arg Asn Ile Leu Ile Gly
        610                 615                 620

Glu Gln Leu His Val Lys Ile Ser Asp Leu Gly Leu Ser Arg Glu Ile
625                 630                 635                 640

Tyr Ser Ala Asp Tyr Tyr Arg Val Gln Ser Lys Ser Leu Leu Pro Ile
                645                 650                 655

Arg Trp Met Pro Pro Glu Ala Ile Met Tyr Gly Lys Phe Ser Ser Asp
            660                 665                 670

Ser Asp Ile Trp Ser Phe Gly Val Val Leu Trp Glu Ile Phe Ser Phe
        675                 680                 685

Gly Leu Gln Pro Tyr Tyr Gly Phe Ser Asn Gln Glu Val Ile Glu Met
        690                 695                 700

Val Arg Lys Arg Gln Leu Leu Pro Cys Ser Glu Asp Cys Pro Pro Arg
705                 710                 715                 720

Met Tyr Ser Leu Met Thr Glu Cys Trp Asn Glu Ile Pro Ser Arg Arg
                725                 730                 735

Pro Arg Phe Lys Asp Ile His Val Arg Leu Arg Ser Trp Glu Gly Leu
            740                 745                 750

Ser Ser His Thr Ser Ser Thr Thr Pro Ser Gly Gly Asn Ala Thr Thr
        755                 760                 765

Gln Thr Thr Ser Leu Ser Ala Ser Pro Val Ser Asn Leu Ser Asn Pro
        770                 775                 780

Arg Tyr Pro Asn Tyr Met Phe Pro Ser Gln Gly Ile Thr Pro Gln Gly
785                 790                 795                 800

Gln Ile Ala Gly Phe Ile Gly Pro Pro Ile Pro Gln Asn Gln Arg Phe
                805                 810                 815

Ile Pro Ile Asn Gly Tyr Pro Ile Pro Pro Gly Tyr Ala Ala Phe Pro
            820                 825                 830

Ala Ala His Tyr Gln Pro Thr Gly Pro Pro Arg Val Ile Gln His Cys
        835                 840                 845

Pro Pro Pro Lys Ser Arg Ser Pro Ser Ser Ala Ser Gly Ser Thr Ser
```

|     |     |     |     |     |     |     |     |     |     |     |     |     |     |
| --- | --- | --- | --- | --- | --- | --- | --- | --- | --- | --- | --- | --- | --- |
|     | 850 |     |     |     | 855 |     |     |     | 860 |     |     |     |     |
| Thr | Gly | His | Val | Thr | Ser | Leu | Pro | Ser | Ser | Gly | Ser | Asn | Gln | Glu | Ala |
| 865 |     |     |     |     | 870 |     |     |     | 875 |     |     |     |     | 880 |

Asn Ile Pro Leu Leu Pro His Met Ser Ile Pro Asn His Pro Gly Gly
            885                 890                 895

Met Gly Ile Thr Val Phe Gly Asn Lys Ser Gln Lys Pro Tyr Lys Ile
                900                 905                 910

Asp Ser Lys Gln Ala Ser Leu Leu Gly Asp Ala Asn Ile His Gly His
            915                 920                 925

Thr Glu Ser Met Ile Ser Ala Glu Leu
    930                 935

<210> SEQ ID NO 3
<211> LENGTH: 4382
<212> TYPE: DNA
<213> ORGANISM: Homo sapiens

<400> SEQUENCE: 3

```
acaaggcaaa caggaggtat ttagtaagtg gccacgtgat tattgagaga ctatgggctt      60
cttcctgttc ctccagagca agactgacag gtgtcctatt acccttgcat cttcagagcc     120
tagagcacag ccctgaaaac agcaggcgct caccactttt tatgatcaaa ggcagtctct     180
acagggaaag tcaaatcatt atgggtattt atgaattaca aaatccataa agttaaacca     240
ggagaaatgg acaaaaacac actcattgta gaggtcttta atgatccctt ggctcatggc     300
agagcagcta gacaaaaaac aaacaaacaa acaaacatgc aaagattcag aaggcctgaa     360
aaataatga atacaaagaa gataaatcga tacagtattc tatcttcaca ttcggaagac     420
aaaaacaccct ttcaaaaaac catgggacat tggcaaaaat aaccacagat aatcctcaat     480
aaatcttgcc aggaggcagt acagatgaca ttgaattcag tgagactaca aattaaagac     540
aaaaaggcga agtataaatt acttgtgtaa gaactctctc aactcttggg tccaagaaga     600
aagcaaaagg gaaattgtat gatagcaata atgtgccat tacccagagt cacacagcta      660
acagtgacac agctgaggct gctagaacct gggtctactg tcgtccagcc acgaactggc     720
ttgagatccc ggataagtct ctctgagcct cggtttcccc ttctgtcaag tagcctcgaa     780
ggtccccggc gctcggttcg gtggcgagtt tgaggagtgt gggggagggg agggagggga     840
gcgtgcccga gacgcgggag ccgcgaccgc tttctgcgaa gtcggggagg gtgcgggcgt     900
tgagaggctg cagcagaggg cgctgggtcg ccagcctggg ccgcgtctcc cattggtcgg     960
ggctggggcg ctgggctgga gagttggtgg aaagtgacaa gttgagcgag agaggagcg    1020
tggagagctg gagcagccgc caccgccgcc gccgagggag ccccgggacg gcagcccctg    1080
ggcgcagggt gcgctgttct cggagtccga cccagggcga ctcacgccca ctggtgcgac    1140
ccggacagcc tgggactgac ccgccggcc aggcgaggct gcagccagag ggctgggaag    1200
ggatcgcgct cgcggcatcc agaggcggcc aggcggaggc gagggagcag gttagaggga    1260
caaagagctt tgcagacgtc cccggcgtcc tgcgagcgcc agcggccggg acgaggcggc    1320
cgggagcccg ggaagagccc gtggatgttc tgcgcgcggc ctgggagccg ccgccgccgc    1380
cgcctcagcg agaggaggaa tgcaccggcc gcgccgccgc gggacgcgcc cgccgctcct    1440
ggcgctgctg gccgcgctgc tgctggccgc acgcggggct gctgcccaag aaacagagct    1500
gtcagtcagt gctgaattag tgcctaccct atcatggaac atctcaagtg aactcaacaa    1560
agattcttac ctgaccctcg atgaaccaat gaataacatc accacgtctc tgggccagac    1620
agcagaactg cactgcaaag tctctgggaa tccacctccc accatccgct ggttcaaaaa    1680
```

```
tgatgctcct gtggtccagg agccccggag gctctccttt cggtccacca tctatggctc    1740
tcggctgcgg attagaaacc tcgacaccac agacacaggc tacttccagt gcgtggcaac    1800
aaacggcaag gaggtggttt cttccactgg agtcttgttt gtcaagtttg ccccccctcc    1860
cactgcaagt ccaggatact cagatgagta tgaagaagat ggattctgtc agccatacag    1920
agggattgca tgtgcaagat ttattggcaa ccgcaccgtc tatatggagt ctttgcacat    1980
gcaaggggaa atagaaaatc agatcacagc tgccttcact atgattggca cttccagtca    2040
cttatctgat aagtgttctc agttcgccat tccttccctg tgccactatg ccttcccgta    2100
ctgcgatgaa acttcatccg tcccaaagcc ccgtgacttg tgtcgcgatg aatgtgaaat    2160
cctggagaat gtcctgtgtc aaacagagta cattttttgca agatcaaatc ccatgattct    2220
gatgaggctg aaactgccaa actgtgaaga tctcccccag ccagagagcc cagaagctgc    2280
gaactgtatc cggattggaa ttcccatggc agatcctata aataaaaatc acaagtgtta    2340
taacagcaca ggtgtggact accgggggac cgtcagtgtg accaaatcag ggcgccagtg    2400
ccagccatgg aattcccagt atccccacac acacactttc accgcccttc gtttcccaga    2460
gctgaatgga ggccattcct actgccgcaa cccagggaat caaaaggaag ctccctggtg    2520
cttcaccttg gatgaaaact ttaagtctga tctgtgtgac atcccagcgt gcgattcaaa    2580
ggattccaag gagaagaata aaatggaaat cctgtacata ctagtgccaa gtgtggccat    2640
tcccctggcc attgctttac tcttcttctt catttgcgtc tgtcggaata ccagaagtc     2700
atcgtcggca ccagtccaga ggcaaccaaa acacgtcaga ggtcaaaatg tagagatgtc    2760
aatgctgaat gcatataaac ccaagagcaa ggctaaagag ctacctcttt ctgctgtacg    2820
ctttatggaa gaattgggtg agtgtgcctt tggaaaaatc tataaaggcc atctctatct    2880
cccaggcatg gaccatgctc agctggttgc tatcaagacc ttgaaagact ataacaaccc    2940
ccagcaatgg acggaatttc aacaagaagc tccctaatg gcagaactgc accaccccaa     3000
tattgtctgc cttctaggtg ccgtcactca ggaacaacct gtgtgcatgc tttttgagta    3060
tattaatcag ggggatctcc atgagttcct catcatgaga tccccacact ctgatgttgg    3120
ctgcagcagt gatgaagatg ggactgtgaa atccagcctg gaccacggag attttctgca    3180
cattgcaatt cagattgcag ctggcatgga atacctgtct agtcacttct tgtccacaa     3240
ggaccttgca gctcgcaata tttaatcgg agagcaactt catgtaaaga tttcagactt     3300
ggggctttcc agagaaattt actccgctga ttactacagg gtccagagta agtccttgct    3360
gcccattcgc tggatgcccc ctgaagccat catgtatggc aaattctctt ctgattcaga    3420
tatctggtcc tttggggttg tcttgtggga gattttcagt tttggactcc agccatatta    3480
tggattcagt aaccaggaag tgattgagat ggtgagaaaa cggcagctct taccatgctc    3540
tgaagactgc cacccagaa tgtacagcct catgacagag tgctggaatg agattccttc     3600
taggagacca agatttaaag atattcacgt ccggcttcgg tcctgggagg gactctcaag    3660
tcacacaagc tctactactc cttcagggg aaatgccacc acacagacaa cctcccttcag    3720
tgccagccca gtgagtaatc tcagtaaccc cagatatcct aattacatgt tcccgagcca    3780
gggtattaca ccacagggcc agattgctgg tttcattggc ccgccaatac ctcagaacca    3840
gcgattcatt cccatcaatg gatacccaat acctcctgga tatgcagcgt ttccagctgc    3900
ccactaccag ccaacaggtc tcccagagt gattcagcac tgcccacctc caagagtcg     3960
gtccccaagc agtgccagtg gtcgactag cactggccat gtgactagct tgccctcatc    4020
aggatccaat caggaagcaa atattccttt actaccacac atgtcaattc caaatcatcc    4080
```

```
tggtggaatg ggtatcaccg tttttggcaa caaatctcaa aaaccctaca aaattgactc    4140
aaagcaagca tctttactag gagacgccaa tattcatgga cacaccgaat ctatgatttc    4200
tgcagaactg taaaatgcac aacttttgta aatgtggtat acaggacaaa ctagacggcc    4260
gtagaaaaga tttatattca aatgttttta ttaaagtaag gttctcattt agcagacatc    4320
gcaacaagta ccttctgtga agtttcactg tgtcttacca agcaggacag acactcggcc    4380
ag                                                                   4382

<210> SEQ ID NO 4
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 4
gattgcatgt gcaagattt                                                 19

<210> SEQ ID NO 5
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 5
cccagtgagt aatctcagt                                                 19

<210> SEQ ID NO 6
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 6
cccagaagct gcgaactgt                                                 19

<210> SEQ ID NO 7
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 7
gccagtgcca gccatggaa                                                 19

<210> SEQ ID NO 8
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 8
ctgtgtcaaa cagagtaca                                                 19

<210> SEQ ID NO 9
```

-continued

```
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 9
gaccgtcagt gtgaccaaa                                                   19

<210> SEQ ID NO 10
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 10
catggcagat cctataaat                                                   19

<210> SEQ ID NO 11
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 11
gtcagtcagt gctgaatta                                                   19

<210> SEQ ID NO 12
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 12
gacggaattt caacaagaa                                                   19

<210> SEQ ID NO 13
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 13
gagagcaact tcatgtaaa                                                   19

<210> SEQ ID NO 14
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 14
tggagaatgt cctgtgtca                                                   19

<210> SEQ ID NO 15
<211> LENGTH: 19
<212> TYPE: DNA
```

```
<213> ORGANISM: Artificial
<220> FEATURE:
<223> OTHER INFORMATION: An artificially synthesized target sequence for
      siRNA

<400> SEQUENCE: 15
caaattctct tctgattca                                                   19

<210> SEQ ID NO 16
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 16
gagggactct caagtcaca                                                   19

<210> SEQ ID NO 17
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 17
ctcccagagt gattcagca                                                   19

<210> SEQ ID NO 18
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 18
gtgcctacct catcatgga                                                   19

<210> SEQ ID NO 19
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 19
gctttactct tcttcttca                                                   19

<210> SEQ ID NO 20
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 20
tccagtcact tatctgata                                                   19

<210> SEQ ID NO 21
<211> LENGTH: 19
<212> TYPE: DNA
<213> ORGANISM: Artificial
<220> FEATURE:
```

<223> OTHER INFORMATION: An artificially synthesized target sequence for
      siRNA

<400> SEQUENCE: 21
ccgtctatat ggagtcttt                                                   19

<210> SEQ ID NO 22
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 22
cccaccatcc gctggttca                                                   19

<210> SEQ ID NO 23
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 23
gccactatgc cttcccgta                                                   19

<210> SEQ ID NO 24
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 24
cccaatacct cctggatat                                                   19

<210> SEQ ID NO 25
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 25
gtgtcgcgat gaatgtgaa                                                   19

<210> SEQ ID NO 26
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 26
tcacttatct gataagtgt                                                   19

<210> SEQ ID NO 27
<211> LENGTH: 19
<212> TYPE: DNA
<213> ORGANISM: Artificial
<220> FEATURE:
<223> OTHER INFORMATION: An artificially synthesized target sequence for
      siRNA

```
<400> SEQUENCE: 27
cccatcaatg gatacccaa                                                19

<210> SEQ ID NO 28
<211> LENGTH: 19
<212> TYPE: DNA
<213> ORGANISM: Artificial
<220> FEATURE:
<223> OTHER INFORMATION: An artificially synthesized target sequence for
     siRNA

<400> SEQUENCE: 28
cagtgagtaa tctcagtaa                                                19

<210> SEQ ID NO 29
<211> LENGTH: 19
<212> TYPE: DNA
<213> ORGANISM: Artificial
<220> FEATURE:
<223> OTHER INFORMATION: An artificially synthesized target sequence for
     siRNA

<400> SEQUENCE: 29
catataaacc caagagcaa                                                19

<210> SEQ ID NO 30
<211> LENGTH: 19
<212> TYPE: DNA
<213> ORGANISM: Artificial
<220> FEATURE:
<223> OTHER INFORMATION: An artificially synthesized target sequence for
     siRNA

<400> SEQUENCE: 30
tccagtgcgt ggcaacaaa                                                19

<210> SEQ ID NO 31
<211> LENGTH: 19
<212> TYPE: DNA
<213> ORGANISM: Artificial
<220> FEATURE:
<223> OTHER INFORMATION: An artificially synthesized target sequence for
     siRNA

<400> SEQUENCE: 31
cccagaatgt acagcctca                                                19

<210> SEQ ID NO 32
<211> LENGTH: 19
<212> TYPE: DNA
<213> ORGANISM: Artificial
<220> FEATURE:
<223> OTHER INFORMATION: An artificially synthesized target sequence for
     siRNA

<400> SEQUENCE: 32
gggtgagtgt gcctttgga                                                19

<210> SEQ ID NO 33
<211> LENGTH: 19
<212> TYPE: DNA
<213> ORGANISM: Artificial
<220> FEATURE:
<223> OTHER INFORMATION: An artificially synthesized target sequence for
     siRNA

<400> SEQUENCE: 33
```

```
caagtgaact caacaaaga                                              19

<210> SEQ ID NO 34
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 34
ctcggctgcg gattagaaa                                              19

<210> SEQ ID NO 35
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 35
caaagtctct gggaatcca                                              19

<210> SEQ ID NO 36
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 36
cacaccgaat ctatgattt                                              19

<210> SEQ ID NO 37
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 37
gcgtctgtcg gaataacca                                              19

<210> SEQ ID NO 38
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 38
catattatgg attcagtaa                                              19

<210> SEQ ID NO 39
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 39
ctggccatgt gactagctt                                              19
```

<210> SEQ ID NO 40
<211> LENGTH: 19
<212> TYPE: DNA
<213> ORGANISM: Artificial
<220> FEATURE:
<223> OTHER INFORMATION: An artificially synthesized target sequence for siRNA

<400> SEQUENCE: 40
cggaggctct cctttcggt                                                  19

<210> SEQ ID NO 41
<211> LENGTH: 19
<212> TYPE: DNA
<213> ORGANISM: Artificial
<220> FEATURE:
<223> OTHER INFORMATION: An artificially synthesized target sequence for siRNA

<400> SEQUENCE: 41
cagagggatt gcatgtgca                                                  19

<210> SEQ ID NO 42
<211> LENGTH: 19
<212> TYPE: DNA
<213> ORGANISM: Artificial
<220> FEATURE:
<223> OTHER INFORMATION: An artificially synthesized target sequence for siRNA

<400> SEQUENCE: 42
tcctggatat gcagcgttt                                                  19

<210> SEQ ID NO 43
<211> LENGTH: 19
<212> TYPE: DNA
<213> ORGANISM: Artificial
<220> FEATURE:
<223> OTHER INFORMATION: An artificially synthesized target sequence for siRNA

<400> SEQUENCE: 43
gcgtgcgatt caaaggatt                                                  19

<210> SEQ ID NO 44
<211> LENGTH: 19
<212> TYPE: DNA
<213> ORGANISM: Artificial
<220> FEATURE:
<223> OTHER INFORMATION: An artificially synthesized target sequence for siRNA

<400> SEQUENCE: 44
caaatcccat gattctgat                                                  19

<210> SEQ ID NO 45
<211> LENGTH: 19
<212> TYPE: DNA
<213> ORGANISM: Artificial
<220> FEATURE:
<223> OTHER INFORMATION: An artificially synthesized target sequence for siRNA

<400> SEQUENCE: 45
ccatgattct gatgaggct                                                  19

```
<210> SEQ ID NO 46
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 46
tacttccagt gcgtggcaa                                                  19

<210> SEQ ID NO 47
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 47
gccatattat ggattcagt                                                  19

<210> SEQ ID NO 48
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 48
tgtacagcct catgacaga                                                  19

<210> SEQ ID NO 49
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 49
ggcaaattct cttctgatt                                                  19

<210> SEQ ID NO 50
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 50
ccacacatgt caattccaa                                                  19

<210> SEQ ID NO 51
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 51
gcgattcatt cccatcaat                                                  19

<210> SEQ ID NO 52
<211> LENGTH: 19
```

```
<212> TYPE: DNA
<213> ORGANISM: Artificial
<220> FEATURE:
<223> OTHER INFORMATION: An artificially synthesized target sequence for
      siRNA

<400> SEQUENCE: 52
tcaagacctt gaaagacta                                                19

<210> SEQ ID NO 53
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 53
caaaggattc caaggagaa                                                19

<210> SEQ ID NO 54
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 54
gattgcagct ggcatggaa                                                19

<210> SEQ ID NO 55
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 55
gccaacaggt cctcccaga                                                19

<210> SEQ ID NO 56
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 56
tatatggagt ctttgcaca                                                19

<210> SEQ ID NO 57
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 57
gggagggact ctcaagtca                                                19

<210> SEQ ID NO 58
<211> LENGTH: 19
<212> TYPE: DNA
<213> ORGANISM: Artificial
```

```
<220> FEATURE:
<223> OTHER INFORMATION: An artificially synthesized target sequence for
      siRNA

<400> SEQUENCE: 58
tggagtcttt gcacatgca                                                    19

<210> SEQ ID NO 59
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 59
ctcagatgag tatgaagaa                                                    19

<210> SEQ ID NO 60
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 60
cagcagaact gcactgcaa                                                    19

<210> SEQ ID NO 61
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 61
cccgtactgc gatgaaact                                                    19

<210> SEQ ID NO 62
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 62
ccttgaaaga ctataacaa                                                    19

<210> SEQ ID NO 63
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 63
tccatgagtt cctcatcat                                                    19

<210> SEQ ID NO 64
<211> LENGTH: 19
<212> TYPE: DNA
<213> ORGANISM: Artificial
<220> FEATURE:
<223> OTHER INFORMATION: An artificially synthesized target sequence for
```

-continued siRNA

<400> SEQUENCE: 64
ctttaagtct gatctgtgt                                                19

<210> SEQ ID NO 65
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 65
cacttccagt cacttatct                                                19

<210> SEQ ID NO 66
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 66
accaggaagt gattgagat                                                19

<210> SEQ ID NO 67
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 67
tcattcccat caatggata                                                19

<210> SEQ ID NO 68
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 68
tacgctttat ggaagaatt                                                19

<210> SEQ ID NO 69
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 69
ttcccgtact gcgatgaaa                                                19

<210> SEQ ID NO 70
<211> LENGTH: 19
<212> TYPE: DNA
<213> ORGANISM: Artificial
<220> FEATURE:
<223> OTHER INFORMATION: An artificially synthesized target sequence for
      siRNA

```
<400> SEQUENCE: 70
gtcacttctt tgtccacaa                                              19

<210> SEQ ID NO 71
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 71
gagaatgtcc tgtgtcaaa                                              19

<210> SEQ ID NO 72
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 72
cttccagtca cttatctga                                              19

<210> SEQ ID NO 73
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 73
gaagctccct ggtgcttca                                              19

<210> SEQ ID NO 74
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 74
gccagggtat tacaccaca                                              19

<210> SEQ ID NO 75
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 75
ctctttctgc tgtacgctt                                              19

<210> SEQ ID NO 76
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 76
```

-continued gtagagatgt caatgctga                                                19

<210> SEQ ID NO 77
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 77
gtgtcaaaca gagtacatt                                                19

<210> SEQ ID NO 78
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 78
gcaatggacg gaatttcaa                                                19

<210> SEQ ID NO 79
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 79
aactgtatcc ggattggaa                                                19

<210> SEQ ID NO 80
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 80
gtgcaagatt tattggcaa                                                19

<210> SEQ ID NO 81
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 81
catggaacat ctcaagtga                                                19

<210> SEQ ID NO 82
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 82
ctccctcagt gccagccca                                                19

-continued

<210> SEQ ID NO 83
<211> LENGTH: 19
<212> TYPE: DNA
<213> ORGANISM: Artificial
<220> FEATURE:
<223> OTHER INFORMATION: An artificially synthesized target sequence for
     siRNA

<400> SEQUENCE: 83
tctataaagg ccatctcta                                              19

<210> SEQ ID NO 84
<211> LENGTH: 19
<212> TYPE: DNA
<213> ORGANISM: Artificial
<220> FEATURE:
<223> OTHER INFORMATION: An artificially synthesized target sequence for
     siRNA

<400> SEQUENCE: 84
ctcagctggt tgctatcaa                                              19

<210> SEQ ID NO 85
<211> LENGTH: 19
<212> TYPE: DNA
<213> ORGANISM: Artificial
<220> FEATURE:
<223> OTHER INFORMATION: An artificially synthesized target sequence for
     siRNA

<400> SEQUENCE: 85
tcgatgaacc aatgaataa                                              19

<210> SEQ ID NO 86
<211> LENGTH: 19
<212> TYPE: DNA
<213> ORGANISM: Artificial
<220> FEATURE:
<223> OTHER INFORMATION: An artificially synthesized target sequence for
     siRNA

<400> SEQUENCE: 86
tgccgtcact caggaacaa                                              19

<210> SEQ ID NO 87
<211> LENGTH: 19
<212> TYPE: DNA
<213> ORGANISM: Artificial
<220> FEATURE:
<223> OTHER INFORMATION: An artificially synthesized target sequence for
     siRNA

<400> SEQUENCE: 87
catgtcaatt ccaaatcat                                              19

<210> SEQ ID NO 88
<211> LENGTH: 19
<212> TYPE: DNA
<213> ORGANISM: Artificial
<220> FEATURE:
<223> OTHER INFORMATION: An artificially synthesized target sequence for
     siRNA

<400> SEQUENCE: 88
cctacctcat catggaaca                                              19

<210> SEQ ID NO 89

```
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 89
gcaagcatct ttactagga                                              19

<210> SEQ ID NO 90
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 90
gtactgcgat gaaacttca                                              19

<210> SEQ ID NO 91
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 91
cggagagcaa cttcatgta                                              19

<210> SEQ ID NO 92
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 92
ccttgcagct cgcaatatt                                              19

<210> SEQ ID NO 93
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 93
ctatcaagac cttgaaaga                                              19

<210> SEQ ID NO 94
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 94
ctgcagcagt gatgaagat                                              19

<210> SEQ ID NO 95
<211> LENGTH: 19
<212> TYPE: DNA
```

-continued

```
<213> ORGANISM: Artificial
<220> FEATURE:
<223> OTHER INFORMATION: An artificially synthesized target sequence for
      siRNA

<400> SEQUENCE: 95
gcaacttcat gtaaagatt                                                19

<210> SEQ ID NO 96
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 96
tggcagatcc tataaataa                                                19

<210> SEQ ID NO 97
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 97
cattgcaatt cagattgca                                                19

<210> SEQ ID NO 98
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 98
actacagggt ccagagtaa                                                19

<210> SEQ ID NO 99
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 99
tgctgtacgc tttatggaa                                                19

<210> SEQ ID NO 100
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 100
cagagtgctg gaatgagat                                                19

<210> SEQ ID NO 101
<211> LENGTH: 19
<212> TYPE: DNA
<213> ORGANISM: Artificial
<220> FEATURE:
```

```
<223> OTHER INFORMATION: An artificially synthesized target sequence for
      siRNA

<400> SEQUENCE: 101
ctttcaccgc ccttcgttt                                                     19

<210> SEQ ID NO 102
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 102
tggttgctat caagacctt                                                     19

<210> SEQ ID NO 103
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 103
ctcaaagcaa gcatcttta                                                     19

<210> SEQ ID NO 104
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 104
ctcagaacca gcgattcat                                                     19

<210> SEQ ID NO 105
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 105
atctctatct cccaggcat                                                     19

<210> SEQ ID NO 106
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 106
cagctggttg ctatcaaga                                                     19

<210> SEQ ID NO 107
<211> LENGTH: 19
<212> TYPE: DNA
<213> ORGANISM: Artificial
<220> FEATURE:
<223> OTHER INFORMATION: An artificially synthesized target sequence for
      siRNA
```

-continued

```
<400> SEQUENCE: 107
gagaccaaga tttaaagat                                                19

<210> SEQ ID NO 108
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 108
ctgcccacct cccaagagt                                                19

<210> SEQ ID NO 109
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 109
gcgattcaaa ggattccaa                                                19

<210> SEQ ID NO 110
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 110
ctagtcactt ctttgtcca                                                19

<210> SEQ ID NO 111
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 111
ttgctttact cttcttctt                                                19

<210> SEQ ID NO 112
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 112
cagagtaagt ccttgctgc                                                19

<210> SEQ ID NO 113
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 113
```

```
caccgccctt cgtttccca                                                19
```

<210> SEQ ID NO 114
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 114

```
cagacacagg ctacttcca                                                19
```

<210> SEQ ID NO 115
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 115

```
gaaatttact ccgctgatt                                                19
```

<210> SEQ ID NO 116
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 116

```
gtaagtcctt gctgcccat                                                19
```

<210> SEQ ID NO 117
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 117

```
ctgctgtacg ctttatgga                                                19
```

<210> SEQ ID NO 118
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 118

```
aggatactca gatgagtat                                                19
```

<210> SEQ ID NO 119
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 119

```
cacacatgtc aattccaaa                                                19
```

<210> SEQ ID NO 120
<211> LENGTH: 19
<212> TYPE: DNA
<213> ORGANISM: Artificial
<220> FEATURE:
<223> OTHER INFORMATION: An artificially synthesized target sequence for siRNA

<400> SEQUENCE: 120
gaactgcact gcaaagtct                                               19

<210> SEQ ID NO 121
<211> LENGTH: 19
<212> TYPE: DNA
<213> ORGANISM: Artificial
<220> FEATURE:
<223> OTHER INFORMATION: An artificially synthesized target sequence for siRNA

<400> SEQUENCE: 121
cagtcagtgc tgaattagt                                               19

<210> SEQ ID NO 122
<211> LENGTH: 19
<212> TYPE: DNA
<213> ORGANISM: Artificial
<220> FEATURE:
<223> OTHER INFORMATION: An artificially synthesized target sequence for siRNA

<400> SEQUENCE: 122
gacacaggct acttccagt                                               19

<210> SEQ ID NO 123
<211> LENGTH: 19
<212> TYPE: DNA
<213> ORGANISM: Artificial
<220> FEATURE:
<223> OTHER INFORMATION: An artificially synthesized target sequence for siRNA

<400> SEQUENCE: 123
cagaagctgc gaactgtat                                               19

<210> SEQ ID NO 124
<211> LENGTH: 19
<212> TYPE: DNA
<213> ORGANISM: Artificial
<220> FEATURE:
<223> OTHER INFORMATION: An artificially synthesized target sequence for siRNA

<400> SEQUENCE: 124
ttactcttct tcttcattt                                               19

<210> SEQ ID NO 125
<211> LENGTH: 19
<212> TYPE: DNA
<213> ORGANISM: Artificial
<220> FEATURE:
<223> OTHER INFORMATION: An artificially synthesized target sequence for siRNA

<400> SEQUENCE: 125
ttgcagctgg catggaata                                               19

<210> SEQ ID NO 126
<211> LENGTH: 19
<212> TYPE: DNA
<213> ORGANISM: Artificial
<220> FEATURE:
<223> OTHER INFORMATION: An artificially synthesized target sequence for siRNA

<400> SEQUENCE: 126
tcatttgcgt ctgtcggaa                                              19

<210> SEQ ID NO 127
<211> LENGTH: 19
<212> TYPE: DNA
<213> ORGANISM: Artificial
<220> FEATURE:
<223> OTHER INFORMATION: An artificially synthesized target sequence for siRNA

<400> SEQUENCE: 127
cagctgcctt cactatgat                                              19

<210> SEQ ID NO 128
<211> LENGTH: 19
<212> TYPE: DNA
<213> ORGANISM: Artificial
<220> FEATURE:
<223> OTHER INFORMATION: An artificially synthesized target sequence for siRNA

<400> SEQUENCE: 128
atgctcagct ggttgctat                                              19

<210> SEQ ID NO 129
<211> LENGTH: 19
<212> TYPE: DNA
<213> ORGANISM: Artificial
<220> FEATURE:
<223> OTHER INFORMATION: An artificially synthesized target sequence for siRNA

<400> SEQUENCE: 129
gaaacttcat ccgtcccaa                                              19

<210> SEQ ID NO 130
<211> LENGTH: 19
<212> TYPE: DNA
<213> ORGANISM: Artificial
<220> FEATURE:
<223> OTHER INFORMATION: An artificially synthesized target sequence for siRNA

<400> SEQUENCE: 130
tgacttgtgt cgcgatgaa                                              19

<210> SEQ ID NO 131
<211> LENGTH: 19
<212> TYPE: DNA
<213> ORGANISM: Artificial
<220> FEATURE:
<223> OTHER INFORMATION: An artificially synthesized target sequence for siRNA

<400> SEQUENCE: 131
ttccttccct gtgccacta                                              19

<210> SEQ ID NO 132
<211> LENGTH: 19

-continued

```
<212> TYPE: DNA
<213> ORGANISM: Artificial
<220> FEATURE:
<223> OTHER INFORMATION: An artificially synthesized target sequence for
      siRNA

<400> SEQUENCE: 132
tcctttcggt ccaccatct                                                   19

<210> SEQ ID NO 133
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 133
gccatcatgt atggcaaat                                                   19

<210> SEQ ID NO 134
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 134
gaccaagatt taaagatat                                                   19

<210> SEQ ID NO 135
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 135
ctgtcagtca gtgctgaat                                                   19

<210> SEQ ID NO 136
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 136
ctcatcatgg aacatctca                                                   19

<210> SEQ ID NO 137
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 137
caccgaatct atgatttct                                                   19

<210> SEQ ID NO 138
<211> LENGTH: 19
<212> TYPE: DNA
<213> ORGANISM: Artificial
```

```
<220> FEATURE:
<223> OTHER INFORMATION: An artificially synthesized target sequence for
      siRNA

<400> SEQUENCE: 138
cacacacttt caccgccct                                                    19

<210> SEQ ID NO 139
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 139
tgatctgtgt gacatccca                                                    19

<210> SEQ ID NO 140
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 140
caggtcctcc cagagtgat                                                    19

<210> SEQ ID NO 141
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 141
gatttctgca gaactgtaa                                                    19

<210> SEQ ID NO 142
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 142
ctgtacgctt tatggaaga                                                    19

<210> SEQ ID NO 143
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 143
ctggagtctt gtttgtcaa                                                    19

<210> SEQ ID NO 144
<211> LENGTH: 19
<212> TYPE: DNA
<213> ORGANISM: Artificial
<220> FEATURE:
<223> OTHER INFORMATION: An artificially synthesized target sequence for
``` siRNA

<400> SEQUENCE: 144
ctcagtgcca gcccagtga                                            19

<210> SEQ ID NO 145
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 145
tggaatacct gtctagtca                                            19

<210> SEQ ID NO 146
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 146
cccttcgttt cccagagct                                            19

<210> SEQ ID NO 147
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 147
ctcgatgaac caatgaata                                            19

<210> SEQ ID NO 148
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 148
aatgctgaat gcatataaa                                            19

<210> SEQ ID NO 149
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 149
gagccagggt attacacca                                            19

<210> SEQ ID NO 150
<211> LENGTH: 19
<212> TYPE: DNA
<213> ORGANISM: Artificial
<220> FEATURE:
<223> OTHER INFORMATION: An artificially synthesized target sequence for
      siRNA

```
<400> SEQUENCE: 150
gagtcttgtt tgtcaagtt                                               19

<210> SEQ ID NO 151
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 151
ctggccattg ctttactct                                               19

<210> SEQ ID NO 152
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 152
tctaggagac caagattta                                               19

<210> SEQ ID NO 153
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 153
ggaagcaaat attcctta                                                19

<210> SEQ ID NO 154
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 154
gggattgcat gtgcaagat                                               19

<210> SEQ ID NO 155
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 155
caatcaggaa gcaaatatt                                               19

<210> SEQ ID NO 156
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 156
```
ttcatgtaaa gatttcaga                                        19

<210> SEQ ID NO 157
<211> LENGTH: 19
<212> TYPE: DNA
<213> ORGANISM: Artificial
<220> FEATURE:
<223> OTHER INFORMATION: An artificially synthesized target sequence for
    siRNA

<400> SEQUENCE: 157
gagttcctca tcatgagat                                        19

<210> SEQ ID NO 158
<211> LENGTH: 19
<212> TYPE: DNA
<213> ORGANISM: Artificial
<220> FEATURE:
<223> OTHER INFORMATION: An artificially synthesized target sequence for
    siRNA

<400> SEQUENCE: 158
gctgcgaact gtatccgga                                        19

<210> SEQ ID NO 159
<211> LENGTH: 19
<212> TYPE: DNA
<213> ORGANISM: Artificial
<220> FEATURE:
<223> OTHER INFORMATION: An artificially synthesized target sequence for
    siRNA

<400> SEQUENCE: 159
ccactggagt cttgtttgt                                        19

<210> SEQ ID NO 160
<211> LENGTH: 19
<212> TYPE: DNA
<213> ORGANISM: Artificial
<220> FEATURE:
<223> OTHER INFORMATION: An artificially synthesized target sequence for
    siRNA

<400> SEQUENCE: 160
gatggattct gtcagccat                                        19

<210> SEQ ID NO 161
<211> LENGTH: 19
<212> TYPE: DNA
<213> ORGANISM: Artificial
<220> FEATURE:
<223> OTHER INFORMATION: An artificially synthesized target sequence for
    siRNA

<400> SEQUENCE: 161
atcccagcgt gcgattcaa                                        19

<210> SEQ ID NO 162
<211> LENGTH: 19
<212> TYPE: DNA
<213> ORGANISM: Artificial
<220> FEATURE:
<223> OTHER INFORMATION: An artificially synthesized target sequence for
    siRNA

<400> SEQUENCE: 162
acgccaatat tcatggaca                                        19

<210> SEQ ID NO 163
<211> LENGTH: 19
<212> TYPE: DNA
<213> ORGANISM: Artificial
<220> FEATURE:
<223> OTHER INFORMATION: An artificially synthesized target sequence for siRNA

<400> SEQUENCE: 163
cactgcaagt ccaggatac                                               19

<210> SEQ ID NO 164
<211> LENGTH: 19
<212> TYPE: DNA
<213> ORGANISM: Artificial
<220> FEATURE:
<223> OTHER INFORMATION: An artificially synthesized target sequence for siRNA

<400> SEQUENCE: 164
gtgactagct tgccctcat                                               19

<210> SEQ ID NO 165
<211> LENGTH: 19
<212> TYPE: DNA
<213> ORGANISM: Artificial
<220> FEATURE:
<223> OTHER INFORMATION: An artificially synthesized target sequence for siRNA

<400> SEQUENCE: 165
gaattagtgc ctacctcat                                               19

<210> SEQ ID NO 166
<211> LENGTH: 19
<212> TYPE: DNA
<213> ORGANISM: Artificial
<220> FEATURE:
<223> OTHER INFORMATION: An artificially synthesized target sequence for siRNA

<400> SEQUENCE: 166
cagatgagta tgaagaaga                                               19

<210> SEQ ID NO 167
<211> LENGTH: 19
<212> TYPE: DNA
<213> ORGANISM: Artificial
<220> FEATURE:
<223> OTHER INFORMATION: An artificially synthesized target sequence for siRNA

<400> SEQUENCE: 167
ctgcacattg caattcaga                                               19

<210> SEQ ID NO 168
<211> LENGTH: 19
<212> TYPE: DNA
<213> ORGANISM: Artificial
<220> FEATURE:
<223> OTHER INFORMATION: An artificially synthesized target sequence for siRNA

<400> SEQUENCE: 168
ccctcgatga accaatgaa                                               19

<210> SEQ ID NO 169

```
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 169
ctctgggcca gacagcaga                                               19

<210> SEQ ID NO 170
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 170
cagagaaatt tactccgct                                               19

<210> SEQ ID NO 171
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 171
ccaagaaaca gagctgtca                                               19

<210> SEQ ID NO 172
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 172
gtctctgggc cagacagca                                               19

<210> SEQ ID NO 173
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 173
tgaattagtg cctacctca                                               19

<210> SEQ ID NO 174
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 174
ctataaaggc catctctat                                               19

<210> SEQ ID NO 175
<211> LENGTH: 19
<212> TYPE: DNA
```

-continued

```
<213> ORGANISM: Artificial
<220> FEATURE:
<223> OTHER INFORMATION: An artificially synthesized target sequence for
      siRNA

<400> SEQUENCE: 175
ggaagaattg ggtgagtgt                                                       19

<210> SEQ ID NO 176
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 176
gtgaaatcct ggagaatgt                                                       19

<210> SEQ ID NO 177
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 177
caggcatgga ccatgctca                                                       19

<210> SEQ ID NO 178
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 178
ggcaccagtc cagaggcaa                                                       19

<210> SEQ ID NO 179
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 179
cttcgtttcc cagagctga                                                       19

<210> SEQ ID NO 180
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 180
cactgcaaag tctctggga                                                       19

<210> SEQ ID NO 181
<211> LENGTH: 19
<212> TYPE: DNA
<213> ORGANISM: Artificial
<220> FEATURE:
```

```
<223> OTHER INFORMATION: An artificially synthesized target sequence for
      siRNA

<400> SEQUENCE: 181
ctgtgaaatc cagcctgga                                                   19

<210> SEQ ID NO 182
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 182
ccgtcagtgt gaccaaatc                                                   19

<210> SEQ ID NO 183
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 183
gctacctctt tctgctgta                                                   19

<210> SEQ ID NO 184
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 184
caggctactt ccagtgcgt                                                   19

<210> SEQ ID NO 185
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 185
gacatcccag cgtgcgatt                                                   19

<210> SEQ ID NO 186
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 186
aacaaagatt cttacctga                                                   19

<210> SEQ ID NO 187
<211> LENGTH: 19
<212> TYPE: DNA
<213> ORGANISM: Artificial
<220> FEATURE:
<223> OTHER INFORMATION: An artificially synthesized target sequence for
      siRNA
```

```
<400> SEQUENCE: 187
gtgattgaga tggtgagaa                                                19

<210> SEQ ID NO 188
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 188
atgctcctgt ggtccagga                                                19

<210> SEQ ID NO 189
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 189
catcctggtg gaatgggta                                                19

<210> SEQ ID NO 190
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 190
ttaagtctga tctgtgtga                                                19

<210> SEQ ID NO 191
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 191
gaaacagagc tgtcagtca                                                19

<210> SEQ ID NO 192
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 192
gccatacaga gggattgca                                                19

<210> SEQ ID NO 193
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 193
```
taggtgccgt cactcagga                                                19

<210> SEQ ID NO 194
<211> LENGTH: 19
<212> TYPE: DNA
<213> ORGANISM: Artificial
<220> FEATURE:
<223> OTHER INFORMATION: An artificially synthesized target sequence for
     siRNA

<400> SEQUENCE: 194
aagatcaaat cccatgatt                                                19

<210> SEQ ID NO 195
<211> LENGTH: 19
<212> TYPE: DNA
<213> ORGANISM: Artificial
<220> FEATURE:
<223> OTHER INFORMATION: An artificially synthesized target sequence for
     siRNA

<400> SEQUENCE: 195
cgatgaatgt gaaatcctg                                                19

<210> SEQ ID NO 196
<211> LENGTH: 19
<212> TYPE: DNA
<213> ORGANISM: Artificial
<220> FEATURE:
<223> OTHER INFORMATION: An artificially synthesized target sequence for
     siRNA

<400> SEQUENCE: 196
ctcttaccat gctctgaag                                                19

<210> SEQ ID NO 197
<211> LENGTH: 19
<212> TYPE: DNA
<213> ORGANISM: Artificial
<220> FEATURE:
<223> OTHER INFORMATION: An artificially synthesized target sequence for
     siRNA

<400> SEQUENCE: 197
gtgccagccc agtgagtaa                                                19

<210> SEQ ID NO 198
<211> LENGTH: 19
<212> TYPE: DNA
<213> ORGANISM: Artificial
<220> FEATURE:
<223> OTHER INFORMATION: An artificially synthesized target sequence for
     siRNA

<400> SEQUENCE: 198
agctgtcagt cagtgctga                                                19

<210> SEQ ID NO 199
<211> LENGTH: 19
<212> TYPE: DNA
<213> ORGANISM: Artificial
<220> FEATURE:
<223> OTHER INFORMATION: An artificially synthesized target sequence for
     siRNA

<400> SEQUENCE: 199
tggactccag ccatattat                                                19

```
<210> SEQ ID NO 200
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 200
tggattcagt aaccaggaa                                                       19

<210> SEQ ID NO 201
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 201
tccaaatcat cctggtgga                                                       19

<210> SEQ ID NO 202
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 202
tcctgggagg gactctcaa                                                       19

<210> SEQ ID NO 203
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 203
cacccagaat gtacagcct                                                       19

<210> SEQ ID NO 204
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 204
catggacaca ccgaatcta                                                       19

<210> SEQ ID NO 205
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 205
cagatcacag ctgccttca                                                       19
```

```
<210> SEQ ID NO 206
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 206
gatcaaatcc catgattct                                                    19

<210> SEQ ID NO 207
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 207
aatgtgaaat cctggagaa                                                    19

<210> SEQ ID NO 208
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 208
gccattgctt tactcttct                                                    19

<210> SEQ ID NO 209
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 209
atttgcgtct gtcggaata                                                    19

<210> SEQ ID NO 210
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 210
gaccttgcag ctcgcaata                                                    19

<210> SEQ ID NO 211
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 211
agcttgccct catcaggat                                                    19

<210> SEQ ID NO 212
<211> LENGTH: 19
```

```
<212> TYPE: DNA
<213> ORGANISM: Artificial
<220> FEATURE:
<223> OTHER INFORMATION: An artificially synthesized target sequence for
      siRNA

<400> SEQUENCE: 212
ccttctaggt gccgtcact                                                    19

<210> SEQ ID NO 213
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 213
ctgattacta cagggtcca                                                    19

<210> SEQ ID NO 214
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 214
ggacggaatt tcaacaaga                                                    19

<210> SEQ ID NO 215
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 215
tgtcaatgct gaatgcata                                                    19

<210> SEQ ID NO 216
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 216
cgcaccgtct atatggagt                                                    19

<210> SEQ ID NO 217
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 217
ccctcagtgc cagcccagt                                                    19

<210> SEQ ID NO 218
<211> LENGTH: 19
<212> TYPE: DNA
<213> ORGANISM: Artificial
```

```
<220> FEATURE:
<223> OTHER INFORMATION: An artificially synthesized target sequence for
      siRNA

<400> SEQUENCE: 218
caaatcatcc tggtggaat                                                    19

<210> SEQ ID NO 219
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 219
ctctcctttc ggtccacca                                                    19

<210> SEQ ID NO 220
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 220
gagcaaggct aaagagcta                                                    19

<210> SEQ ID NO 221
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 221
attctcttct gattcagat                                                    19

<210> SEQ ID NO 222
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 222
cctgtctagt cacttcttt                                                    19

<210> SEQ ID NO 223
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 223
ctccatgagt tcctcatca                                                    19

<210> SEQ ID NO 224
<211> LENGTH: 19
<212> TYPE: DNA
<213> ORGANISM: Artificial
<220> FEATURE:
<223> OTHER INFORMATION: An artificially synthesized target sequence for
```

-continued siRNA

<400> SEQUENCE: 224
aacccaagag caaggctaa                                              19

<210> SEQ ID NO 225
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 225
ctgaccctcg atgaaccaa                                              19

<210> SEQ ID NO 226
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 226
ttggcaaccg caccgtcta                                              19

<210> SEQ ID NO 227
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 227
cccagcgtgc gattcaaag                                              19

<210> SEQ ID NO 228
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 228
cagtgatgaa gatgggact                                              19

<210> SEQ ID NO 229
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 229
ccattccttc cctgtgcca                                              19

<210> SEQ ID NO 230
<211> LENGTH: 19
<212> TYPE: DNA
<213> ORGANISM: Artificial
<220> FEATURE:
<223> OTHER INFORMATION: An artificially synthesized target sequence for
      siRNA

```
<400> SEQUENCE: 230
tcaagtcaca caagctcta                                                19

<210> SEQ ID NO 231
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 231
ctcccaccat ccgctggtt                                                19

<210> SEQ ID NO 232
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 232
atcacagctg ccttcacta                                                19

<210> SEQ ID NO 233
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 233
ccctgtgcca ctatgcctt                                                19

<210> SEQ ID NO 234
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 234
tgaagactgc ccacccaga                                                19

<210> SEQ ID NO 235
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 235
ccaggatact cagatgagt                                                19

<210> SEQ ID NO 236
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 236
```
cagctggcat ggaatacct                                              19

<210> SEQ ID NO 237
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 237
ccatattatg gattcagta                                              19

<210> SEQ ID NO 238
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 238
tcccatggca gatcctata                                              19

<210> SEQ ID NO 239
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 239
ctgcgaactg tatccggat                                              19

<210> SEQ ID NO 240
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 240
aagccatcat gtatggcaa                                              19

<210> SEQ ID NO 241
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 241
gccagagagc ccagaagct                                              19

<210> SEQ ID NO 242
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 242
gtgcttcacc ttggatgaa                                              19

```
<210> SEQ ID NO 243
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 243
cacacaagct ctactactc                                                   19

<210> SEQ ID NO 244
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 244
ccttcactat gattggcac                                                   19

<210> SEQ ID NO 245
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 245
accagcgatt cattcccat                                                   19

<210> SEQ ID NO 246
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 246
ctgccaaact gtgaagatc                                                   19

<210> SEQ ID NO 247
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 247
ccgcccttcg tttcccaga                                                   19

<210> SEQ ID NO 248
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 248
tgaagaagat ggattctgt                                                   19

<210> SEQ ID NO 249
```

```
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 249
caacaagaag cctccctaa                                                  19

<210> SEQ ID NO 250
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 250
tgcccaccca gaatgtaca                                                  19

<210> SEQ ID NO 251
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 251
accgcaccgt ctatatgga                                                  19

<210> SEQ ID NO 252
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 252
cagtgccagc ccagtgagt                                                  19

<210> SEQ ID NO 253
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 253
cagtaaccag gaagtgatt                                                  19

<210> SEQ ID NO 254
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 254
acttctttgt ccacaagga                                                  19

<210> SEQ ID NO 255
<211> LENGTH: 19
<212> TYPE: DNA
```

```
<213> ORGANISM: Artificial
<220> FEATURE:
<223> OTHER INFORMATION: An artificially synthesized target sequence for
      siRNA

<400> SEQUENCE: 255
tttactacca cacatgtca                                                  19

<210> SEQ ID NO 256
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 256
ccagattgct ggtttcatt                                                  19

<210> SEQ ID NO 257
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 257
agcaaatatt cctttacta                                                  19

<210> SEQ ID NO 258
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 258
agatgagtat gaagaagat                                                  19

<210> SEQ ID NO 259
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 259
actggagtct tgtttgtca                                                  19

<210> SEQ ID NO 260
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 260
ttcatttgcg tctgtcgga                                                  19

<210> SEQ ID NO 261
<211> LENGTH: 19
<212> TYPE: DNA
<213> ORGANISM: Artificial
<220> FEATURE:
```

```
<223> OTHER INFORMATION: An artificially synthesized target sequence for
      siRNA

<400> SEQUENCE: 261
ttctaggtgc cgtcactca                                                  19

<210> SEQ ID NO 262
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 262
gattccaagg agaagaata                                                  19

<210> SEQ ID NO 263
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 263
cacaagctct actactcct                                                  19

<210> SEQ ID NO 264
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 264
cggcaccagt ccagaggca                                                  19

<210> SEQ ID NO 265
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 265
ttcctactgc cgcaaccca                                                  19

<210> SEQ ID NO 266
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 266
cctttactac cacacatgt                                                  19

<210> SEQ ID NO 267
<211> LENGTH: 19
<212> TYPE: DNA
<213> ORGANISM: Artificial
<220> FEATURE:
<223> OTHER INFORMATION: An artificially synthesized target sequence for
      siRNA
```

```
<400> SEQUENCE: 267
gatttaaaga tattcacgt                                                    19

<210> SEQ ID NO 268
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 268
ctgtacatac tagtgccaa                                                    19

<210> SEQ ID NO 269
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 269
caacttcatg taaagattt                                                    19

<210> SEQ ID NO 270
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 270
attccaagga gaagaataa                                                    19

<210> SEQ ID NO 271
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 271
ggcatggaat acctgtcta                                                    19

<210> SEQ ID NO 272
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 272
ccagcccagt gagtaatct                                                    19

<210> SEQ ID NO 273
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 273
```

```
tctcggctgc ggattagaa                                                 19

<210> SEQ ID NO 274
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 274
ccatggcaga tcctataaa                                                 19

<210> SEQ ID NO 275
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 275
gggactctca agtcacaca                                                 19

<210> SEQ ID NO 276
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 276
cttacctgac cctcgatga                                                 19

<210> SEQ ID NO 277
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 277
caatggatac ccaatacct                                                 19

<210> SEQ ID NO 278
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 278
gtgctggaat gagattcct                                                 19

<210> SEQ ID NO 279
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 279
tctttctgct gtacgcttt                                                 19
```

<210> SEQ ID NO 280
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 280
cagacaacct ccctcagtg                                                  19

<210> SEQ ID NO 281
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 281
cttccagtgc gtggcaaca                                                  19

<210> SEQ ID NO 282
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 282
ggtggtttct tccactgga                                                  19

<210> SEQ ID NO 283
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 283
cagatatcct aattacatg                                                  19

<210> SEQ ID NO 284
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 284
tgaatggagg ccattccta                                                  19

<210> SEQ ID NO 285
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 285
ttcattccca tcaatggat                                                  19

```
<210> SEQ ID NO 286
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 286
ctctcggctg cggattaga                                                      19

<210> SEQ ID NO 287
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 287
taatcggaga gcaacttca                                                      19

<210> SEQ ID NO 288
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 288
atactcagat gagtatgaa                                                      19

<210> SEQ ID NO 289
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 289
gaagccatca tgtatggca                                                      19

<210> SEQ ID NO 290
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 290
taggagacgc caatattca                                                      19

<210> SEQ ID NO 291
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 291
ggcacttcca gtcacttat                                                      19

<210> SEQ ID NO 292
<211> LENGTH: 19
```

```
<212> TYPE: DNA
<213> ORGANISM: Artificial
<220> FEATURE:
<223> OTHER INFORMATION: An artificially synthesized target sequence for
      siRNA

<400> SEQUENCE: 292
ccattgcttt actcttctt                                                   19

<210> SEQ ID NO 293
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 293
gtttcattgg cccgccaat                                                   19

<210> SEQ ID NO 294
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 294
gttataacag cacaggtgt                                                   19

<210> SEQ ID NO 295
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 295
ggctctcggc tgcggatta                                                   19

<210> SEQ ID NO 296
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 296
agaccaagat ttaaagata                                                   19

<210> SEQ ID NO 297
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 297
gggaucgcgc ucgcggcau                                                   19

<210> SEQ ID NO 298
```

```
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 298
agagcuuugc agacguccc                                                    19

<210> SEQ ID NO 299
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 299
gagcccgugg auguucugc                                                    19

<210> SEQ ID NO 300
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 300
ugcaccggcc gcgccgccg                                                    19

<210> SEQ ID NO 301
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 301
gaaacagagc ugucaguca                                                    19

<210> SEQ ID NO 302
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 302
acagagcugu cagucagug                                                    19

<210> SEQ ID NO 303
```

```
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 303
uuagugccua ccucaucau                                                    19

<210> SEQ ID NO 304
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 304
caucucaagu gaacucaac                                                    19

<210> SEQ ID NO 305
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 305
gugaacucaa caaagauuc                                                    19

<210> SEQ ID NO 306
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 306
cucaacaaag auucuuacc                                                    19

<210> SEQ ID NO 307
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 307
caaagauucu uaccugacc                                                    19

<210> SEQ ID NO 308
```

```
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 308
agauucuuac cugacccuc                                               19

<210> SEQ ID NO 309
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 309
ccaaugaaua acaucacca                                               19

<210> SEQ ID NO 310
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 310
ugaauaacau caccacguc                                               19

<210> SEQ ID NO 311
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 311
uaacaucacc acgucucg                                                19

<210> SEQ ID NO 312
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 312
caucaccacg ucucugggc                                               19

<210> SEQ ID NO 313
```

```
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 313
cugcacugca aagucucug                                                   19

<210> SEQ ID NO 314
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 314
agucucuggg aauccaccu                                                   19

<210> SEQ ID NO 315
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 315
uccaccuccc accauccgc                                                   19

<210> SEQ ID NO 316
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 316
aaaugaugcu ccugugguc                                                   19

<210> SEQ ID NO 317
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 317
augaugcucc uguggucca                                                   19

<210> SEQ ID NO 318
```

```
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 318
accucgacac cacagacac                                                  19

<210> SEQ ID NO 319
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 319
caaacggcaa ggagguggu                                                  19

<210> SEQ ID NO 320
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 320
ggaggugguu ucuuccacu                                                  19

<210> SEQ ID NO 321
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 321
guuuggcccc ccucccacu                                                  19

<210> SEQ ID NO 322
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 322
guccaggaua cucagauga                                                  19

<210> SEQ ID NO 323
```

-continued

```
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 323
gaagauggau ucugucagc                                                  19

<210> SEQ ID NO 324
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 324
gauggauucu gucagccau                                                  19

<210> SEQ ID NO 325
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 325
gauuuauugg caaccgcac                                                  19

<210> SEQ ID NO 326
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 326
ccgcaccguc uauauggag                                                  19

<210> SEQ ID NO 327
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 327
ggggaaauag aaaaucaga                                                  19

<210> SEQ ID NO 328
```

```
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 328
auagaaaauc agaucacag                                                    19

<210> SEQ ID NO 329
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 329
aaucagauca cagcugccu                                                    19

<210> SEQ ID NO 330
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 330
ucagaucaca gcugccuuc                                                    19

<210> SEQ ID NO 331
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 331
guguucucag uucgccauu                                                    19

<210> SEQ ID NO 332
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 332
acuucauccg ucccaaagc                                                    19

<210> SEQ ID NO 333
```

```
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 333
agccccguga cuugugucg                                                    19

<210> SEQ ID NO 334
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 334
ugugaaaucc uggagaaug                                                    19

<210> SEQ ID NO 335
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 335
auccuggaga auguccugu                                                    19

<210> SEQ ID NO 336
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 336
uguccugugu caaacagag                                                    19

<210> SEQ ID NO 337
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 337
acagaguaca uuuuugcaa                                                    19

<210> SEQ ID NO 338
```

```
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 338
gaucaaaucc caugauucu                                                      19

<210> SEQ ID NO 339
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 339
aucccaugau ucugaugag                                                      19

<210> SEQ ID NO 340
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 340
acugccaaac ugugaagau                                                      19

<210> SEQ ID NO 341
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 341
acugugaaga ucuccccca                                                      19

<210> SEQ ID NO 342
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 342
gaucuccccc agccagaga                                                      19

<210> SEQ ID NO 343
```

```
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 343
gcugcgaacu guauccgga                                              19

<210> SEQ ID NO 344
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 344
cuguauccgg auuggaauu                                              19

<210> SEQ ID NO 345
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 345
uucccauggc agauccuau                                              19

<210> SEQ ID NO 346
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 346
auaaaaauca caaguguua                                              19

<210> SEQ ID NO 347
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 347
aaaucacaag uguuauaac                                              19

<210> SEQ ID NO 348
```

```
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 348
aucacaagug uuauaacag                                                        19

<210> SEQ ID NO 349
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 349
guguuauaac agcacaggu                                                        19

<210> SEQ ID NO 350
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 350
cagcacaggu guggacuac                                                        19

<210> SEQ ID NO 351
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 351
aucagggcgc cagugccag                                                        19

<210> SEQ ID NO 352
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 352
uucccaguau ccccacaca                                                        19

<210> SEQ ID NO 353
```

```
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 353
uggaggccau uccuacugc                                                   19

<210> SEQ ID NO 354
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 354
cccagggaau caaaaggaa                                                   19

<210> SEQ ID NO 355
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 355
ucaaaaggaa gcucccugg                                                   19

<210> SEQ ID NO 356
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 356
aaggaagcuc ccuggugcu                                                   19

<210> SEQ ID NO 357
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 357
ggaagcuccc uggugcuuc                                                   19

<210> SEQ ID NO 358
```

```
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 358
gcucccuggu gcuucaccu                                                  19

<210> SEQ ID NO 359
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 359
aacuuuaagu cugaucugu                                                  19

<210> SEQ ID NO 360
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 360
cuuuaagucu gaucugugu                                                  19

<210> SEQ ID NO 361
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 361
gucugaucug ugugacauc                                                  19

<210> SEQ ID NO 362
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 362
aggauuccaa ggagaagaa                                                  19

<210> SEQ ID NO 363
```

```
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 363
ggagaagaau aaaauggaa                                                    19

<210> SEQ ID NO 364
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 364
gaauaaaaug gaaauccug                                                    19

<210> SEQ ID NO 365
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 365
uaaaauggaa auccuguac                                                    19

<210> SEQ ID NO 366
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 366
aauggaaauc cuguacaua                                                    19

<210> SEQ ID NO 367
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 367
uggaaauccu guacauacu                                                    19

<210> SEQ ID NO 368
```

```
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 368
auccuguaca uacuagugc                                                  19

<210> SEQ ID NO 369
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 369
guguggccau uccccuggc                                                  19

<210> SEQ ID NO 370
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 370
uaaccagaag ucaucgucg                                                  19

<210> SEQ ID NO 371
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 371
ccagaaguca ucgucggca                                                  19

<210> SEQ ID NO 372
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 372
gucaucgucg gcaccaguc                                                  19

<210> SEQ ID NO 373
```

```
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 373
ccaaaacacg ucagagguc                                                  19

<210> SEQ ID NO 374
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 374
aacacgucag aggucaaaa                                                  19

<210> SEQ ID NO 375
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 375
cacgucagag gucaaaaug                                                  19

<210> SEQ ID NO 376
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 376
aauguagaga ugucaaugc                                                  19

<210> SEQ ID NO 377
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 377
uguagagaug ucaaugcug                                                  19

<210> SEQ ID NO 378
```

```
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 378
ugcugaaugc auauaaacc                                                  19

<210> SEQ ID NO 379
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 379
ugcauauaaa cccaagagc                                                  19

<210> SEQ ID NO 380
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 380
acccaagagc aaggcuaaa                                                  19

<210> SEQ ID NO 381
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 381
gagcaaggcu aaagagcua                                                  19

<210> SEQ ID NO 382
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 382
ggcuaaagag cuaccucuu                                                  19

<210> SEQ ID NO 383
```

```
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 383
agagcuaccu cuuucugcu                                                   19

<210> SEQ ID NO 384
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 384
gaauugggug agugugccu                                                   19

<210> SEQ ID NO 385
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 385
uugggugagu gugccuuug                                                   19

<210> SEQ ID NO 386
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 386
aaaucuauaa aggccaucu                                                   19

<210> SEQ ID NO 387
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 387
aucuauaaag gccaucucu                                                   19

<210> SEQ ID NO 388
```

```
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 388
aggccaucuc uaucuccca                                                  19

<210> SEQ ID NO 389
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 389
gaccuugaaa gacuauaac                                                  19

<210> SEQ ID NO 390
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 390
agacuauaac aacccccag                                                  19

<210> SEQ ID NO 391
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 391 caaccccag cauggacg                                                    19

<210> SEQ ID NO 392
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 392
cccccagcaa uggacggaa                                                  19

<210> SEQ ID NO 393
```

```
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 393
uggacggaau uucaacaag                                                   19

<210> SEQ ID NO 394
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 394
uuucaacaag aagccuccc                                                   19

<210> SEQ ID NO 395
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 395
caagaagccu cccuaaugg                                                   19

<210> SEQ ID NO 396
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 396
gaagccuccc uaauggcag                                                   19

<210> SEQ ID NO 397
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 397
gccucccuaa uggcagaac                                                   19

<210> SEQ ID NO 398
```

```
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 398
uggcagaacu gcaccaccc                                                    19

<210> SEQ ID NO 399
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 399
cugcaccacc ccaauauug                                                    19

<210> SEQ ID NO 400
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 400
uauugucugc cuucuaggu                                                    19

<210> SEQ ID NO 401
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 401
caaccugugu gcaugcuuu                                                    19

<210> SEQ ID NO 402
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 402
ccugugugca ugcuuuuug                                                    19

<210> SEQ ID NO 403
```

```
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 403 ucaggggau cuccaugag                                                       19

<210> SEQ ID NO 404
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 404
gaugggacug ugaaaucca                                                      19

<210> SEQ ID NO 405
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 405
auccagccug gaccacgga                                                      19

<210> SEQ ID NO 406
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 406
uucagauugc agcuggcau                                                      19

<210> SEQ ID NO 407
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 407
uaccugucua gucacuucu                                                      19

<210> SEQ ID NO 408
```

```
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 408
ggaccuugca gcucgcaau                                                19

<210> SEQ ID NO 409
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 409
uauuuuaauc ggagagcaa                                                19

<210> SEQ ID NO 410
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 410
ucggagagca acuucaugu                                                19

<210> SEQ ID NO 411
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 411
cuucauguaa agauuucag                                                19

<210> SEQ ID NO 412
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 412
agauuucaga cuuggggcu                                                19

<210> SEQ ID NO 413
```

```
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 413
auuuacuccg cugauuacu                                                    19

<210> SEQ ID NO 414
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 414
guccuugcug cccauucgc                                                    19

<210> SEQ ID NO 415
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 415
gccaucaugu auggcaaau                                                    19

<210> SEQ ID NO 416
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 416
auucucuucu gauucagau                                                    19

<210> SEQ ID NO 417
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 417
ccaggaagug auugagaug                                                    19

<210> SEQ ID NO 418
```

```
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 418
gugauugaga uggugagaa                                                  19

<210> SEQ ID NO 419
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 419
aacggcagcu cuuaccaug                                                  19

<210> SEQ ID NO 420
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 420
cggcagcucu uaccaugcu                                                  19

<210> SEQ ID NO 421
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 421
gacugcccac ccagaaugu                                                  19

<210> SEQ ID NO 422
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 422
uguacagccu caugacaga                                                  19

<210> SEQ ID NO 423
```

```
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 423
ugagauuccu ucuaggaga                                                 19

<210> SEQ ID NO 424
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 424
gauuuaaaga uauucacgu                                                 19

<210> SEQ ID NO 425
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 425
agauauucac guccggcuu                                                 19

<210> SEQ ID NO 426
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 426
gucacacaag cucuacuac                                                 19

<210> SEQ ID NO 427
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 427
gcucuacuac uccuucagg                                                 19

<210> SEQ ID NO 428
```

```
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 428
augccaccac acagacaac                                                  19

<210> SEQ ID NO 429
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 429
ccucccucag ugccagccc                                                  19

<210> SEQ ID NO 430
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 430
ucucaguaac cccagauau                                                  19

<210> SEQ ID NO 431
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 431
ccccagauau ccuaauuac                                                  19

<210> SEQ ID NO 432
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 432
uuacauguuc ccgagccag                                                  19

<210> SEQ ID NO 433
```

```
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 433
uaccucagaa ccagcgauu                                                       19

<210> SEQ ID NO 434
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 434
ccagcgauuc auucccauc                                                       19

<210> SEQ ID NO 435
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 435
uggauaccca auaccuccu                                                       19

<210> SEQ ID NO 436
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 436
uaccuccugg auaugcagc                                                       19

<210> SEQ ID NO 437
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 437
cagguccucc cagagugau                                                       19

<210> SEQ ID NO 438
```

```
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 438
gagucggucc ccaagcagu                                                   19

<210> SEQ ID NO 439
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 439
gcagugccag ugggucgac                                                   19

<210> SEQ ID NO 440
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 440
ucaggaagca aauauuccu                                                   19

<210> SEQ ID NO 441
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 441
gcaaauauuc cuuuacuac                                                   19

<210> SEQ ID NO 442
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 442
auauuccuuu acuaccaca                                                   19

<210> SEQ ID NO 443
```

```
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 443
uuccaaauca uccuggugg                                                   19

<210> SEQ ID NO 444
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 444
aucauccugg uggaauggg                                                   19

<210> SEQ ID NO 445
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 445
uggguaucac cguuuuugg                                                   19

<210> SEQ ID NO 446
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 446
caaaucucaa aaacccuac                                                   19

<210> SEQ ID NO 447
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 447
aucucaaaaa cccuacaaa                                                   19

<210> SEQ ID NO 448
```

```
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 448
aaacccuaca aaauugacu                                                        19

<210> SEQ ID NO 449
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 449
acccuacaaa auugacuca                                                        19

<210> SEQ ID NO 450
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 450
aauugacuca aagcaagca                                                        19

<210> SEQ ID NO 451
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 451
uugacucaaa gcaagcauc                                                        19

<210> SEQ ID NO 452
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 452
agcaagcauc uuuacuagg                                                        19

<210> SEQ ID NO 453
```

```
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 453
gcaucuuuac uaggagacg                                                   19

<210> SEQ ID NO 454
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 454
uauucaugga cacaccgaa                                                   19

<210> SEQ ID NO 455
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 455
ucuaugauuu cugcagaac                                                   19

<210> SEQ ID NO 456
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 456
cuguaaaaug cacaacuuu                                                   19

<210> SEQ ID NO 457
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 457
aaugcacaac uuuuguaaa                                                   19

<210> SEQ ID NO 458
```

```
<210> SEQ ID NO 458
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 458
ugcacaacuu uuguaaaug                                               19

<210> SEQ ID NO 459
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 459
cuuuuguaaa ugugguaua                                               19

<210> SEQ ID NO 460
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 460
augugguaua caggacaaa                                               19

<210> SEQ ID NO 461
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 461
acuagacggc cguagaaaa                                               19

<210> SEQ ID NO 462
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 462
aagauuuaua uucaaaugu                                               19

<210> SEQ ID NO 463
```

```
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 463
gauuuauauu caaauguuu                                                  19

<210> SEQ ID NO 464
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 464
auguuuuuau uaaaguaag                                                  19

<210> SEQ ID NO 465
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 465
aguaagguuc ucauuuagc                                                  19

<210> SEQ ID NO 466
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 466
gguucucauu uagcagaca                                                  19

<210> SEQ ID NO 467
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 467
caaguaccuu cugugaagu                                                  19

<210> SEQ ID NO 468
```

```
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 468
guaccuucug ugaaguuuc                                                  19

<210> SEQ ID NO 469
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 469
guuucacugu gucuuacca                                                  19

<210> SEQ ID NO 470
<211> LENGTH: 19
<212> TYPE: DNA
<213> ORGANISM: Artificial
<220> FEATURE:
<223> OTHER INFORMATION: an artificially synthesized oligonucleotide for
      siRNA
<220> FEATURE:
<221> NAME/KEY: misc_feature
<223> OTHER INFORMATION: DNA/RNA

<400> SEQUENCE: 470
gcaggacaga cacucggcc                                                  19

<210> SEQ ID NO 471
<211> LENGTH: 21
<212> TYPE: DNA
<213> ORGANISM: Artificial
<220> FEATURE:
<223> OTHER INFORMATION: An artificially synthesized target sequence for
      siRNA

<400> SEQUENCE: 471
cagcaatgga cggaatttca a                                               21
```

CELL PROLIFERATION INHIBITOR

RELATED APPLICATIONS

This application is a 35 U.S.C. §371 national stage filing of PCT Application No. PCT/JP2009/062975 filed on Jul. 17, 2009, which claims priority to, and the benefit of, Japanese Patent Application No. 2008-187857 filed on Jul. 18, 2008. The contents of the aforementioned applications are hereby incorporated by reference.

TECHNICAL FIELD

The present invention relates to cell growth inhibitors.

BACKGROUND ART

There is no longer any doubt that the system of cellular canceration is an oncogenic mechanism/process induced by abnormalities in signal transduction mechanisms. In recent years, a new concept has been proposed, in which sustention of a signal associated with the differentiation process of a specific cell lineage is involved in the oncogenic process by serving as a lineage-specific survival signal. The concept has drawn great attention as it contributes to the elucidation of tissue-specific oncogenic mechanism.

The present inventors reported for the first time in the world that while the thyroid transcription factor-1 (TTF-1) gene, which is involved in peripheral lung differentiation, contributes as a master regulatory factor of cell differentiation. Its persistent expression is essential for the survival of pulmonary adenocarcinoma, and it is closely involved in the development and progression of cancer (Non-patent Document 1).

PRIOR ART DOCUMENTS

Patent Documents

[Patent Document 1] WO2007/146957

Non-Patent Documents

[Non-patent Document 1] Tanaka H., et al., Cancer Res. 67: 6007-6011, 2007
[Non-patent Document 2] MacKeigan J P, et al., Nat. Cell Biol. 7: 591-600, 2005

DISCLOSURE OF THE INVENTION

Problems to be Solved by the Invention

The present invention provides nucleic acids that inhibit the expression of an ROR1 gene and uses thereof. More specifically, the present invention provides cell growth inhibitors and pharmaceutical agents for treating and/or preventing cancer, all of which comprise nucleic acids that inhibit the ROR1 gene expression. The present invention also provides methods of screening for cell growth inhibitors.

Means for Solving the Problems

The present inventors revealed the TTF-1-specific oncogenic process by elucidating molecular mechanisms regulated by the master regulatory factor TTF-1. Thus, the present inventors focused on elucidation of the identity of the lineage-specific survival signal as a novel canceration signal.

The present inventors revealed that the master regulatory factor TTF-1, which is closely involved in the development and progression of pulmonary adenocarcinoma, induced the expression of the receptor tyrosine kinase ROR1 (receptor tyrosine kinase-like orphan receptor 1) gene, and that the growth of cancer cells of specific lineages could be inhibited by inhibiting the ROR1 gene expression. The present invention is based on these findings.

More specifically, the present invention provides the following:

[1] a composition for inhibiting cell growth, which comprises a nucleic acid that inhibits ROR1 gene expression;
[2] the composition of [1], wherein the nucleic acid that inhibits ROR1 gene expression is an siRNA, a vector that expresses an siRNA, an antisense RNA, a vector that expresses an antisense RNA, an antisense DNA, a ribozyme, or a vector that expresses a ribozyme;
[3] the composition of [2], wherein the siRNA comprises a sense-strand RNA from any region of an mRNA of the ROR1 gene, and an antisense-strand RNA of the sense-strand RNA;
[4] the composition of [1], wherein the cell is a cancer cell;
[5] the composition of [1], wherein the cell is a lung cancer cell, a pulmonary adenocarcinoma cell, a mesothelioma cell, a pancreatic cancer cell, or an osteosarcoma cell;
[6] a method of screening for a candidate compound having cell growth inhibitory activity, which comprises the steps of:
(1) contacting an ROR1 protein with a test compound;
(2) measuring the level of binding between the ROR1 protein and the test compound; and
(3) selecting a test compound that binds to the ROR1 protein;
[7] a method of screening for a candidate compound having cell growth inhibitory activity, which comprises the steps of:
(1) contacting a test compound with a cell expressing the ROR1 gene or an extract of the cell;
(2) determining the expression level of the ROR1 gene; and
(3) selecting a test compound that reduces the expression level of the ROR1 gene in the presence of the test compound compared to in the absence of the test compound;
[8] a method of screening for a candidate compound having cell growth inhibitory activity, which comprises the steps of:
(1) contacting a test compound with a cell into which a vector carrying a transcription regulatory region of the ROR1 gene and a reporter gene expressed under the control of the transcription regulatory region is introduced, or an extract of the cell;
(2) determining the expression level of the reporter gene; and
(3) selecting a test compound that reduces the expression level of the reporter gene in the presence of the test compound compared to in the absence of the test compound;
[9] a method of screening for a compound having cell growth inhibitory activity, which comprises the steps of:
(1) contacting a test compound with a cell expressing the ROR1 gene;
(2) measuring the level of cell growth; and
(3) selecting a test compound that reduces the level of cell growth in the presence of the test compound compared to in the absence of the test compound;
[10] a composition for treating or preventing cancer, which comprises a nucleic acid that inhibits ROR1 gene expression;
[11] the composition of [10], wherein the cancer is lung cancer, pulmonary adenocarcinoma, mesothelioma, pancreatic cancer, or osteosarcoma;
[12] a method for treating or preventing cancer, which comprises the step of administering to a subject a nucleic acid that inhibits ROR1 gene expression;

[13] the method of [12], wherein the cancer is lung cancer, pulmonary adenocarcinoma, mesothelioma, pancreatic cancer, or osteosarcoma;

[14] use of a nucleic acid that inhibits ROR1 gene expression in the production of a composition for treating or preventing cancer;

[15] the use of [14], wherein the cancer is lung cancer, pulmonary adenocarcinoma, mesothelioma, pancreatic cancer, or osteosarcoma;

[16] a nucleic acid that inhibits ROR1 gene expression for use in a method for treating or preventing cancer; and

[17] the nucleic acid of [16], wherein the cancer is lung cancer, pulmonary adenocarcinoma, mesothelioma, pancreatic cancer, or osteosarcoma.

MODE FOR CARRYING OUT THE INVENTION

Figure 1:
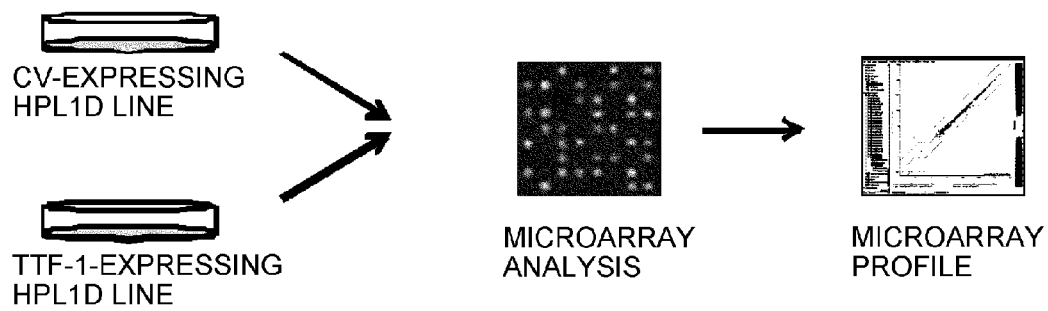
FIG. 1 shows in diagrams and a photograph microarray analysis of TTF-1 expression. Microarray analysis was carried out to identify target genes downstream of TTF-1. As a result, the gene expression of receptor tyrosine kinase-like orphan receptor 1 (ROR1) was identified to be increased five or more times in HPL1D-TTF-1 as compared to HPL1D-CV.

The present invention provides compositions for inhibiting cell growth, which comprise nucleic acids that inhibit the expression of an ROR1 gene. The compositions are used, for example, as pharmaceutical compositions or reagent compositions. Alternatively, the compositions can be used as experiment and research compositions for elucidating physiological conditions associated with the ROR1 gene.

Information of the human ROR1 gene as well as the cDNA and amino acid sequences are known. It is possible to use, for example, the gene information of GenBank Gene ID: 4919, cDNA and amino acid sequences available under GenBank accession Nos. NM_005012 and NP_005003, respectively. The cDNA and amino acid sequences of human ROR1 are shown in SEQ ID NOs: 1 and 2, respectively. Furthermore, a cDNA sequence comprising 1,000 bp of the promoter region is shown in SEQ ID NO: 3.

Herein, the "inhibition of the ROR1 gene expression" includes inhibition of both gene transcription and protein translation. The inhibition includes not only complete loss of DNA expression but also decreased DNA expression.

Oligonucleotides to be formulated into compositions of the present invention include DNAs, RNAs, and DNA-RNA chimeric molecules. Furthermore, DNA/RNA hybridized molecules, and DNAs and RNAs comprising nucleotide derivatives are also included in the oligonucleotides of the present invention. Known oligonucleotides include, for example, oligonucleotides modified at their ends to be conferred with nuclease resistance. Oligonucleotides introduced with fluorescent molecules are also known. Such artificially synthesized oligonucleotides are also included in the oligonucleotides of the present invention.

For example, RNAs are preferable oligonucleotides to be formulated into compositions of the present invention. The RNAs include not only ribonucleic acids that constitute natural RNAs but also those with substitution of artificial bases and derivatives thereof. Thus, RNAs comprising inosines (i) instead of the natural bases a, u, c, and g can be used to form complex. Alternatively, there are known methods for artificially synthesizing nucleic acid derivatives in which the phosphate linkages are replaced with thioate or boranophosphate linkages. It is also possible to modify the sugar structure of ribonucleic acids. The 2'-O-methyl modification, 2'-fluoro modification, locked nucleic acid (LNA) modification, or such may be used as a method for modifying the sugar structure. DNA-RNA chimeric molecules which are partially introduced with DNA are also known.

RNAs have been revealed to have various functions. For example, the RNAi effect and antisense effect are the effects of RNAs comprising a nucleotide sequence complementary to a gene to inhibit expression of the gene. Ribozymes of various structures are also known to suppress gene expression in cells. Any of such RNAs having the activity of suppressing gene expression can be used in the present invention. Furthermore, RNAs having specific nucleotide sequences are known to specifically bind to macromolecular compounds such as proteins. An RNA having the binding activity to substances other than nucleic acids is referred to as an aptamer. Some aptamers have the effect of regulating the activity of a protein by binding to it. RNAs that function as an aptamer can be used in the present invention.

In particular, such RNAs having a function other than transmission of the genetic code are sometimes referred to herein as functional RNAs. Herein, "functional RNA" refers to an RNA having a function other than translating the genetic code into an amino acid sequence. The function of translating the genetic code includes transcription of a DNA nucleotide sequence and transfer of amino acids. Accordingly, for example, RNAs having the functions described below are included in the functional RNAs:
Nucleic acid cleavage
Protein synthesis inhibition
Binding to substances other than nucleic acids The function of translating the genetic code in cells is generally supported by mRNAs and tRNAs. Herein, RNAs having the same nucleotide sequence as that of an mRNA or tRNA are also included in the functional RNAs as long as they have a function other than translation. Such functional RNAs can be synthesized by linking downstream of an appropriate promoter a DNA encoding the nucleotide sequence of RNA of interest and transcribing it with an RNA polymerase. The RNAs may be transcribed in cells or synthesized by in vitro transcription in an adequate environment. A transcription termination signal can be preferably positioned at the 3' end of the coding sequence of a DNA that serves as a template. Various functional RNAs are described more specifically below.

RNA Having RNAi Effect:

In an embodiment of the present invention, the functional RNAs are dsRNAs that are complementary to the transcripts of the endogenous ROR1 gene. RNA interference (RNAi) is a phenomenon where the expression of a target gene is suppressed by inducing destruction of the target gene mRNA when a double-stranded RNA (hereinafter abbreviated as dsRNA) having a sequence identical or similar to the target gene sequence is introduced into cells.

When about 40 to a few hundred base pairs of dsRNAs are introduced into cells, an RNaseIII-like nuclease called Dicer, which has a helicase domain, processes the dsRNAs from their 3' end into about 21 to 23 base pairs to produce short interference RNAs (siRNAs) in the presence of ATP. Specific proteins bind to the siRNAs to form nuclease complexes (RNA-induced silencing complexes (RISC)). The complexes recognize and bind to the same sequence as siRNA, and then cleave the mRNA of a target gene at the center of the siRNA by RNaseIII-like enzymatic activity. In another pathway, the antisense strand of siRNA binds to mRNA and serves as a primer for RNA-dependent RNA polymerase (RsRP) to synthesize dsRNA. A pathway is considered in which this dsRNA serves again as a substrate of Dicer, produces a new siRNA, and amplifies its effect.

An siRNA may be used as dsRNA for RNAi of the present invention. "siRNA" refers to a double-stranded RNA consisted of short strands within a non-cytotoxic range. In 1999, Tuschl et al. reported that the efficiency of siRNA in suppressing expression depends on the length of the dimer and such (Tuschl T., et al., Genes Dev. 13: 3191-3197, 1999). According to the report by Tuschl et al., the adequate length of siRNA is about 19 to 23 bases for a short chain RNA or double-stranded RNA (dsRNA). Thereafter, a report of Bohula et al. describes that the activity remains the same for 19 to 27 bases (Bohula E A, et al., J. Biol. Chem. 278: 15991-15997, 2003). Thus, in producing the ROR1 siRNAs described in the Examples of the present invention, candidate ROR1 siRNAs were detected according to the conditions described by Tuschl et al. using two types of siRNA design databases [software] (RNAi Central (19 bases) and siRNA Target Finder (21 bases)) for designing siRNAs of about 19 to 23 bases.

However, even long RNAs that have no RNAi effect when intact can be degraded into siRNAs that have RNAi effect in cells; thus, the length of the double-stranded RNAs of the present invention is not particularly limited. For example, the length may be 15 to 49 base pairs, preferably 15 to 35 base pairs, and more preferably 21 to 30 base pairs. Alternatively, the final length of the double-stranded RNA portion that results from transcription of an expressed siRNA may be, for example, 15 to 49 base pairs, preferably 15 to 35 base pairs, and more preferably 21 to 30 base pairs.

Furthermore, a long double-stranded RNA corresponding to the full-length or nearly full-length mRNA of a target gene can be, for example, pre-digested with Dicer, and the resulting degradation products can be used as an RNA having RNAi effect. Such degradation products are expected to contain double-stranded RNA (siRNA) molecules with an RNAi effect. With this method, it is not necessary to specifically select the mRNA regions that have an expected RNAi effect.

In gene suppression experiments using RNAi, since gene suppression has to be achieved in a target gene-specific manner, it is important that the siRNA sequence is specific to the target gene (Jackson A L, et al., Nat. Biotechnol. 21: 635-637, 2003). Although it is not required for a DNA used for RNAi to be completely identical to a target gene, it has a sequence homology of at least 70% or more, preferably 80% or more, more preferably 90% or more, and most preferably 95% or more. The gene expression-suppression effect of an siRNA increases as the DNA homology increases. Thus, in producing the ROR1 siRNAs described in the Examples of the present invention, candidate functional ROR1 siRNAs were detected to be completely complementary to a target gene using two types of siRNA design databases [software] (RNAi Central and siRNA Target Finder).

The double-stranded RNA portion in a dsRNA, in which RNAs are paired, is not necessarily completely paired, but may have unpaired portions due to a mismatch (corresponding bases are not complementary), a bulge (there is no corresponding base on one strand) or the like. In the present invention, both bulges and mismatches may be included in double-stranded RNA regions where RNAs are paired with each other in dsRNAs.

Meanwhile, double-stranded RNAs having an overhang of several nucleotides at their ends are known to have a high RNAi effect. Accordingly, double-stranded RNAs having an RNAi effect preferably have an overhang of several nucleotides at the ends. The length of a nucleotide that forms the overhang is not particularly limited; however, the number of overhang nucleotides is preferably two nucleotides. A double-stranded RNA having an overhang of, for example, TT (a thymine doublet), UU (an uracil doublet), or some other nucleotides is preferred in the present invention. For example, it is believed that molecules that have a double-stranded RNA of 19 nucleotides and a two-nucleotide (TT) overhang produce high RNAi effects in human. Double-stranded RNAs having an RNAi effect also include chimeric molecules in which the overhanging nucleotides are DNAs.

Herein, the double-stranded RNA refers to an RNA having a structure where the complementary strands anneal with each other. Thus, as described above, when a single-stranded RNA comprises complementary nucleotide sequences that form a double-stranded structure by annealing to each other, it is also included in the double-stranded RNA. Specifically, single-stranded RNAs that form a stem-loop structure are included in the double-stranded RNA because they comprise a double-stranded structure (stem portion).

siRNAs are constructed so that a single transcript comprises both the sense sequence derived from a target gene and its complementary antisense sequence, for example, as a hairpin.

Loop sequences comprising an arbitrary nucleotide sequence can be positioned between a sense sequence and an antisense sequence to form a hairpin-loop structure. Thus, the present invention also provides siRNAs having a general formula of 5'-[A]-[B]-[A']-3', where [A] is a ribonucleotide sequence corresponding to a sequence that specifically hybridizes to ROR1 mRNA or cDNA. In a preferred embodiment, [A] represents a ribonucleotide sequence corresponding to the ROR1 gene sequence; [B] represents a ribonucleotide sequence of about 3 to 23 nucleotides; and [A'] represents a ribonucleotide sequence comprising a sequence complementary to [A]. Region [A] hybridizes to [A'], thereby forming a loop comprising region [B]. The loop sequence is preferably 3 to 23 nucleotides in length. The loop sequence is selected, for example, from the sequences described below (see www.ambion.com/techlib/tb/tb_506.html). In addition, loop sequences of 23 nucleotides also provide active siRNAs (Jacque, J. M. et al., Nature 418: 435-8, 2002).

CCC, CCACC, and CCACACC (Jacque, J. M. et al., Nature, 418: 435-8, 2002)

UUCG (Lee, N. S. et al., Nature Biotechnology 20: 500-5, 2002; Fruscoloni, P. et al., Proc. Natl. Acad. Sci. USA 100: 1639-44, 2003)

UUCAAGAGA (Dykxhoorn, D. M. et al., Nature Reviews Molecular Cell Biology 4: 457-67, 2003).

Examples of preferred siRNAs of the present invention having a hairpin-loop structure are shown below. In some embodiments, loop sequence [B] can be selected from the group consisting of CCC, UUCG, CCACC, CCACACC, and UUCAAGAGA. The preferred loop sequence is UUCAAGAGA (corresponding to "ttcaagaga" in DNA).

Those skilled in the art can appropriately design double-stranded RNAs having an RNAi effect against a target gene based on the nucleotide sequence of the target gene. Specifically, based on the nucleotide sequence of a target gene, those skilled in the art can select an arbitrary consecutive RNA region in an mRNA (a transcript of the nucleotide sequence) and prepare double-stranded RNA corresponding to the region. Methods for selecting an appropriate siRNA sequence having stronger RNAi effect from the mRNA sequence, which is a transcript of the nucleotide sequence, are also known in the art. Nucleotide sequences for siRNAs can be predicted, for example, according to a report of Reynolds et al. (Reynolds A. et al. Nature biotechnology 22: 326-330, 2004) or Ui-Tei et al. (Ui-Tei K. et al. Nucleic Acids Res. 32: 936-948, 2004).

siRNAs can also be designed based on partial nucleotide sequences of a gene. The nucleotide sequence of an arbitrary siRNA to be selected can be specified when the consecutive nucleotide sequence is known. The required length of nucleotide sequence is, for example, at least 20 to 30 nucleotides. In other words, siRNAs can also be designed against target genes whose sequences are not completely identified. Thus, when there are fragments of genes whose full length is not identified but have partially identified mRNAs, such as Expressed Sequence Tags (ESTs), double-stranded RNAs that suppress expression of the genes can also be produced based on the nucleotide sequences of the fragments.

Specifically, siRNAs of the present invention can be designed and produced by the method described below. Since information of the human ROR1 gene and its cDNA sequence are known, siRNAs can be designed, for example, based on information of the gene under GenBank Gene ID: 4919, and the nucleotide sequence deposited under GenBank accession number NM_005012 (the human ROR1 cDNA sequence is shown in SEQ ID NO: 1). The nucleotide sequence of ROR1 (NM_005012) available from GenBank is entered into each siRNA design database [software] (RNAi Central and siRNA Target Finder) (the accession number can also be entered) to design siRNAs against ROR1 according to their unique algorithms (siRNA design program). In the settings, the target region is specified to the Open Reading Frame (ORF) and the organism is specified to human to minimize cross inhibitory reaction against non-target genes. It is also possible to select the GC content in an siRNA of interest. The above-described series of settings enable one to find candidates for a high-efficiency siRNA with minimized off-target effect, which is efficiently incorporated into RNA-induced silencing complexes (RISC) (in the present invention, 293 and 174 sequences were found as candidates of siRNA against ROR1 by RNAi Central and siRNA Target Finder, respectively). At RNAi Central, the designed siRNAs are listed in descending order of inhibitory activity (in ascending order of off-target probability).

The two siRNA designing database systems described above are disclosed without cost to nonprofit research institutes. Thus, everyone can use the systems on internet web without limitation. The respective siRNA sequence-designing methods are known to those skilled in the art.

An RNA of the present invention can be expressed from an antisense DNA encoding an antisense RNA of any region in a target gene mRNA and a sense DNA encoding a sense RNA corresponding to the region in the target gene mRNA. Furthermore, a dsRNA can also be prepared from the antisense and sense RNAs.

When DNAs are inserted into vectors or the like to express a dsRNA of the present invention, the antisense strand RNA and sense strand RNA are both expressed from a single vector or individually from different vectors. For example, when both antisense-strand and sense-strand RNAs are expressed from a single vector, a construct can be prepared by separately constructing an expression cassette for the antisense-strand RNA and an expression cassette for the sense-strand RNA, where a promoter such as the polIII system which enables the expression of a short RNA is linked upstream of the antisense and sense DNAs, respectively, and then inserting these cassettes into a vector in the same or reverse orientation. Alternatively, the expression system may be constructed such that the antisense and sense DNAs are arranged on separate strands and in the opposite direction. This construct comprises a double-stranded DNA (siRNA-coding DNA) in which the antisense strand RNA-encoding strand and sense strand RNA-encoding strand are paired with each other, and promoters are positioned at both ends in the opposite direction, such that the antisense strand RNA or sense strand RNA can be expressed from each strand. In this case, it is preferred that a terminator is positioned at the 3' end of each strand (antisense-strand RNA-encoding strand or sense-strand RNA-encoding strand) to avoid addition of extra sequences downstream of the sense RNA and antisense RNA. A sequence of four or more consecutive adenine (A) nucleotides or the like may be used as the terminator. Furthermore, the two promoters are preferably different in this palindromic expression system.

Meanwhile, when the antisense-strand and sense-strand RNAs are expressed by separate vectors, constructs can be prepared, for example, by separately constructing an expression cassette for the antisense RNA and an expression cassette for the sense RNA, where a promoter such as the polIII system which enables the expression of a short RNA is linked upstream of the antisense DNA and sense DNA, respectively, and then inserting these cassettes into separate vectors.

The present invention provides cell growth inhibitors comprising nucleic acids that inhibit the ROR1 gene expression. The expression of ROR1 is inhibited, for example, by one or more short-interfering RNA (siRNA) oligonucleotides which specifically target the ROR1 gene. Such siRNAs include those having a sense-strand RNA from a region of an mRNA of the ROR1 gene, and an antisense-strand RNA for the sense-strand RNA. The target includes, for example, the nucleotides of SEQ ID NO: 1.

Specifically, siRNAs of the present invention include the siRNAs described in Example 8 (SEQ ID NOs: 4 to 471), preferably those described in SEQ ID NOs: 5, 6, and 471 (Example 9).

RNA Having Antisense Effect:

Functional RNAs of the present invention may be RNAs that have an antisense effect against some genes. Methods using antisense technologies are known as methods for inhibiting (suppressing) the expression of specific genes. The following multiple mechanisms are involved in the inhibition of the expression of target genes by antisense nucleic acids.

There are a number of factors that contribute to the action of antisense nucleic acids in inhibiting target gene expression, including inhibition of:

transcription initiation by triplex formation;
transcription by hybrid formation at a site with a local open-loop structure generated by an RNA polymerase;
transcription by hybrid formation with the RNA being synthesized;
splicing by hybrid formation at an intron-exon junction;
splicing by hybrid formation at the site of spliceosome formation;
transport from the nucleus to the cytoplasm by hybrid formation with mRNA;
splicing by hybrid formation at the capping site or poly(A) addition site;
translation initiation by hybrid formation at the translation initiation factor binding site;
translation by hybrid formation at the ribosome-binding site adjacent to the start codon;
peptide chain elongation by hybrid formation in the translational region of mRNA or at the polysome binding site of mRNA; and
gene expression by hybrid formation at the protein-nucleic acid interaction sites. These inhibit the expression of target genes by inhibiting the process of transcription, splicing, or translation (Hirashima and Inoue, "Shin Seikagaku Jikken-koza 2 (New Courses in Experimental Biochemistry 2), Kakusan IV (Nucleic Acids IV), Idenshi no Fuhusei to Hat-sugen (Gene Replication and Expression)", Ed. The Japanese Biochemical Society, Tokyo Kagaku Dojin Co., Ltd., pp. 319-347, 1993).

In the present invention, RNAs having an antisense effect include RNAs capable of inhibiting target gene expression through any one of the actions described above. In one embodiment, an antisense sequence designed to be complementary to an untranslated region adjacent to the 5' end of a target gene mRNA may be effective for inhibiting translation of the gene. Sequences complementary to a coding region or 3'-untranslated region can also be used. Thus, in the present invention RNAs having an antisense effect include not only RNAs comprising sequences antisense to the coding regions, but also RNAs comprising sequences antisense to untranslated regions of the target genes.

The antisense RNAs of the present invention can be synthesized by any method. Specifically, RNAs comprising a required nucleotide sequence can be obtained by transcription using RNA polymerase or chemical synthesis. When an antisense RNA is synthesized as a synthetic RNA oligomer, it can be prepared in a form of S oligo (phosphorothioate-type oligonucleotides) in which oxygen (O) is displaced with sulfur (S) at the phosphate ester linkage. Resistance to nuclease degradation can be conferred by synthesizing the RNA as an S oligo. Thus, the S oligos are preferable functional RNAs in the present invention.

It is preferred that an antisense RNA sequence is complementary to the target gene sequence or a portion thereof. However, as long as the antisense RNAs effectively suppress the target gene expression, it is not necessary for the nucleotide sequence to be perfectly complementary to the nucleotide sequence of the target gene. The transcribed RNA has preferably 90% or higher complementarity, and most preferably 95% or higher (for example, 95%, 96%, 97%, 98%, or 99% or higher) complementarity to the target gene transcript. The length of the antisense RNA used to effectively suppress the target gene expression is at least 15 nucleotides or more, preferably 100 nucleotides or more, and more preferably 500 nucleotides or more. The length of antisense DNA to be used is generally less than 5 kb, and preferably less than 2.5 kb.

RNAs Having Ribozyme Activity:

RNAs having ribozyme activity can be used as functional RNAs of the present invention. "Ribozyme" refers to an RNA molecule having catalytic activity. There are ribozymes with a variety of activities. For example, ribozymes having the activity of cleaving RNA in a site-specific manner can be designed. Ribozymes such as group I intron-type ribozymes and M1 RNA, which are RNase P ribozymes, are 400 nucleotides or more in length. Others such as hammerhead and hairpin ribozymes have active sites containing about 40 nucleotides (M. Koizumi and E. Otsuka, Tanpakushitsu Kakusan Koso (Protein, Nucleic acid, and Enzyme), 35: 2191, 1990).

For example, the self-cleaving domain of a hammerhead type ribozyme cleaves the sequence G13U14C15 at the 3' side of C15. Base pairing between U14 and A9 is important for ribozyme activity. It has been shown that the sequence can be cleaved when C15 is substituted with A15 or U15 (Koizumi M., et al., FEBS Lett. 228: 228-230, 1988). Restriction enzyme-like RNA-cleaving ribozymes that recognize the sequence UC, UU, or UA in target RNAs can be artificially created by designing their substrate-binding sites to be complementary to an RNA sequence adjacent to the target site (Koizumi et al., FEBS Lett. 239:285-288, 1988; Koizumi, M. and Ohtsuka, E., Tan pakushitsu Kakusan Koso (Protein, Nucleic Acid and Enzyme) 35: 2191, 1990; Koizumi et al., Nucleic Acids Res. 17: 7059-7071, 1989).

In addition, hairpin-type ribozymes are also useful in cleaving RNAs. A hairpin-type ribozyme is found in, for example, the minus strand of tobacco ringspot virus satellite RNA (Buzayan J M, Nature 323: 349-353, 1986). Target specific RNA-cleaving ribozymes can also be produced from hairpin ribozymes (Kikuchi Y., et al. Nucleic Acids Res, 19: 6751-6755, 1991; Kikuchi, H., Kagaku to Seibutsu (Chemistry and Biology), 30: 112, 1992). Thus, RNAs having a ribozyme activity that can specifically cleave target gene transcripts can also be designed and used in the present invention.

For nucleic acids that constitute compositions of the present invention, nucleic acids that have various functions can be used. Specifically, nucleic acids having the activity of modifying gene expression or protein function can be used in the present invention. Herein, a nucleic acid having the activity of modifying gene expression or protein function is referred to as a functional nucleic acid. When such a nucleic acid is a DNA or RNA, it is sometimes referred to as a functional DNA or functional RNA. In the present invention, functional nucleic acids can modify protein functions by regulating protein expression or protein activity by binding to the protein.

Compositions for inhibiting cell growth can be obtained by using functional nucleic acids as nucleic acids of the present invention. Specifically, the present invention relates to compositions for inhibiting cell growth, which comprise functional nucleic acids as an active ingredient. The present invention also relates to the use of functional nucleic acids in producing compositions for inhibiting cell growth.

The present inventors have revealed that the ROR1 gene is specifically expressed in cancer cells of particular lineages. Thus, cells whose growth is inhibited by compositions comprising functional nucleic acids of the present invention include cancer cells, preferably lung cancer (pulmonary adenocarcinoma) cells, mesothelioma cells, pancreatic cancer cells, and osteosarcoma cells. Such cells include cells in the body of a subject organism (including humans) and cells of cell lines established as stable, uniform cells; however, they are not limited to these examples.

The more preferred cells of the present invention include various TTF-1$^-$ROR1$^+$ cancer cells such as some lung cancer (squamous cell carcinoma, large cell carcinoma, and small cell carcinoma) cells, cells of mesothelioma and pancreatic cancers which are intractable cancers, and osteosarcoma cells as well as colorectal adenocarcinoma cells as listed in Table 2. The most preferable cells of the present invention include lung cancer cells, in particular, TTF-1$^+$ROR1$^+$ pulmonary adenocarcinoma cells, to which the ROR1 siRNA compositions produce a maximum cell growth suppression effect.

As described below in the Examples (in particular, FIGS. 9 and 14), the cell growth-suppressing effect of ROR1 siRNA compositions is more significant in TTF-1$^+$ROR1$^+$ cell populations than in TTF-1$^-$ROR1$^+$ cell populations. This suggests that a stronger effect is produced by specifically suppressing the function of ROR1 which is under the control of TTF-1. Thus, the effect is exerted in a TTF-1$^+$ROR1$^+$-specific manner.

Meanwhile, cells not affected by the cell growth suppression effect of the ROR1 siRNA compositions of the present invention include normal cells such as bronchial epithelial cells, epithelial cells of peripheral trachea, mesothelial cells, and embryonic renal cells.

Herein, TTF-1$^+$ROR1$^+$ refers to cells expressing both TTF-1 and ROR1, while TTF-1$^-$ROR1$^+$ refers to cells expressing ROR1 but not TTF-1 (see for details in Example 7 and Table 2).

The present invention relates to compositions for treating or preventing cancer, which comprise nucleic acids that inhibit the ROR1 gene expression. The present invention also relates to methods for treating or preventing cancer, which comprise the step of administering a nucleic acid that inhibits the ROR1 gene expression to subjects.

Furthermore, the present invention relates to the use of nucleic acids that inhibit the ROR1 gene expression in producing compositions for treating or preventing cancer. The present invention also relates to nucleic acids that inhibit the ROR1 gene expression for use in methods for treating or preventing cancer.

When a functional nucleic acid of the present invention is used as a gene therapy agent, a composition comprising functional nucleic acids of the present invention may be directly administered to subjects by injection. Alternatively, it is possible to administer a vector inserted with the nucleic acids to subjects. Such vectors include adenovirus vectors, adeno-associated virus vectors, herpes virus vectors, vaccinia virus vectors, retroviral vectors, and lentiviral vectors. The functional nucleic acids can be efficiently administered by using these vectors.

Alternatively, the functional nucleic acids of the present invention can be encapsulated into phospholipid vesicles such as liposomes, and then the vesicles can be administered to subjects. Vesicles carrying siRNAs or shRNAs are introduced into given cells by lipofection. The resulting cells are then systemically administered, for example, intravenously or intra-arterially. The cells can also be locally administered to cancer tissues or such. siRNAs exhibit a quite superior and specific post-transcriptional suppression effect in vitro; however, duration is limited because they are rapidly degraded in vivo due to serum nuclease activity. Thus, there is a demand for development of optimized and effective delivery systems. For example, Ochiya et al. have reported that atelocollagen, a bio-affinity material, is a highly suitable siRNA carrier because it has the activity of protecting nucleic acids from nucleases in the body when mixed with the nucleic acids to form a complex (Ochiya, T. et al., Nat. Med. 5: 707-710, 1999; Ochiya, T. et al., Curr. Gene Ther. 1: 31-52, 2001). However, the methods for introducing pharmaceutical agents of the present invention are not limited thereto.

The pharmaceutical agents of the present invention are administered to mammals including humans at required (effective) doses within a dose range that is considered safe. Ultimately, the doses of the agents of the present invention can be appropriately determined by medical practitioners or veterinarians after considering the dosage form and administration method, and the patient's age and weight, symptoms, and the like. For example, adenoviruses are administered once a day at a dose of about $10^6$ to $10^{13}$ virions every one to eight weeks, although the doses vary depending on the age, sex, symptoms, administration route, administration frequency, and dosage form.

Commercially available gene delivery kits (for example, AdenoExpress™; Clontech) may be used to introduce siRNAs or shRNAs into target tissues or organs.

The present inventors revealed that cancer cell growth was inhibited by suppressing the ROR1 gene expression. This result suggests that candidate compounds that have cell growth inhibitory activity can be screened.

The test compounds to be used in the screening methods of the present invention are not particularly limited, and include, for example, single compounds such as natural compounds, organic compounds, inorganic compounds, proteins, antibodies, and peptides; and compound libraries, expression products of gene libraries, cell extracts, cell culture supernatants, products of fermenting microorganisms, extracts of marine organisms, and plant extracts.

The first embodiment of the screening methods of the present invention relates to screening for compounds that bind to ROR1 proteins or fragments thereof. In this screening, a ROR1 protein or a fragment thereof is first contacted with a test compound. Then, binding between the test compound and ROR1 protein or fragment thereof is detected. Next, the test compound that binds to the ROR1 protein or fragment thereof is selected. Compounds isolated by this method can be candidate compounds of cell growth inhibitors. The compounds can also be used as test compounds in the screening methods described below.

Many methods known to those skilled in the art can be used as methods of using ROR1 proteins to screen for proteins that bind to ROR1 proteins. Such screening can be carried out, for example, using the method by Skolnik et al. (Skolnik E Y, et al., Cell 65: 83-90, 1991). More specifically, cDNA libraries using phage vectors (λgt11, ZAP, etc.) are prepared from cells or tissues expressing proteins predicted to bind to ROR1 proteins or fragments thereof and they are expressed on LB-agarose, and the expressed proteins or fragments thereof are immobilized onto filters. The filters are incubated with purified and labeled ROR1 proteins or fragments thereof, and plaques expressing proteins bound to ROR1 proteins or fragments thereof can be detected using a label. Methods for labeling ROR1 proteins or fragments thereof include: methods using the binding between biotin and avidin; methods using antibodies that specifically bind to ROR1 proteins or fragments thereof, or proteins fused with ROR1 proteins or fragments thereof (for example, GST); methods using radio-isotopes; and methods using fluorescence.

Alternatively, the first embodiment of the screening methods of the present invention includes methods using the two-hybrid system using cells (Fields S and Sternglanz R, Trends. Genet. 10: 286-292, 1994; Dalton S and Treisman R, "Characterization of SAP-1, a protein recruited by serum response factor to the c-fos serum response element", Cell 68: 597-612, 1992; "Matchmarker Two-Hybrid System", "Mammalian Matchmarker Two-Hybrid Assay Kit", "Matchmarker One-Hybrid System" (all from Clontech), "HybriZAP Two-Hybrid Vector System" (Stratagene)).

In the two-hybrid system, an ROR1 protein or fragment thereof (partial peptide) is fused with a DNA-binding region of SRF or a DNA-binding region of GAL4, and is expressed in yeast cells. A library of cDNAs designed to express fusion proteins with a VP16 or GAL4 transcription activation region is prepared from cells that are predicted to express proteins that bind to an ROR1 protein or fragment thereof; the library is introduced into the yeast cells; and cDNAs derived from the library are isolated from the positive clones detected (when a protein that binds to an ROR1 protein is expressed in yeast cells, the reporter gene is activated by the binding of these two, and positive clones can be confirmed based on the binding). Proteins encoded by the cDNAs can be obtained by introducing the isolated cDNAs and expressing them in *E. coli*. Thus, proteins that bind to ROR1 proteins, or their genes, can be prepared.

Reporter genes used in the two-hybrid system include, for example, the HIS3 gene, Ade2 gene, LacZ gene, CAT gene, luciferase gene, and plasminogen activator inhibitor type 1 (PAI-1) gene, but are not limited thereto. Screening by the two-hybrid method can be carried out using mammalian cells or such other than yeast.

Screening of compounds that bind to ROR1 proteins or fragments thereof can also be carried out using affinity chromatography. For example, ROR1 proteins or fragments thereof are immobilized to carriers on an affinity column, and test compounds that are predicted to express proteins that bind to ROR1 proteins or fragments thereof are applied onto the column. Such test compounds include, for example, cell extracts and cell lysates. After the test compounds are applied, the column is washed to obtain proteins bound to ROR1 proteins or fragments thereof.

DNAs encoding the proteins can be obtained by analyzing the amino acid sequences of the obtained proteins, synthesizing oligo DNAs based on these sequences, and screening cDNA libraries using these DNAs as probes.

Methods for isolating not just proteins but compounds that bind to ROR1 proteins or fragments thereof include, for example, methods in which synthetic compounds, natural product banks, or random phage peptide display libraries are reacted with immobilized ROR1 proteins or fragments thereof and then molecules that bind to the ROR1 proteins or fragments thereof are screened, and high-throughput screening methods using combinatorial chemistry technology (Wrighton N C; Farrell F X; Chang R; Kashyap A K; Barbone F P; Mulcahy L S; Johnson D L; Barrett R W; Jolliffe L K; Dower W J, Small peptides as potent mimetics of the protein hormone erythropoietin, Science 273: 458-64, 1996; Verdine G L, The combinatorial chemistry of nature. Nature 384: 11-13, 1996; Hogan J C Jr., Directed combinatorial chemistry. Nature 384: 17-9, 1996). These methods are known to those skilled in the art.

In the present invention, biosensors using the surface plasmon resonance phenomenon can also be used as a means for measuring or detecting bound compounds. Biosensors using the surface plasmon resonance phenomenon enable real-time observation of interactions between test compounds and ROR1 proteins or fragments thereof as surface plasmon resonance signals, by using trace amounts of proteins without labeling (for example, BIAcore; Pharmacia).

The second embodiment of the screening methods of the present invention relates to screening for compounds that reduce the expression level of DNAs encoding ROR1 proteins. Compounds that reduce the expression level of DNA encoding an ROR1 protein can be candidates for compounds having cell growth inhibitory activity.

In this screening, first, the test compounds are contacted with cells (including human cells) or extracts thereof comprising DNA encoding an ROR1 protein. Such cells (including human cells) comprising DNA encoding an ROR1 protein include, for example, COS cells, HEK293T cells, mouse Balb cells, cells stably expressing ROR1, and cancer patient-derived cells.

Meanwhile, in the present invention, "contact" can be carried out, for example, by adding test compounds to cell culture media. In this screening, the expression level of DNA encoding a ROR1 protein in the cells are then determined and compounds that reduce the DNA expression level compared to when the DNA is not contacted with the test compounds are selected.

The DNA expression level can be determined by methods known to those skilled in the art. For example, DNA expression levels can be measured by extracting mRNAs according to conventional methods, and carrying out a Northern hybridization method or RT-PCR method using these mRNAs as templates. Additionally, DNA array technologies can be used to determine the DNA expression levels. Alternatively, the translation level of the genes can be determined by collecting fractions comprising an ROR1 protein using conventional methods and detecting the expression of ROR1 protein by electrophoresis such as SDS-PAGE. The translation level of the genes can also be determined by performing Western blotting, dot blotting, immunoprecipitation, enzyme-linked immunosorbent assay (ELISA), immunofluorescence, and such using antibodies against ROR1 proteins to detect the ROR1 protein expression.

In the third embodiment of screening methods of the present invention, reporter gene systems can be used to screen for compounds that reduce the level of ROR1 gene expression. First, cells or cell extracts comprising DNAs in which a reporter gene is operably linked downstream of the ROR1 gene promoter region is provided. Herein, "operably linked" means that the reporter gene is linked to the ROR1 gene promoter region so that the reporter gene expression is induced by binding transcription factors to the ROR1 gene promoter region. Thus, even cases where a reporter gene is linked to a different gene and therefore forms a fusion protein with the gene product are included in the above meaning of "operably linked", as long as the fusion protein expression is induced by binding transcription factors to the ROR1 gene promoter region.

The ROR1 gene promoter region includes, for example, a region comprising the nucleotide sequence of positions 1 to 1,000 in SEQ ID NO: 3.

The above-described reporter genes are not particularly limited as long as their expression is detectable, and include, for example, the CAT gene, lacZ gene, luciferase gene, β-glucuronidase gene (GUS), and GFP gene, which are generally used by those skilled in the art.

In this screening, test compounds are then contacted with the cells or cell extracts described above. Next, the expression levels of the above reporter genes in the cells or cell extracts are measured. The expression level of a reporter gene can be measured by methods known to those skilled in the art depending on the type of the reporter gene used. For example, when the reporter gene is a CAT gene, the expression level of the reporter gene can be measured by detecting chloramphenicol acetylation by the gene product. When the reporter gene is a lacZ gene, the expression level of the reporter gene can be measured by detecting the color development of a chromogenic compound due to the catalytic action of the gene expression product. Alternatively, when the reporter gene is a luciferase gene, the expression level of the reporter gene can be measured by detecting the fluorescence of fluorogenic compounds due to the catalytic action of the gene expression product. Furthermore, when the reporter gene is a β-glucuronidase gene (GUS), the expression level of the reporter gene can be measured by detecting the luminescence of Glucuron (ICN) or color development of 5-bromo-4-chloro-3-indolyl-β-glucuronide (X-Gluc) due to the catalytic effect of the gene expression product. In addition, when the reporter gene is a GFP gene, the expression level of the reporter gene can be measured by detecting the fluorescence of the GFP protein.

In this screening, compounds that reduce the expression level of the reporter gene as compared to when the test compounds are not contacted are then selected.

The fourth embodiment of screening methods of the present invention relates to screening for compounds that reduce the growth level of cells expressing the ROR1 gene. Compounds that reduce the growth level of cells expressing the ROR1 gene can be candidate compounds having cell growth inhibitory activity.

In this screening, test compounds are first contacted with cells (including human cells) comprising DNA encoding an ROR1 protein. The cells expressing the ROR1 gene may be cells that naturally express the ROR1 gene or cells that are artificially forced to express the ROR1 gene. The "contact" between cells and test compounds can be carried out by the method described above.

In this screening, the growth level of the cells is then determined to select compounds that inhibit the growth of the cells as compared to when the test compounds are not in contact. The cell growth level can be determined by methods known to those skilled in the art.

All prior art documents cited herein are incorporated herein by reference.

EXAMPLES

Hereinbelow, the present invention will be described more specifically with reference to the Examples; however, it is not to be construed as being limited thereto.

Example 1

Microarray-Based Identification of the ROR1 Gene Induced by TTF-1

TTF-1 Expression in HPL1D Cells, RNA Preparation, and Microarray Analysis

TTF-1 (pCMV-puro-TTF-1) was transfected into cells of the human normal peripheral lung cell-derived cell line HPL1D (hereinafter, HPL1D-TTF-1), and the cells were forced to express TTF-1. The HPL1D line into which an empty vector (pCMV-puro-control vector) was introduced was used as a control (hereinafter, HPL1D-CV). After introduction of TTF-1 or the empty vector, selection was carried out using puromycin (1.5 µg/ml). After three days, the cells were collected and total RNAs were extracted using an RNeasy kit (Qiagen), and this was treated with DNase I. The RNA quantity was determined using the NanoDrop ND-1000UV-Vis spectrophotometer (NanoDrop Technologies). The RNA quality was assessed using the Agilent 2100 bioanalyzer (Agilent). 500 ng of total RNAs extracted from the cells was labeled using a Low RNA Fluorescent Linear Amplification kit (Agilent Technologies, Paloalto, Calif.) to prepare Cy3- or Cy5-labeled cRNAs. More specifically, double-stranded cDNAs were synthesized using Moloney mouse leukemia virus reverse transcriptase and a poly dT primer containing the T7 promoter, and then Cy3- or Cy5-labeled cRNAs were prepared using T7 RNA polymerase and Cy3 or Cy5. Comprehensive expression analysis of the HPL1D-TTF-1 and HPL1D-CV strains was carried out using a microarray with 41,000 probes (Whole Human Genome; Agilent). The cRNAs were hybridized with the microarray. After washing, the microarray slide was scanned using the G2505B microarray scanner (Agilent). Expression data was obtained using the Feature Extraction 9.5.1 software (Agilent). ROR1 was identified as a gene whose expression level was five or more times higher in HPL1D-TTF-1 than in HPL1D-CV.

Results and Discussion (FIG. 1)

Microarray analysis was carried out to identify target genes (target molecules) downstream of TTF-1. As a result, eight gene groups that show three or more times higher expression in HPL1D-TTF-1 than in HPL1D-CV were identified. From them, receptor tyrosine kinase-like orphan receptor 1 (ROR1) was identified as a gene that shows five-fold or more changes (increases) in expression (Table 1). This result suggests the possibility that ROR1, a receptor tyrosine kinase, is a downstream target gene of TTF-1.

TABLE 1

| Fold-change | Gene Name | Description | Probe Name | Ref. Seq. |
|---|---|---|---|---|
| 5.30 | ROR1 | receptor tyrosine kinase-like orphan receptor 1 | A_23_P12363 | NM_005012 |

Example 2

Induction of ROR1 Expression by TTF-1

TTF-1 Expression in HPL1D Cells, cDNA Preparation, Real-Time PCR, and Western Blotting Cells of the human normal peripheral lung cell line HPL1D were forced to express TTF-1 (HIPL1D-TTF-1) or the empty vector (HPL1D-CV). After introduction of TTF-1 or the empty vector, selection was carried out using puromycin (1.5 µg/ml). After three days, the cells were collected and total RNAs were extracted using an RNeasy kit (Qiagen), and this was treated with DNase I. Then, cDNAs were prepared using random primers with Super Script II reverse transcriptase (Invitrogen). Meanwhile, aliquots of the collected cells were treated with SDS sample buffer to prepare lysates. Likewise, cDNAs and lysates were also prepared from the strains stably expressing TTF-1 (HPL1D-TTF-1 stable) and the empty vector (HPL1D-CV stable), which were established by the present inventors. ROR1 primers were designed using Primer 3 software (primer designing software, primer3.sourceforge.net). Using the ΔΔCT method, the expression level ratio relative to the level in HPL1D cells without expression was calculated (in triplicate) from the actual values determined for the cDNAs by real-time PCR (ribosome 18S was selected as an internal standard). The lysates were subjected to SDS-PAGE, and Western blotting using an anti-ROR1 antibody (Cell signaling) and an anti-TTF-1 antibody (WAKO).

Results and Discussion

Figure 2:
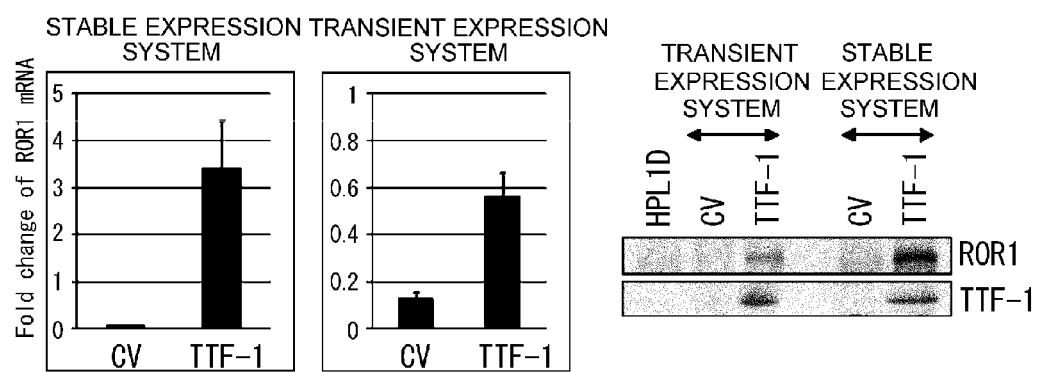
FIG. 2 shows in graphs and a photograph the induction of ROR1 expression by TTF-1. The change in ROR1 expression as a result of TTF-1 expression was analyzed at the mRNA and protein levels by real-time PCR or Western blotting, respectively. The result showed that the level of ROR1 expression was significantly increased in HPL1D-TTF-1 as compared to HPL1D-CV both in the transient TTF-1 expression system and stable TTF-1 expression system established by the present inventors. This result showed that ROR1 expression (at both mRNA and protein levels) was specifically induced by TTF-1 expression.

Changes in the ROR1 expression as a result of TTF-1 expression were evaluated at the mRNA level by real-time PCR. The result showed that the ROR1 expression level was significantly increased in HPL1D-TTF-1 compared to HPL1D-CV, both in the transient TTF-1 expression system and in the stable TTF-1 expression system established by the present inventors (left panel of FIG. 2).

The level of ROR1 mRNA expression was increased about six-fold in the transient TTF-1 expression system, and about 34-fold in the stable TTF-1 expression system.

Changes in the ROR1 expression as a result of TTF-1 expression were assessed also at the protein level by Western blotting. As a result, ROR1 expression was detected at the protein level in HPL1D-TTF-1 but not in HPL1D-CV, both in the transient TTF-1 expression system and in the stable TTF-1 expression system (ROR1 is not originally expressed in cells of the human normal peripheral lung cell-derived cell line HPL1D, and also no ROR1 expression is detected in HPL1D-CV; right panel of FIG. 2).

The results of real-time PCR and Western blotting showed that ROR1 expression (at both the mRNA and protein levels) is specifically induced by TTF-1 expression.

Example 3

Reduction of ROR1 Expression by Suppressing TTF-1 Expression

Suppression of TTF-1 Expression (by RNA Interference) and Western Blotting

Cells of the pulmonary adenocarcinoma cell lines SK-LC-5 and NCI-H1975 expressing both TTF-1 and ROR1 were transfected with a scramble RNA or TTF-1 siRNAs (QIAGEN) at a final concentration of 20 nM using RNAiMAX (Invitrogen). 72 hours after transfection, lysates were prepared using SDS sample buffer. At the same time, samples without any treatment were prepared. After SDS-PAGE, Western blotting was carried out using an anti-ROR1 antibody (Cell signaling), anti-TTF-1 antibody (WAKO), or anti-α-tubulin antibody (Cell signaling).

Figure 3:
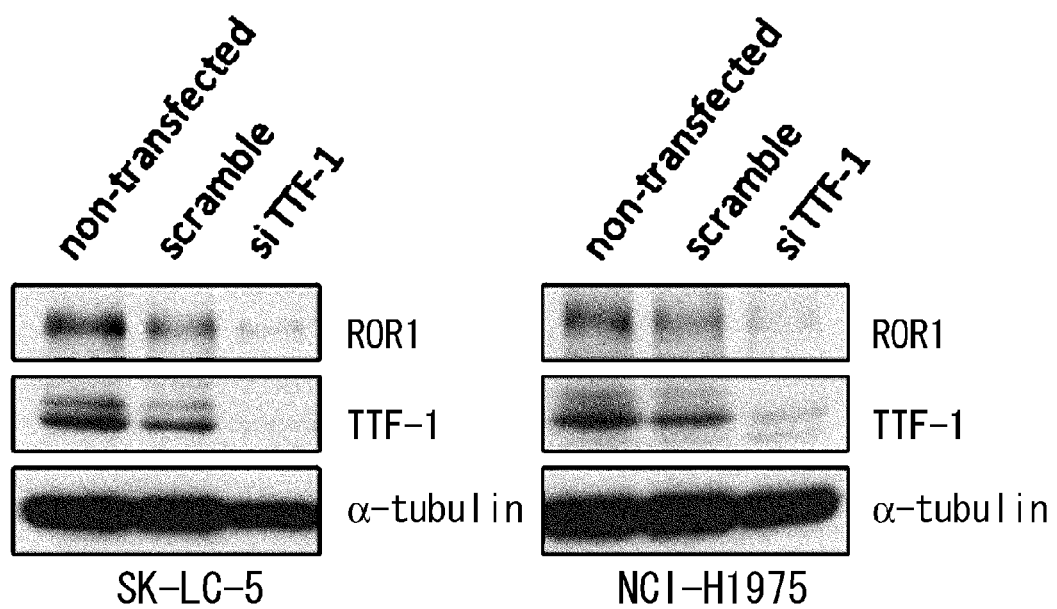
FIG. 3 shows in photographs decrease in the ROR1 expression level due to suppression of TTF-1 expression. The expression of TTF-1 was suppressed by siRNA in cells of pulmonary adenocarcinoma lines SK-LC-5 and NCI-H1975 which express both TTF-1 and ROR1. The result of Western blotting showed that in both pulmonary adenocarcinoma cell lines, the expression of TTF-1 was significantly suppressed by TTF-1 siRNA (siTTF-1) as compared to the control siRNA (scramble), and as a result the level of ROR1 expression was reduced in a specific manner. Thus, the expression of endogenous ROR1 was shown to be specifically regulated/controlled by TTF-1 expression in pulmonary adenocarcinoma cells.

Results and Discussion (FIG. 3)

TTF-1 expression was suppressed by RNA interference (RNAi) using an siRNA in the pulmonary adenocarcinoma lines SK-LC-5 and NCI-H1975 expressing both TTF-1 and ROR1. The result of Western blotting showed that in both of the pulmonary adenocarcinoma cell lines, TTF-1 expression was significantly suppressed and ROR1 expression was specifically reduced by the TTF-1 siRNA (siTTF-1) compared to the control siRNA (scramble). The bands of TTF-1 and ROR1 were both detected in the non-transfected cells of the pulmonary adenocarcinoma cell lines without any treatment, and it was shown that these genes were expressed in SK-LC-5 and NCI-H1975.

The expression of α-tubulin indicates that the protein quantity were equivalent in the three (non-transfected, scramble, and siTTF-1) samples, and siTTF-1 did not affect the quantity of other proteins.

The above result shows that endogenous ROR1 expression is specifically regulated and controlled by TTF-1 expression in pulmonary adenocarcinoma cells.

Example 4

Regulation of ROR1 Expression by TTF-1 at the Transcriptional Level

Construction of the pGL4.1-ROR1 Promoter and Luciferase Assay (Reporter Assay)

For luciferase assay, the pGL4.1-ROR1 promoter was constructed by isolating the ROR1 promoter from a human genomic cDNA and inserting about 1,000 bp of the promoter into the pGL4.1 luciferase reporter vector (Promega). $2 \times 10^5$ cells of a strain that stably expresses the control vector (CV) or TTF-1 (CV-stable or TTF-1-stable) were plated in 6-well plates. After 24 hours, the cells were co-transfected with 1.8 µg of the pGL4.1-ROR1 promoter and 0.2 µg of the pRL-TK vector using FuGENE6 Transfection Reagent (Roche Diagnostics), according to the Dual-Luciferase Reporter Assay System (Promega). 24 hours after transfection, the culture medium was removed, and after 48 hours, lysates were prepared using a PLB solution. 30 µl of LARII solution was added to 20 µl of the collected samples. The firefly luciferase activity was measured using Minirumat LB9506 ($M_1$). Then, 30 µl of Stop & Glo solution was added thereto, and the Renilla luciferase activity was measured in the same way using Minirumat LB9506 ($M_2$). The measured values of luciferase activity were calculated according to the formula: $M=(M_1-M_2)$. Mean values from triplicate measurements were presented in a graph.

Figure 4:
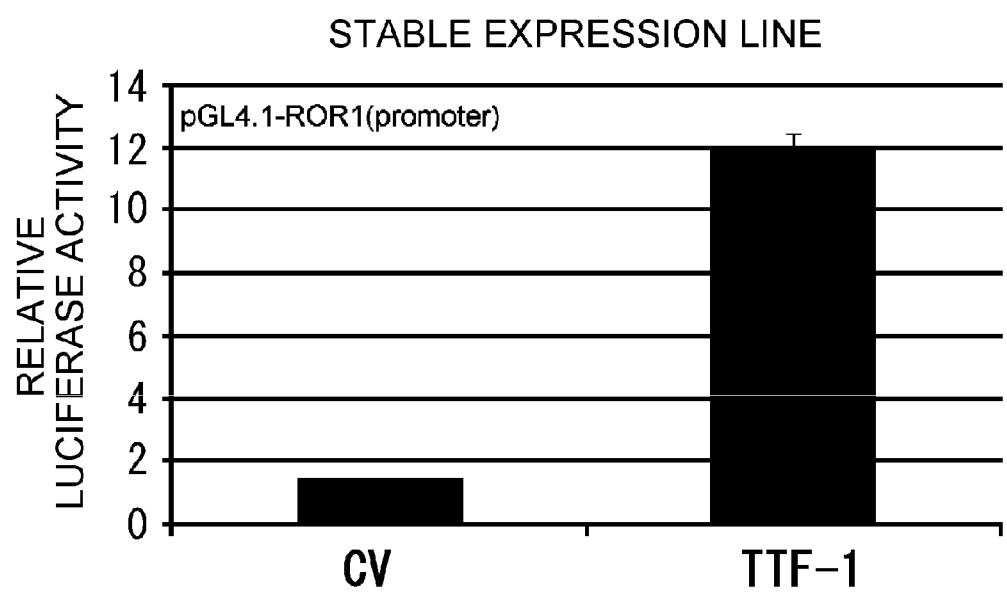
FIG. 4 shows in a graph regulation of the ROR1 expression by TTF-1 at the transcription level. Luciferase assay was carried out using an expression vector inserted with an ROR1 promoter region. The result demonstrated that the cell line stably expressing TTF-1 (TTF-1-stable) exhibited a significant luciferase activity as compared to the cell line stably expressing the control vector (CV) (CV-stable). This finding revealed that the ROR1 expression was induced by TTF-1 expression. Thus, it was demonstrated that the expression of ROR1 was regulated by TTF-1 at the transcription level.

Results and Discussion (FIG. 4)

To assess whether ROR1 expression is regulated by TTF-1 at the transcription level, an expression vector into which the promoter region of ROR1 was inserted was constructed. Then, luciferase assay which is a reporter assay was carried out. As a result, the cell line stably expressing TTF-1 (TTF-1-stable) exhibited significant luciferase activity (about eight times higher) compared to the cell line stably expressing the control vector (CV) (CV-stable).

The above result revealed that ROR1 expression is induced by TTF-1 expression. Thus, ROR1 expression was demonstrated to be regulated by TTF-1 at the transcription level.

Example 5

Localization of TTF-1 and ROR1 in Pulmonary Adenocarcinoma Tissues from Clinical Specimens Immunohistochemical Staining of Clinical Specimens (TTF-1 and ROR1)

The clinical specimens of pulmonary adenocarcinoma were tissue sections that were fixed with formalin and embedded in paraffin, and they were used for staining with either an anti-ROR1 antibody (Cell Signaling) or an anti-TTF-1 antibody (WAKO). For immunohistochemical staining with the anti-ROR1 antibody, the sections were soaked in 1 mM EDTA solution (pH 8.0) after deparaffinization, and treated with a microwave at 98° C. for ten minutes to unmask the antigen. Then, endogenous peroxidase was inactivated by treatment with methanol containing 3% hydrogen peroxide, and blocking was performed with 10% normal goat serum (Histofine SAB-PO(R) kit). The sections were incubated for one hour with an anti-ROR1 antibody diluted 100-fold, and then for ten minutes with a biotin-labeled anti-rabbit antibody IgG antibody (Histofine SAB-PO(R) kit) as the secondary antibody. After incubation with a peroxidase-labeled streptavidin (Histofine SAB-PO(R) kit), the chromogenic reaction was carried out using DAB. Furthermore, the sections were counter-stained with hematoxylin. Meanwhile, immunohistochemical staining with the anti-TTF-1 antibody was carried out using Ventana NX which is an automated immunostaining device. The antigen was unmasked by soaking the sections in Target Retrieval Solution 51700 (Dako Cytomation) and treating them with a microwave at 95° C. for 30 minutes. After the blocking reaction, the sections were incubated for one hour with an anti-TTF-1 antibody diluted 200-fold. The Ventana i-view DAB universal kit was used for reagents for secondary antibody reaction, DAB staining and such. Finally, counter staining was carried out using hematoxylin.

Figure 5:
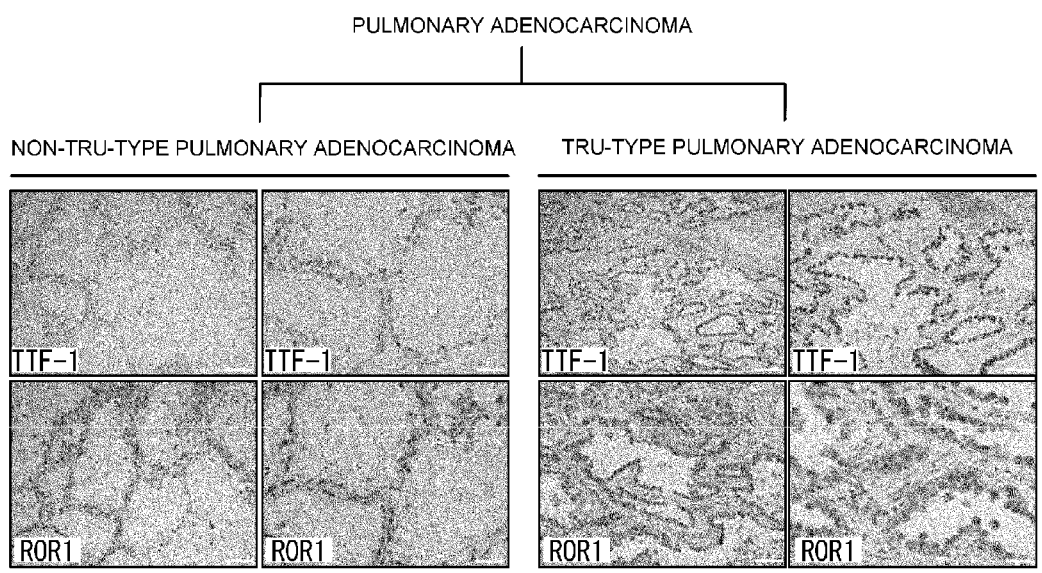
FIG. 5 shows in photographs the localization of TTF-1 and ROR1 in pulmonary adenocarcinoma tissues from clinical specimens. The results of immunohistochemistry of pulmonary adenocarcinoma tissues from clinical specimens showed that TTF-1 and ROR1 were specifically localized in terminal respiratory unit (TRU)-type pulmonary adenocarcinoma. Meanwhile, it was also demonstrated that TTF-1 and ROR1 were not localized in pulmonary adenocarcinoma derived from a more central portion (non-TRU-type). This suggests the possibility that ROR1 is regulated by TTF-1 in TRU-type pulmonary adenocarcinoma expressing TTF-1.

Results and Discussion (FIG. 5)

Pulmonary adenocarcinoma tissues from actual clinical specimens were immunostained to determine the tissue localization of TTF-1 and ROR1. The result demonstrated that TTF-1 and ROR1 are specifically localized in terminal respiratory unit (TRU)-type pulmonary adenocarcinoma. It was also demonstrated that neither TTF-1 nor ROR1 is localized in non-TRU-type pulmonary adenocarcinoma which is derived from a more central area.

The above result indicates the possibility that ROR1 is regulated by TTF-1 in TRU-type pulmonary adenocarcinoma which expresses TTF-1. Thus, it is suggested that ROR1 plays an important role. Furthermore, based on this finding, clinical use of therapeutic methods that target ROR1 is expected.

Meanwhile, high ROR1 expression is also detected in other tumors. Thus, it is also thought that ROR1 is an important factor for the survival of ROR1-positive cancer cells, and thus it can be a therapeutic target.

Example 6

ROR1 and TTF-1 Expressions in Various Cancer Cells

Preparation of Samples from Various Types of Cancer Cells and Western Blotting

Various lung cancer cells (pulmonary adenocarcinoma, squamous cell carcinoma, large cell carcinoma, and small cell carcinoma), osteosarcoma cells, colorectal adenocarcinoma cells, breast cancer cells, chronic myelocytic leukemia cells, cervical cancer cells, liver cancer cells, pancreatic cancer cells, and mesothelioma cells were grown in 60-mm dishes. Then, lysates were prepared using SDS sample buffer. Likewise, bronchial epithelial cells, epithelial cells of peripheral trachea, mesothelial cells, and embryonic renal cells were grown in 60-mm dishes, and lysates were prepared using SDS sample buffer. Furthermore, as a positive control (P.C.), pCMV-puro-ROR1 (a plasmid in which a human ROR1 cDNA purchased from OriGene was inserted into the pCMV-puro vector) was transiently expressed in HPL1D cells which are an epithelial cell line from peripheral trachea. After two days of puromycin (1.5 µg/ml) selection, lysates were prepared using SDS sample buffer in the same manner. After SDS-PAGE, Western blotting was carried out using an anti-ROR1 antibody (Cell Signaling) or an anti-TTF-1 antibody (WAKO).

Figure 6:
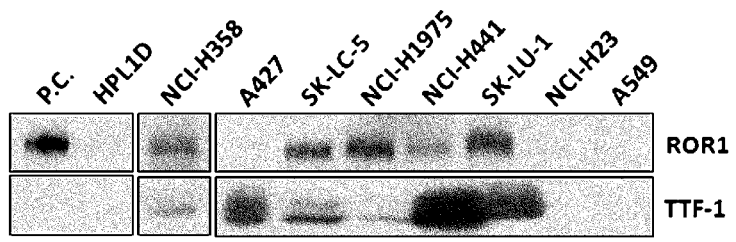
FIG. 6 shows in photographs the expression of ROR1 and TTF-1 in various cancer cells. Expression of ROR1 and TTF-1 in various cells was assessed by Western blotting. ROR1 expression was detected in various cancer-derived cells. Meanwhile, TTF-1 was demonstrated to be specifically expressed in pulmonary adenocarcinoma. Furthermore, it was revealed that ROR1 was not expressed in normal cells which were not derived from cancer. The result described above showed that TTF-1 was specifically expressed in pulmonary adenocarcinoma while ROR1 was expressed in various cancer-derived cells in a cancer cell-specific manner.
Figure 6:
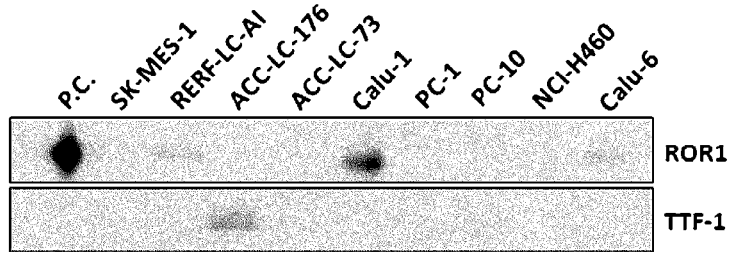
Figure 6:
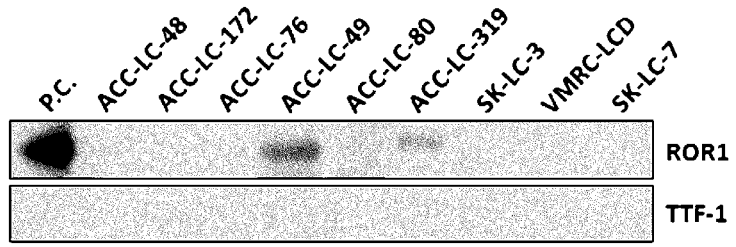
Figure 6:
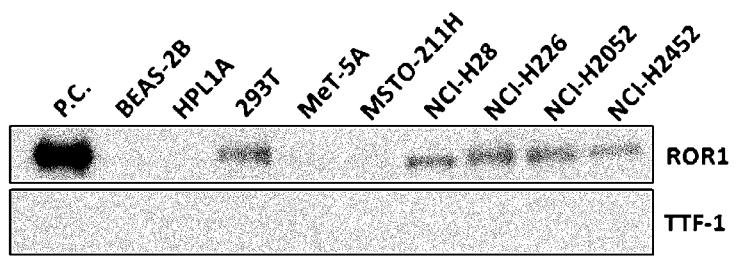
Figure 6:
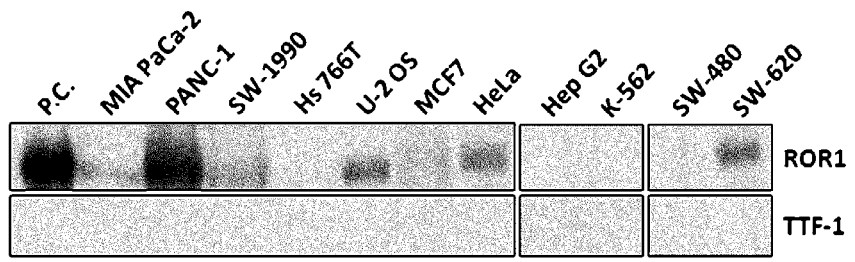

Results and Discussion (FIG. 6)

Western blotting was carried out to assess ROR1 and TTF-1 expressions in various cells at the protein level. The results demonstrated that that ROR1 is expressed in various cancer-derived cells, and TTF-1 is expressed specifically in pulmonary adenocarcinoma. Furthermore, it was revealed that ROR1 is not expressed in normal cells which are not derived from cancer.

The above results show that TTF-1 expression is specific to pulmonary adenocarcinoma, while ROR1 expression is specific to cancer cells and it is found in various cancer-derived cells.

Example 7

List of Various Cancer Cells with ROR1 and TTF-1 Expressions

List of TTF-1 and ROR1 Expressions in Various Cancer Cell Lines

The results of TTF-1 and ROR1 expressions at the protein level are summarized (Table 2) based on the Western blot results described in Example 6.

TABLE 2

| Cell Name | Organ | Disease/Histology | ROR1 expression | TTF-1 expression |
|---|---|---|---|---|
| U-2 OS | bone | osteosarcoma | + | − |
| MCF7 | mammary gland; breast | adenocarcinoma | − | − |
| SW-480 | colon | colorectal adenocarcinoma | − | − |
| SW-620 | colon | colorectal adenocarcinoma | + | − |
| K-562 | bone marrow | chronic myelogenous leukemia (CML) | − | − |
| HeLa | uterus | endocervical carcinoma | + | − |
| Hep G2 | liver | hepatocellular carcinoma | − | − |
| MIA Paca-2 | pancreas | carcinoma | + | − |
| PANC-1 | pancreas | adenocarcinoma | + | − |
| SW-1990 | pancreas | adenocarcinoma | + | − |
| Hs 766T | pancreas | adenocarcinoma | − | − |
| MeT-5A | mesothelium | epithelial; virus transformed | − | − |
| MSTO-211H | lung | mesothelioma | − | − |
| NCI-H28 | lung | mesothelioma | + | − |
| NCI-H226 | lung | squamous cell carcinoma: mesothelioma | + | − |
| NCI-H2052 | lung | mesothelioma | + | − |
| NCI-H2452 | lung | mesothelioma | + | − |
| HPL1D | lung | Peripheral airway epithelial cell | − | − |
| NCI-H358 | lung | BAC, bronchioalveolar carcinoma | + | + |
| A427 | lung | Adenocarcinoma | − | + |
| SK-LC-5 | lung | Adenocarcinoma | + | + |
| NCI-H1975 | lung | Adenocarcinoma | + | + |
| NCI-H441 | lung | Adenocarcinoma | + | + |
| SK-LU-1 | lung | Adenocarcinoma | + | + |

TABLE 2-continued

| Cell Name | Organ | Disease/ Histology | ROR1 expression | TTF-1 expression |
|---|---|---|---|---|
| NCI-H23 | lung | Adenocarcinoma | − | − |
| A549 | lung | Adenocarcinoma | − | − |
| SK-MES-1 | lung | Squamous cell carcinoma | − | − |
| RERF-LC-Al | lung | Squamous cell carcinoma | + | − |
| ACC-LC-176 | lung | Squamous cell carcinoma | − | + |
| ACC-LC-73 | lung | Squamous cell carcinoma | − | − |
| Calu-1 | lung | Squamous cell carcinoma | + | − |
| PC-1 | lung | Squamous cell carcinoma | − | − |
| PC-10 | lung | Squamous cell carcinoma | − | − |
| NCI-H460 | lung | Large cell carcinoma | − | − |
| Calu-6 | lung | Large cell carcinoma | + | − |
| ACC-LC-48 | lung | Small cell carcinoma | − | − |
| ACC-LC-172 | lung | Small cell carcinoma | − | − |
| ACC-LC-76 | lung | Small cell carcinoma | − | − |
| ACC-LC-49 | lung | Small cell carcinoma | + | − |
| ACC-LC-80 | lung | Small cell carcinoma | − | − |
| ACC-LC-319 | lung | Adenocarcinoma | + | − |
| SK-LC-3 | lung | Adenocarcinoma | − | − |
| VMRC-LCD | lung | Adenocarcinoma | − | − |
| SK-LC-7 | lung | Adenocarcinoma | − | − |
| BEAS-2B | lung | Bronchial airway epithelial cell | − | − |
| HPL1A | lung | Peripheral airway epithelial cell | − | − |
| 293T | kidney | Embryonic kidney cell | + | − |

Results and Discussion

The ROR1 and TTF-1 expressions at the protein level in various cells and their correlation are summarized based on the results described in Example 6. It was revealed that ROR1 is expressed in various cancer-derived cells, for example, cells derived from osteosarcoma (U-2 OS), cells derived from colorectal adenocarcinoma (SW-620), cells derived from pancreatic cancer (MIA PaCa2, PANC-1, etc.), cells derived from mesothelioma (NCI-H28, NCI-H226, NCI-H2052, etc.), and various lung cancer-derived cells. Meanwhile, ROR1 expression was not observed in normal cells, for example, bronchial epithelial cells (BEAS-2B), epithelial cells of peripheral trachea (HPL1D and HPL1A), and mesothelial cells (MeT-5A).

ROR1 is ubiquitously expressed in various cancer-derived cells, while its expression is almost undetectable in normal cells. Thus, clinical use of ROR1 inhibition and its application to cancer cell-specific therapeutic methods are expected. Meanwhile, TTF-1 was demonstrated to be expressed in cells derived from pulmonary adenocarcinoma. ROR1 expression is thought to be regulated by TTF-1 in pulmonary adenocarcinoma. In other tumors, ROR1 transcription is thought to be activated by other transcriptional factors.

Example 8

Design of Human ROR1 siRNAs

Design of Human ROR1 siRNAs Using Various Software

To design human ROR1 siRNAs, candidate siRNAs against human ROR1 (NM_005012) were selected using two siRNA design databases [software] (RNAi Central and siRNA Target Finder). Human ROR1 siRNAs identified by the software were selected based on individual siRNA designing algorithms (siRNA programs). The siRNAs identified are potentially capable of suppressing the expression of human ROR1. RNAi Central selected 293 human ROR1 siRNAs that are expected to exhibit the expression-suppressing effect, as shown on a ranking list. Meanwhile, siRNA Target Finder selected 174 human ROR1 siRNAs that are expected to exhibit the expression-suppressing effect.

Results and Discussion

Figure 7:
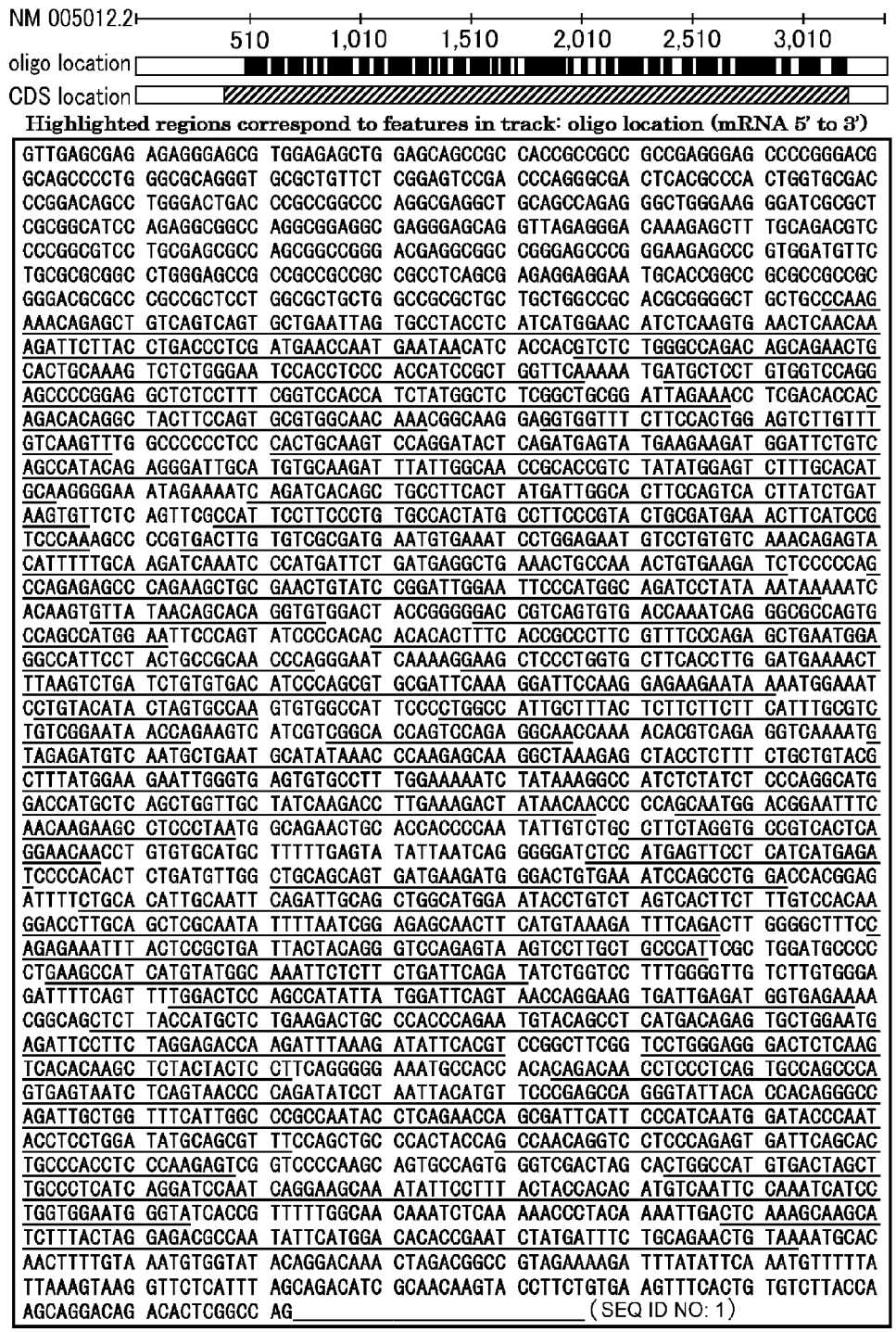
FIG. 7 shows in a diagram the positions of siRNA target sequences in ROR1. The sequences were designed using a design program, the RNAi Central (siRNA design) software. Target sequences are underlined.

ROR1 siRNAs against human ROR1 (NM_005012) were designed and candidate siRNAs were selected using the two siRNA design databases [software] (RNAi Central and siRNA Target Finder). That is, using the siRNA programs, human ROR1 siRNAs that are expected to exhibit the expression-suppressing effect were selected. RNAi Central and siRNA Target Finder identified 293 (FIG. 7) and 174 siRNAs, respectively.

The details are described below.

(1) RNAi Central (siRNA Design) Software
[Hannon Lab; Maintained by Sachidanandam Lab]
katahdin.cshl.org:9331/homepage/portal/scripts/main2.pl)

The sense strands of siRNAs against human ROR1 (NM_005012: target sequence) are described below.

```
NM_005012 Start position: 924
GATTGCATGTGCAAGATTT                      (SEQ ID NO: 4)

NM_005012 Start position: 2727
CCCAGTGAGTAATCTCAGT                      (SEQ ID NO: 5)

NM_005012 Start position: 1269
CCCAGAAGCTGCGAACTGT                      (SEQ ID NO: 6)

NM_005012 Start position: 1394
GCCAGTGCCAGCCATGGAA                      (SEQ ID NO: 7)

NM_005012 Start position: 1174
CTGTGTCAAACAGAGTACA                      (SEQ ID NO: 8)

NM_005012 Start position: 1368
GACCGTCAGTGTGACCAAA                      (SEQ ID NO: 9)

NM_005012 Start position: 1305
CATGGCAGATCCTATAAAT                      (SEQ ID NO: 10)

NM_005012 Start position: 501
GTCAGTCAGTGCTGAATTA                      (SEQ ID NO: 11)

NM_005012 Start position: 1950
GACGGAATTTCAACAAGAA                      (SEQ ID NO: 12)

NM_005012 Start position: 2270
GAGAGCAACTTCATGTAAA                      (SEQ ID NO: 13)

NM_005012 Start position: 1163
TGGAGAATGTCCTGTGTCA                      (SEQ ID NO: 14)

NM_005012 Start position: 2400
CAAATTCTCTTCTGATTCA                      (SEQ ID NO: 15)

NM_005012 Start position: 2647
GAGGGACTCTCAAGTCACA                      (SEQ ID NO: 16)

NM_005012 Start position: 2921
CTCCCAGAGTGATTCAGCA                      (SEQ ID NO: 17)

NM_005012 Start position: 520
GTGCCTACCTCATCATGGA                      (SEQ ID NO: 18)

NM_005012 Start position: 1654
GCTTTACTCTTCTTCTTCA                      (SEQ ID NO: 19)

NM_005012 Start position: 1033
TCCAGTCACTTATCTGATA                      (SEQ ID NO: 20)

NM_005012 Start position: 956
CCGTCTATATGGAGTCTTT                      (SEQ ID NO: 21)

NM_005012 Start position: 658
CCCACCATCCGCTGGTTCA                      (SEQ ID NO: 22)

NM_005012 Start position: 1082
GCCACTATGCCTTCCCGTA                      (SEQ ID NO: 23)

NM_005012 Start position: 2865
CCCAATACCTCCTGGATAT                      (SEQ ID NO: 24)

NM_005012 Start position: 1140
GTGTCGCGATGAATGTGAA                      (SEQ ID NO: 25)

NM_005012 Start position: 1038
TCACTTATCTGATAAGTGT                      (SEQ ID NO: 26)

NM_005012 Start position: 2851
CCCATCAATGGATACCCAA                      (SEQ ID NO: 27)

-continued
NM_005012 Start position: 2729
CAGTGAGTAATCTCAGTAA                      (SEQ ID NO: 28)

NM_005012 Start position: 1772
CATATAAACCCAAGAGCAA                      (SEQ ID NO: 29)

NM_005012 Start position: 785
TCCAGTGCGTGGCAACAAA                      (SEQ ID NO: 30)

NM_005012 Start position: 2554
CCCAGAATGTACAGCCTCA                      (SEQ ID NO: 31)

NM_005012 Start position: 1836
GGGTGAGTGTGCCTTTGGA                      (SEQ ID NO: 32)

NM_005012 Start position: 545
CAAGTGAACTCAACAAAGA                      (SEQ ID NO: 33)

NM_005012 Start position: 740
CTCGGCTGCGGATTAGAAA                      (SEQ ID NO: 34)

NM_005012 Start position: 636
CAAAGTCTCTGGGAATCCA                      (SEQ ID NO: 35)

NM_005012 Start position: 3181
CACACCGAATCTATGATTT                      (SEQ ID NO: 36)

NM_005012 Start position: 1676
GCGTCTGTCGGAATAACCA                      (SEQ ID NO: 37)

NM_005012 Start position: 2474
CATATTATGGATTCAGTAA                      (SEQ ID NO: 38)

NM_005012 Start position: 2993
CTGGCCATGTGACTAGCTT                      (SEQ ID NO: 39)

NM_005012 Start position: 706
CGGAGGCTCTCCTTTCGGT                      (SEQ ID NO: 40)

NM_005012 Start position: 918
CAGAGGGATTGCATGTGCA                      (SEQ ID NO: 41)

NM_005012 Start position: 2874
TCCTGGATATGCAGCGTTT                      (SEQ ID NO: 42)

NM_005012 Start position: 1567
GCGTGCGATTCAAAGGATT                      (SEQ ID NO: 43)

NM_005012 Start position: 1205
CAAATCCCATGATTCTGAT                      (SEQ ID NO: 44)

NM_005012 Start position: 1211
CCATGATTCTGATGAGGCT                      (SEQ ID NO: 45)

NM_005012 Start position: 781
TACTTCCAGTGCGTGGCAA                      (SEQ ID NO: 46)

NM_005012 Start position: 2472
GCCATATTATGGATTCAGT                      (SEQ ID NO: 47)

NM_005012 Start position: 2561
TGTACAGCCTCATGACAGA                      (SEQ ID NO: 48)

NM_005012 Start position: 2398
GGCAAATTCTCTTCTGATT                      (SEQ ID NO: 49)

NM_005012 Start position: 3055
CCACACATGTCAATTCCAA                      (SEQ ID NO: 50)

NM_005012 Start position: 2841
GCGATTCATTCCCATCAAT                      (SEQ ID NO: 51)

NM_005012 Start position: 1913
TCAAGACCTTGAAAGACTA                      (SEQ ID NO: 52)

NM_005012 Start position: 1577
CAAAGGATTCCAAGGAGAA                      (SEQ ID NO: 53)

NM_005012 Start position: 2193
GATTGCAGCTGGCATGGAA                      (SEQ ID NO: 54)
```

-continued

| | |
|---|---|
| NM_005012 Start position: 2910 GCCAACAGGTCCTCCCAGA | (SEQ ID NO: 55) |
| NM_005012 Start position: 961 TATATGGAGTCTTTGCACA | (SEQ ID NO: 56) |
| NM_005012 Start position: 2645 GGGAGGGACTCTCAAGTCA | (SEQ ID NO: 57) |
| NM_005012 Start position: 965 TGGAGTCTTTGCACATGCA | (SEQ ID NO: 58) |
| NM_005012 Start position: 879 CTCAGATGAGTATGAAGAA | (SEQ ID NO: 59) |
| NM_005012 Start position: 620 CAGCAGAACTGCACTGCAA | (SEQ ID NO: 60) |
| NM_005012 Start position: 1095 CCCGTACTGCGATGAAACT | (SEQ ID NO: 61) |
| NM_005012 Start position: 1919 CCTTGAAAGACTATAACAA | (SEQ ID NO: 62) |
| NM_005012 Start position: 2078 TCCATGAGTTCCTCATCAT | (SEQ ID NO: 63) |
| NM_005012 Start position: 1539 CTTTAAGTCTGATCTGTGT | (SEQ ID NO: 64) |
| NM_005012 Start position: 1029 CACTTCCAGTCACTTATCT | (SEQ ID NO: 65) |
| NM_005012 Start position: 2492 ACCAGGAAGTGATTGAGAT | (SEQ ID NO: 66) |
| NM_005012 Start position: 2846 TCATTCCCATCAATGGATA | (SEQ ID NO: 67) |
| NM_005012 Start position: 1817 TACGCTTTATGGAAGAATT | (SEQ ID NO: 68) |
| NM_005012 Start position: 1093 TTCCCGTACTGCGATGAAA | (SEQ ID NO: 69) |
| NM_005012 Start position: 2222 GTCACTTCTTTGTCCACAA | (SEQ ID NO: 70) |
| NM_005012 Start position: 1165 GAGAATGTCCTGTGTCAAA | (SEQ ID NO: 71) |
| NM_005012 Start position: 1031 CTTCCAGTCACTTATCTGA | (SEQ ID NO: 72) |
| NM_005012 Start position: 1507 GAAGCTCCCTGGTGCTTCA | (SEQ ID NO: 73) |
| NM_005012 Start position: 2777 GCCAGGGTATTACACCACA | (SEQ ID NO: 74) |
| NM_005012 Start position: 1805 CTCTTTCTGCTGTACGCTT | (SEQ ID NO: 75) |
| NM_005012 Start position: 1750 GTAGAGATGTCAATGCTGA | (SEQ ID NO: 76) |
| NM_005012 Start position: 1176 GTGTCAAACAGAGTACATT | (SEQ ID NO: 77) |
| NM_005012 Start position: 1944 GCAATGGACGGAATTTCAA | (SEQ ID NO: 78) |
| NM_005012 Start position: 1282 AACTGTATCCGGATTGGAA | (SEQ ID NO: 79) |
| NM_005012 Start position: 932 GTGCAAGATTTATTGGCAA | (SEQ ID NO: 80) |
| NM_005012 Start position: 533 CATGGAACATCTCAAGTGA | (SEQ ID NO: 81) |
| NM_005012 Start position: 2712 CTCCCTCAGTGCCAGCCCA | (SEQ ID NO: 82) |
| NM_005012 Start position: 1859 TCTATAAAGGCCATCTCTA | (SEQ ID NO: 83) |
| NM_005012 Start position: 1898 CTCAGCTGGTTGCTATCAA | (SEQ ID NO: 84) |
| NM_005012 Start position: 578 TCGATGAACCAATGAATAA | (SEQ ID NO: 85) |
| NM_005012 Start position: 2019 TGCCGTCACTCAGGAACAA | (SEQ ID NO: 86) |
| NM_005012 Start position: 3060 CATGTCAATTCCAAATCAT | (SEQ ID NO: 87) |
| NM_005012 Start position: 523 CCTACCTCATCATGGAACA | (SEQ ID NO: 88) |
| NM_005012 Start position: 3144 GCAAGCATCTTTACTAGGA | (SEQ ID NO: 89) |
| NM_005012 Start position: 1098 GTACTGCGATGAAACTTCA | (SEQ ID NO: 90) |
| NM_005012 Start position: 2268 CGGAGAGCAACTTCATGTA | (SEQ ID NO: 91) |
| NM_005012 Start position: 2244 CCTTGCAGCTCGCAATATT | (SEQ ID NO: 92) |
| NM_005012 Start position: 1910 CTATCAAGACCTTGAAAGA | (SEQ ID NO: 93) |
| NM_005012 Start position: 2121 CTGCAGCAGTGATGAAGAT | (SEQ ID NO: 94) |
| NM_005012 Start position: 2274 GCAACTTCATGTAAAGATT | (SEQ ID NO: 95) |
| NM_005012 Start position: 1307 TGGCAGATCCTATAAATAA | (SEQ ID NO: 96) |
| NM_005012 Start position: 2181 CATTGCAATTCAGATTGCA | (SEQ ID NO: 97) |
| NM_005012 Start position: 2333 ACTACAGGGTCCAGAGTAA | (SEQ ID NO: 98) |
| NM_005012 Start position: 1812 TGCTGTACGCTTTATGGAA | (SEQ ID NO: 99) |
| NM_005012 Start position: 2576 CAGAGTGCTGGAATGAGAT | (SEQ ID NO: 100) |
| NM_005012 Start position: 1436 CTTTCCACCGCCCTTCGTTT | (SEQ ID NO: 101) |
| NM_005012 Start position: 1904 TGGTTGCTATCAAGACCTT | (SEQ ID NO: 102) |
| NM_005012 Start position: 3138 CTCAAAGCAAGCATCTTTA | (SEQ ID NO: 103) |
| NM_005012 Start position: 2831 CTCAGAACCAGCGATTCAT | (SEQ ID NO: 104) |
| NM_005012 Start position: 1871 ATCTCTATCTCCCAGGCAT | (SEQ ID NO: 105) |
| NM_005012 Start position: 1900 CAGCTGGTTGCTATCAAGA | (SEQ ID NO: 106) |
| NM_005012 Start position: 2604 GAGACCAAGATTTAAAGAT | (SEQ ID NO: 107) |
| NM_005012 Start position: 2940 CTGCCCACCTCCCAAGAGT | (SEQ ID NO: 108) |

NM_005012 Start position: 1571
GCGATTCAAAGGATTCCAA (SEQ ID NO: 109)

NM_005012 Start position: 2219
CTAGTCACTTCTTTGTCCA (SEQ ID NO: 110)

NM_005012 Start position: 1652
TTGCTTTACTCTTCTTCTT (SEQ ID NO: 111)

NM_005012 Start position: 2344
CAGAGTAAGTCCTTGCTGC (SEQ ID NO: 112)

NM_005012 Start position: 1440
CACCGCCCTTCGTTTCCCA (SEQ ID NO: 113)

NM_005012 Start position: 770
CAGACACAGGCTACTTCCA (SEQ ID NO: 114)

NM_005012 Start position: 2314
GAAATTTACTCCGCTGATT (SEQ ID NO: 115)

NM_005012 Start position: 2348
GTAAGTCCTTGCTGCCCAT (SEQ ID NO: 116)

NM_005012 Start position: 1811
CTGCTGTACGCTTTATGGA (SEQ ID NO: 117)

NM_005012 Start position: 873
AGGATACTCAGATGAGTAT (SEQ ID NO: 118)

NM_005012 Start position: 3056
CACACATGTCAATTCCAAA (SEQ ID NO: 119)

NM_005012 Start position: 625
GAACTGCACTGCAAAGTCT (SEQ ID NO: 120)

NM_005012 Start position: 503
CAGTCAGTGCTGAATTAGT (SEQ ID NO: 121)

NM_005012 Start position: 772
GACACAGGCTACTTCCAGT (SEQ ID NO: 122)

NM_005012 Start position: 1271
CAGAAGCTGCGAACTGTAT (SEQ ID NO: 123)

NM_005012 Start position: 1657
TTACTCTTCTTCTTCATTT (SEQ ID NO: 124)

NM_005012 Start position: 2195
TTGCAGCTGGCATGGAATA (SEQ ID NO: 125)

NM_005012 Start position: 1670
TCATTTGCGTCTGTCGGAA (SEQ ID NO: 126)

NM_005012 Start position: 1007
CAGCTGCCTTCACTATGAT (SEQ ID NO: 127)

NM_005012 Start position: 1895
ATGCTCAGCTGGTTGCTAT (SEQ ID NO: 128)

NM_005012 Start position: 1108
GAAACTTCATCCGTCCCAA (SEQ ID NO: 129)

NM_005012 Start position: 1134
TGACTTGTGTCGCGATGAA (SEQ ID NO: 130)

NM_005012 Start position: 1070
TTCCTTCCCTGTGCCACTA (SEQ ID NO: 131)

NM_005012 Start position: 715
TCCTTTCGGTCCACCATCT (SEQ ID NO: 132)

NM_005012 Start position: 2386
GCCATCATGTATGGCAAAT (SEQ ID NO: 133)

NM_005012 Start position: 2606
GACCAAGATTTAAAGATAT (SEQ ID NO: 134)

NM_005012 Start position: 499
CTGTCAGTCAGTGCTGAAT (SEQ ID NO: 135)

NM_005012 Start position: 528
CTCATCATGGAACATCTCA (SEQ ID NO: 136)

NM_005012 Start position: 3183
CACCGAATCTATGATTTCT (SEQ ID NO: 137)

NM_005012 Start position: 1430
CACACACTTTCACCGCCCT (SEQ ID NO: 138)

NM_005012 Start position: 1548
TGATCTGTGTGACATCCCA (SEQ ID NO: 139)

NM_005012 Start position: 2915
CAGGTCCTCCCAGAGTGAT (SEQ ID NO: 140)

NM_005012 Start position: 3195
GATTTCTGCAGAACTGTAA (SEQ ID NO: 141)

NM_005012 Start position: 1814
CTGTACGCTTTATGGAAGA (SEQ ID NO: 142)

NM_005012 Start position: 827
CTGGAGTCTTGTTTGTCAA (SEQ ID NO: 143)

NM_005012 Start position: 2716
CTCAGTGCCAGCCCAGTGA (SEQ ID NO: 144)

NM_005012 Start position: 2207
TGGAATACCTGTCTAGTCA (SEQ ID NO: 145)

NM_005012 Start position: 1445
CCCTTCGTTTCCCAGAGCT (SEQ ID NO: 146)

NM_005012 Start position: 577
CTCGATGAACCAATGAATA (SEQ ID NO: 147)

NM_005012 Start position: 1761
AATGCTGAATGCATATAAA (SEQ ID NO: 148)

NM_005012 Start position: 2775
GAGCCAGGGTATTACACCA (SEQ ID NO: 149)

NM_005012 Start position: 830
GAGTCTTGTTTGTCAAGTT (SEQ ID NO: 150)

NM_005012 Start position: 1645
CTGGCCATTGCTTTACTCT (SEQ ID NO: 151)

NM_005012 Start position: 2599
TCTAGGAGACCAAGATTTA (SEQ ID NO: 152)

NM_005012 Start position: 3033
GGAAGCAAATATTCCTTTA (SEQ ID NO: 153)

NM_005012 Start position: 922
GGGATTGCATGTGCAAGAT (SEQ ID NO: 154)

NM_005012 Start position: 3027
CAATCAGGAAGCAAATATT (SEQ ID NO: 155)

NM_005012 Start position: 2279
TTCATGTAAAGATTTCAGA (SEQ ID NO: 156)

NM_005012 Start position: 2083
GAGTTCCTCATCATGAGAT (SEQ ID NO: 157)

NM_005012 Start position: 1276
GCTGCGAACTGTATCCGGA (SEQ ID NO: 158)

NM_005012 Start position: 824
CCACTGGAGTCTTGTTTGT (SEQ ID NO: 159)

NM_005012 Start position: 898
GATGGATTCTGTCAGCCAT (SEQ ID NO: 160)

NM_005012 Start position: 1561
ATCCCAGCGTGCGATTCAA (SEQ ID NO: 161)

NM_005012 Start position: 3164
ACGCCAATATTCATGGACA (SEQ ID NO: 162)

| NM_005012 Start position: 861 CACTGCAAGTCCAGGATAC | (SEQ ID NO: 163) | NM_005012 Start position: 1541 TTAAGTCTGATCTGTGTGA | (SEQ ID NO: 190) |
|---|---|---|---|
| NM_005012 Start position: 3001 GTGACTAGCTTGCCCTCAT | (SEQ ID NO: 164) | NM_005012 Start position: 490 GAAACAGAGCTGTCAGTCA | (SEQ ID NO: 191) |
| NM_005012 Start position: 514 GAATTAGTGCCTACCTCAT | (SEQ ID NO: 165) | NM_005012 Start position: 912 GCCATACAGAGGGATTGCA | (SEQ ID NO: 192) |
| NM_005012 Start position: 881 CAGATGAGTATGAAGAAGA | (SEQ ID NO: 166) | NM_005012 Start position: 2015 TAGGTGCCGTCACTCAGGA | (SEQ ID NO: 193) |
| NM_005012 Start position: 2176 CTGCACATTGCAATTCAGA | (SEQ ID NO: 167) | NM_005012 Start position: 1200 AAGATCAAATCCCATGATT | (SEQ ID NO: 194) |
| NM_005012 Start position: 575 CCCTCGATGAACCAATGAA | (SEQ ID NO: 168) | NM_005012 Start position: 1146 CGATGAATGTGAAATCCTG | (SEQ ID NO: 195) |
| NM_005012 Start position: 608 CTCTGGGCCAGACAGCAGA | (SEQ ID NO: 169) | NM_005012 Start position: 2527 CTCTTACCATGCTCTGAAG | (SEQ ID NO: 196) |
| NM_005012 Start position: 2310 CAGAGAAATTTACTCCGCT | (SEQ ID NO: 170) | NM_005012 Start position: 2720 GTGCCAGCCCAGTGAGTAA | (SEQ ID NO: 197) |
| NM_005012 Start position: 486 CCAAGAAACAGAGCTGTCA | (SEQ ID NO: 171) | NM_005012 Start position: 497 AGCTGTCAGTCAGTGCTGA | (SEQ ID NO: 198) |
| NM_005012 Start position: 606 GTCTCTGGGCCAGACAGCA | (SEQ ID NO: 172) | NM_005012 Start position: 2463 TGGACTCCAGCCATATTAT | (SEQ ID NO: 199) |
| NM_005012 Start position: 513 TGAATTAGTGCCTACCTCA | (SEQ ID NO: 173) | NM_005012 Start position: 2481 TGGATTCAGTAACCAGGAA | (SEQ ID NO: 200) |
| NM_005012 Start position: 1860 CTATAAAGGCCATCTCTAT | (SEQ ID NO: 174) | NM_005012 Start position: 3069 TCCAAATCATCCTGGTGGA | (SEQ ID NO: 201) |
| NM_005012 Start position: 1827 GGAAGAATTGGGTGAGTGT | (SEQ ID NO: 175) | NM_005012 Start position: 2641 TCCTGGGAGGGACTCTCAA | (SEQ ID NO: 202) |
| NM_005012 Start position: 1154 GTGAAATCCTGGAGAATGT | (SEQ ID NO: 176) | NM_005012 Start position: 2552 CACCCAGAATGTACAGCCT | (SEQ ID NO: 203) |
| NM_005012 Start position: 1883 CAGGCATGGACCATGCTCA | (SEQ ID NO: 177) | NM_005012 Start position: 3175 CATGGACACACCGAATCTA | (SEQ ID NO: 204) |
| NM_005012 Start position: 1707 GGCACCAGTCCAGAGGCAA | (SEQ ID NO: 178) | NM_005012 Start position: 1000 CAGATCACAGCTGCCTTCA | (SEQ ID NO: 205) |
| NM_005012 Start position: 1447 CTTCGTTTCCCAGAGCTGA | (SEQ ID NO: 179) | NM_005012 Start position: 1202 GATCAAATCCCATGATTCT | (SEQ ID NO: 206) |
| NM_005012 Start position: 631 CACTGCAAAGTCTCTGGGA | (SEQ ID NO: 180) | NM_005012 Start position: 1151 AATGTGAAATCCTGGAGAA | (SEQ ID NO: 207) |
| NM_005012 Start position: 2144 CTGTGAAATCCAGCCTGGA | (SEQ ID NO: 181) | NM_005012 Start position: 1648 GCCATTGCTTTACTCTTCT | (SEQ ID NO: 208) |
| NM_005012 Start position: 1370 CCGTCAGTGTGACCAAATC | (SEQ ID NO: 182) | NM_005012 Start position: 1672 ATTTGCGTCTGTCGGAATA | (SEQ ID NO: 209) |
| NM_005012 Start position: 1800 GCTACCTCTTTCTGCTGTA | (SEQ ID NO: 183) | NM_005012 Start position: 2242 GACCTTGCAGCTCGCAATA | (SEQ ID NO: 210) |
| NM_005012 Start position: 776 CAGGCTACTTCCAGTGCGT | (SEQ ID NO: 184) | NM_005012 Start position: 3007 AGCTTGCCCTCATCAGGAT | (SEQ ID NO: 211) |
| NM_005012 Start position: 1558 GACATCCCAGCGTGCGATT | (SEQ ID NO: 185) | NM_005012 Start position: 2010 CCTTCTAGGTGCCGTCACT | (SEQ ID NO: 212) |
| NM_005012 Start position: 556 AACAAAGATTCTTACCTGA | (SEQ ID NO: 186) | NM_005012 Start position: 2327 CTGATTACTACAGGGTCCA | (SEQ ID NO: 213) |
| NM_005012 Start position: 2500 GTGATTGAGATGGTGAGAA | (SEQ ID NO: 187) | NM_005012 Start position: 1949 GGACGGAATTTCAACAAGA | (SEQ ID NO: 214) |
| NM_005012 Start position: 683 ATGCTCCTGTGGTCCAGGA | (SEQ ID NO: 188) | NM_005012 Start position: 1757 TGTCAATGCTGAATGCATA | (SEQ ID NO: 215) |
| NM_005012 Start position: 3076 CATCCTGGTGGAATGGGTA | (SEQ ID NO: 189) | NM_005012 Start position: 952 CGCACCGTCTATATGGAGT | (SEQ ID NO: 216) |

-continued

NM_005012 Start position: 2714
CCCTCAGTGCCAGCCCAGT (SEQ ID NO: 217)

NM_005012 Start position: 3071
CAAATCATCCTGGTGGAAT (SEQ ID NO: 218)

NM_005012 Start position: 712
CTCTCCTTTCGGTCCACCA (SEQ ID NO: 219)

NM_005012 Start position: 1785
GAGCAAGGCTAAAGAGCTA (SEQ ID NO: 220)

NM_005012 Start position: 2403
ATTCTCTTCTGATTCAGAT (SEQ ID NO: 221)

NM_005012 Start position: 2214
CCTGTCTAGTCACTTCTTT (SEQ ID NO: 222)

NM_005012 Start position: 2077
CTCCATGAGTTCCTCATCA (SEQ ID NO: 223)

NM_005012 Start position: 1778
AACCCAAGAGCAAGGCTAA (SEQ ID NO: 224)

NM_005012 Start position: 571
CTGACCCTCGATGAACCAA (SEQ ID NO: 225)

NM_005012 Start position: 944
TTGGCAACCGCACCGTCTA (SEQ ID NO: 226)

NM_005012 Start position: 1563
CCCAGCGTGCGATTCAAAG (SEQ ID NO: 227)

NM_005012 Start position: 2127
CAGTGATGAAGATGGGACT (SEQ ID NO: 228)

NM_005012 Start position: 1067
CCATTCCTTCCCTGTGCCA (SEQ ID NO: 229)

NM_005012 Start position: 2656
TCAAGTCACACAAGCTCTA (SEQ ID NO: 230)

NM_005012 Start position: 656
CTCCCACCATCCGCTGGTT (SEQ ID NO: 231)

NM_005012 Start position: 1003
ATCACAGCTGCCTTCACTA (SEQ ID NO: 232)

NM_005012 Start position: 1076
CCCTGTGCCACTATGCCTT (SEQ ID NO: 233)

NM_005012 Start position: 2541
TGAAGACTGCCCACCCAGA (SEQ ID NO: 234)

NM_005012 Start position: 871
CCAGGATACTCAGATGAGT (SEQ ID NO: 235)

NM_005012 Start position: 2198
CAGCTGGCATGGAATACCT (SEQ ID NO: 236)

NM_005012 Start position: 2473
CCATATTATGGATTCAGTA (SEQ ID NO: 237)

NM_005012 Start position: 1302
TCCCATGGCAGATCCTATA (SEQ ID NO: 238)

NM_005012 Start position: 1277
CTGCGAACTGTATCCGGAT (SEQ ID NO: 239)

NM_005012 Start position: 2384
AAGCCATCATGTATGGCAA (SEQ ID NO: 240)

NM_005012 Start position: 1260
GCCAGAGAGCCCAGAAGCT (SEQ ID NO: 241)

NM_005012 Start position: 1518
GTGCTTCACCTTGGATGAA (SEQ ID NO: 242)

NM_005012 Start position: 2662
CACACAAGCTCTACTACTC (SEQ ID NO: 243)

NM_005012 Start position: 1013
CCTTCACTATGATTGGCAC (SEQ ID NO: 244)

NM_005012 Start position: 2837
ACCAGCGATTCATTCCCAT (SEQ ID NO: 245)

NM_005012 Start position: 1234
CTGCCAAACTGTGAAGATC (SEQ ID NO: 246)

NM_005012 Start position: 1442
CCGCCCTTCGTTTCCCAGA (SEQ ID NO: 247)

NM_005012 Start position: 891
TGAAGAAGATGGATTCTGT (SEQ ID NO: 248)

NM_005012 Start position: 1960
CAACAAGAAGCCTCCCTAA (SEQ ID NO: 249)

NM_005012 Start position: 2548
TGCCCACCCAGAATGTACA (SEQ ID NO: 250)

NM_005012 Start position: 950
ACCGCACCGTCTATATGGA (SEQ ID NO: 251)

NM_005012 Start position: 2718
CAGTGCCAGCCCAGTGAGT (SEQ ID NO: 252)

NM_005012 Start position: 2487
CAGTAACCAGGAAGTGATT (SEQ ID NO: 253)

NM_005012 Start position: 2225
ACTTCTTTGTCCACAAGGA (SEQ ID NO: 254)

NM_005012 Start position: 3048
TTTACTACCACACATGTCA (SEQ ID NO: 255)

NM_005012 Start position: 2799
CCAGATTGCTGGTTTCATT (SEQ ID NO: 256)

NM_005012 Start position: 3036
AGCAAATATTCCTTTACTA (SEQ ID NO: 257)

NM_005012 Start position: 882
AGATGAGTATGAAGAAGAT (SEQ ID NO: 258)

NM_005012 Start position: 826
ACTGGAGTCTTGTTTGTCA (SEQ ID NO: 259)

NM_005012 Start position: 1669
TTCATTTGCGTCTGTCGGA (SEQ ID NO: 260)

NM_005012 Start position: 2012
TTCTAGGTGCCGTCACTCA (SEQ ID NO: 261)

NM_005012 Start position: 1582
GATTCCAAGGAGAAGAATA (SEQ ID NO: 262)

NM_005012 Start position: 2664
CACAAGCTCTACTACTCCT (SEQ ID NO: 263)

NM_005012 Start position: 1706
CGGCACCAGTCCAGAGGCA (SEQ ID NO: 264)

NM_005012 Start position: 1476
TTCCTACTGCCGCAACCCA (SEQ ID NO: 265)

NM_005012 Start position: 3046
CCTTTACTACCACACATGT (SEQ ID NO: 266)

NM_005012 Start position: 2612
GATTTAAAGATATTCACGT (SEQ ID NO: 267)

NM_005012 Start position: 1612
CTGTACATACTAGTGCCAA (SEQ ID NO: 268)

NM_005012 Start position: 2275
CAACTTCATGTAAAGATTT (SEQ ID NO: 269)

NM_005012 Start position: 1583
ATTCCAAGGAGAAGAATAA (SEQ ID NO: 270)

| | |
|---|---|
| NM_005012 Start position: 2203<br>GGCATGGAATACCTGTCTA | (SEQ ID NO: 271) |
| NM_005012 Start position: 2723<br>CCAGCCCAGTGAGTAATCT | (SEQ ID NO: 272) |
| NM_005012 Start position: 739<br>TCTCGGCTGCGGATTAGAA | (SEQ ID NO: 273) |
| NM_005012 Start position: 1304<br>CCATGGCAGATCCTATAAA | (SEQ ID NO: 274) |
| NM_005012 Start position: 2649<br>GGGACTCTCAAGTCACACA | (SEQ ID NO: 275) |
| NM_005012 Start position: 566<br>CTTACCTGACCCTCGATGA | (SEQ ID NO: 276) |
| NM_005012 Start position: 2856<br>CAATGGATACCCAATACCT | (SEQ ID NO: 277) |
| NM_005012 Start position: 2580<br>GTGCTGGAATGAGATTCCT | (SEQ ID NO: 278) |
| NM_005012 Start position: 1806<br>TCTTTCTGCTGTACGCTTT | (SEQ ID NO: 279) |
| NM_005012 Start position: 2704<br>CAGACAACCTCCCTCAGTG | (SEQ ID NO: 280) |
| NM_005012 Start position: 783<br>CTTCCAGTGCGTGGCAACA | (SEQ ID NO: 281) |
| NM_005012 Start position: 813<br>GGTGGTTTCTTCCACTGGA | (SEQ ID NO: 282) |
| NM_005012 Start position: 2751<br>CAGATATCCTAATTACATG | (SEQ ID NO: 283) |
| NM_005012 Start position: 1463<br>TGAATGGAGGCCATTCCTA | (SEQ ID NO: 284) |
| NM_005012 Start position: 2845<br>TTCATTCCCATCAATGGAT | (SEQ ID NO: 285) |
| NM_005012 Start position: 738<br>CTCTCGGCTGCGGATTAGA | (SEQ ID NO: 286) |
| NM_005012 Start position: 2264<br>TAATCGGAGAGCAACTTCA | (SEQ ID NO: 287) |
| NM_005012 Start position: 876<br>ATACTCAGATGAGTATGAA | (SEQ ID NO: 288) |
| NM_005012 Start position: 2383<br>GAAGCCATCATGTATGCA | (SEQ ID NO: 289) |
| NM_005012 Start position: 3158<br>TAGGAGACGCCAATATTCA | (SEQ ID NO: 290) |
| NM_005012 Start position: 1027<br>GGCACTTCCAGTCACTTAT | (SEQ ID NO: 291) |
| NM_005012 Start position: 1649<br>CCATTGCTTTACTCTTCTT | (SEQ ID NO: 292) |
| NM_005012 Start position: 2810<br>GTTTCATTGGCCCGCCAAT | (SEQ ID NO: 293) |
| NM_005012 Start position: 1337<br>GTTATAACAGCACAGGTGT | (SEQ ID NO: 294) |
| NM_005012 Start position: 736<br>GGCTCTCGGCTGCGGATTA | (SEQ ID NO: 295) |
| NM_005012 Start position: 2605<br>AGACCAAGATTTAAAGATA | (SEQ ID NO: 296) |

(2) siRNA Target Finder Software [Applied Biosystems] ambion.com/techlib/misc/siRNA_finder.html)

The sense strands of siRNAs against human ROR1 (NM_005012: target sequence) are described below.

| | |
|---|---|
| GGGAUCGCGCUCGCGGCAU | (SEQ ID NO: 297) |
| AGAGCUUUGCAGACGUCCC | (SEQ ID NO: 298) |
| GAGCCCGUGGAUGUUCUGC | (SEQ ID NO: 299) |
| UGCACCGGCCGCGCCGCCG | (SEQ ID NO: 300) |
| GAAACAGAGCUGUCAGUCA | (SEQ ID NO: 301) |
| ACAGAGCUGUCAGUCAGUG | (SEQ ID NO: 302) |
| UUAGUGCCUACCUCAUCAU | (SEQ ID NO: 303) |
| CAUCUCAAGUGAACUCAAC | (SEQ ID NO: 304) |
| GUGAACUCAACAAAGAUUC | (SEQ ID NO: 305) |
| CUCAACAAAGAUUCUUACC | (SEQ ID NO: 306) |
| CAAAGAUUCUUACCUGACC | (SEQ ID NO: 307) |
| AGAUUCUUACCUGACCCUC | (SEQ ID NO: 308) |
| CCAAUGAAUAACAUCACCA | (SEQ ID NO: 309) |
| UGAAUAACAUCACCACGUC | (SEQ ID NO: 310) |
| UAACAUCACCACGUCUCUG | (SEQ ID NO: 311) |
| CAUCACCACGUCUCUGGGC | (SEQ ID NO: 312) |
| CUGCACUGCAAAGUCUCUG | (SEQ ID NO: 313) |
| AGUCUCUGGGAAUCCACCU | (SEQ ID NO: 314) |
| UCCACCUCCCACCAUCCGC | (SEQ ID NO: 315) |
| AAAUGAUGCUCCUGUGGUC | (SEQ ID NO: 316) |
| AUGAUGCUCCUGUGGUCCA | (SEQ ID NO: 317) |
| ACCUCGACACCACAGACAC | (SEQ ID NO: 318) |
| CAAACGGCAAGGAGGUGGU | (SEQ ID NO: 319) |
| GGAGGUGGUUUCUUCCACU | (SEQ ID NO: 320) |
| GUUUGGCCCCCUCCCACU | (SEQ ID NO: 321) |
| GUCCAGGAUACUCAGAUGA | (SEQ ID NO: 322) |
| GAAGAUGGAUUCUGUCAGC | (SEQ ID NO: 323) |
| GAUGGAUUCUGUCAGCCAU | (SEQ ID NO: 324) |
| GAUUUAUUGGCAACCGCAC | (SEQ ID NO: 325) |
| CCGCACCGUCUAUAUGGAG | (SEQ ID NO: 326) |
| GGGGAAAUAGAAAAUCAGA | (SEQ ID NO: 327) |
| AUAGAAAAUCAGAUCACAG | (SEQ ID NO: 328) |
| AAUCAGAUCACAGCUGCCU | (SEQ ID NO: 329) |
| UCAGAUCACAGCUGCCUUC | (SEQ ID NO: 330) |
| GUGUUCUCAGUUCGCCAUU | (SEQ ID NO: 331) |
| ACUUCAUCCGUCCCAAAGC | (SEQ ID NO: 332) |
| AGCCCCGUGACUUGUGUCG | (SEQ ID NO: 333) |

-continued

| | |
|---|---|
| UGUGAAAUCCUGGAGAAUG | (SEQ ID NO: 334) |
| AUCCUGGAGAAUGUCCUGU | (SEQ ID NO: 335) |
| UGUCCUGUGUCAAACAGAG | (SEQ ID NO: 336) |
| ACAGAGUACAUUUUUGCAA | (SEQ ID NO: 337) |
| GAUCAAAUCCCAUGAUUCU | (SEQ ID NO: 338) |
| AUCCCAUGAUUCUGAUGAG | (SEQ ID NO: 339) |
| ACUGCCAAACUGUGAAGAU | (SEQ ID NO: 340) |
| ACUGUGAAGAUCUCCCCCA | (SEQ ID NO: 341) |
| GAUCUCCCCCAGCCAGAGA | (SEQ ID NO: 342) |
| GCUGCGAACUGUAUCCGGA | (SEQ ID NO: 343) |
| CUGUAUCCGGAUUGGAAUU | (SEQ ID NO: 344) |
| UUCCCAUGGCAGAUCCUAU | (SEQ ID NO: 345) |
| AUAAAAAUCACAAGUGUUA | (SEQ ID NO: 346) |
| AAAUCACAAGUGUUAUAAC | (SEQ ID NO: 347) |
| AUCACAAGUGUUAUAACAG | (SEQ ID NO: 348) |
| GUGUUAUAACAGCACAGGU | (SEQ ID NO: 349) |
| CAGCACAGGUGUGGACUAC | (SEQ ID NO: 350) |
| AUCAGGGCGCCAGUGCCAG | (SEQ ID NO: 351) |
| UUCCCAGUAUCCCCACACA | (SEQ ID NO: 352) |
| UGGAGGCCAUUCCUACUGC | (SEQ ID NO: 353) |
| CCCAGGGAAUCAAAAGGAA | (SEQ ID NO: 354) |
| UCAAAAGGAAGCUCCCUGG | (SEQ ID NO: 355) |
| AAGGAAGCUCCCUGGUGCU | (SEQ ID NO: 356) |
| GGAAGCUCCCUGGUGCUUC | (SEQ ID NO: 357) |
| GCUCCCUGGUGCUUCACCU | (SEQ ID NO: 358) |
| AACUUUAAGUCUGAUCUGU | (SEQ ID NO: 359) |
| CUUUAAGUCUGAUCUGUGU | (SEQ ID NO: 360) |
| GUCUGAUCUGUGUGACAUC | (SEQ ID NO: 361) |
| AGGAUUCCAAGGAGAAGAA | (SEQ ID NO: 362) |
| GGAGAAGAAUAAAAUGGAA | (SEQ ID NO: 363) |
| GAAUAAAAUGGAAAUCCUG | (SEQ ID NO: 364) |
| UAAAAUGGAAAUCCUGUAC | (SEQ ID NO: 365) |
| AAUGGAAAUCCUGUACAUA | (SEQ ID NO: 366) |
| UGGAAAUCCUGUACAUACU | (SEQ ID NO: 367) |
| AUCCUGUACAUACUAGUGC | (SEQ ID NO: 368) |
| GUGUGGCCAUUCCCCUGGC | (SEQ ID NO: 369) |
| UAACCAGAAGUCAUCGUCG | (SEQ ID NO: 370) |
| CCAGAAGUCAUCGUCGGCA | (SEQ ID NO: 371) |
| GUCAUCGUCGGCACCAGUC | (SEQ ID NO: 372) |
| CCAAAACACGUCAGAGGUC | (SEQ ID NO: 373) |
| AACACGUCAGAGGUCAAAA | (SEQ ID NO: 374) |
| CACGUCAGAGGUCAAAAUG | (SEQ ID NO: 375) |
| AAUGUAGAGAUGUCAAUGC | (SEQ ID NO: 376) |
| UGUAGAGAUGUCAAUGCUG | (SEQ ID NO: 377) |
| UGCUGAAUGCAUAUAAACC | (SEQ ID NO: 378) |
| UGCAUAUAAACCCAAGAGC | (SEQ ID NO: 379) |
| ACCCAAGAGCAAGGCUAAA | (SEQ ID NO: 380) |
| GAGCAAGGCUAAAGAGCUA | (SEQ ID NO: 381) |
| GGCUAAAGAGCUACCUCUU | (SEQ ID NO: 382) |
| AGAGCUACCUCUUUCUGCU | (SEQ ID NO: 383) |
| GAAUUGGGUGAGUGUGCCU | (SEQ ID NO: 384) |
| UUGGGUGAGUGUGCCUUUG | (SEQ ID NO: 385) |
| AAAUCUAUAAAGGCCAUCU | (SEQ ID NO: 386) |
| AUCUAUAAAGGCCAUCUCU | (SEQ ID NO: 387) |
| AGGCCAUCUCUAUCUCCCA | (SEQ ID NO: 388) |
| GACCUUGAAAGACUAUAAC | (SEQ ID NO: 389) |
| AGACUAUAACAACCCCCAG | (SEQ ID NO: 390) |
| CAACCCCCAGCAAUGGACG | (SEQ ID NO: 391) |
| CCCCCAGCAAUGGACGGAA | (SEQ ID NO: 392) |
| UGGACGGAAUUUCAACAAG | (SEQ ID NO: 393) |
| UUUCAACAAGAAGCCUCCC | (SEQ ID NO: 394) |
| CAAGAAGCCUCCCUAAUGG | (SEQ ID NO: 395) |
| GAAGCCUCCCUAAUGGCAG | (SEQ ID NO: 396) |
| GCCUCCCUAAUGGCAGAAC | (SEQ ID NO: 397) |
| UGGCAGAACUGCACCACCC | (SEQ ID NO: 398) |
| CUGCACCACCCCAAUAUUG | (SEQ ID NO: 399) |
| UAUUGUCUGCCUUCUAGGU | (SEQ ID NO: 400) |
| CAACCUGUGUGCAUGCUUU | (SEQ ID NO: 401) |
| CCUGUGUGCAUGCUUUUUG | (SEQ ID NO: 402) |
| UCAGGGGAUCUCCAUGAG | (SEQ ID NO: 403) |
| GAUGGGACUGUGAAAUCCA | (SEQ ID NO: 404) |
| AUCCAGCCUGGACCACGGA | (SEQ ID NO: 405) |
| UUCAGAUUGCAGCUGGCAU | (SEQ ID NO: 406) |
| UACCUGUCUAGUCACUUCU | (SEQ ID NO: 407) |
| GGACCUUGCAGCUCGCAAU | (SEQ ID NO: 408) |
| UAUUUUAAUCGGAGAGCAA | (SEQ ID NO: 409) |
| UCGGAGAGCAACUUCAUGU | (SEQ ID NO: 410) |
| CUUCAUGUAAAGAUUUCAG | (SEQ ID NO: 411) |
| AGAUUUCAGACUUGGGGCU | (SEQ ID NO: 412) |
| AUUUACUCCGCUGAUUACU | (SEQ ID NO: 413) |
| GUCCUUGCUGCCCAUUCGC | (SEQ ID NO: 414) |

-continued

| | |
|---|---|
| GCCAUCAUGUAUGGCAAAU | (SEQ ID NO: 415) |
| AUUCUCUUCUGAUUCAGAU | (SEQ ID NO: 416) |
| CCAGGAAGUGAUUGAGAUG | (SEQ ID NO: 417) |
| GUGAUUGAGAUGGUGAGAA | (SEQ ID NO: 418) |
| AACGGCAGCUCUUACCAUG | (SEQ ID NO: 419) |
| CGGCAGCUCUUACCAUGCU | (SEQ ID NO: 420) |
| GACUGCCCACCCAGAAUGU | (SEQ ID NO: 421) |
| UGUACAGCCUCAUGACAGA | (SEQ ID NO: 422) |
| UGAGAUUCCUUCUAGGAGA | (SEQ ID NO: 423) |
| GAUUUAAAGAUAUUCACGU | (SEQ ID NO: 424) |
| AGAUAUUCACGUCCGGCUU | (SEQ ID NO: 425) |
| GUCACACAAGCUCUACUAC | (SEQ ID NO: 426) |
| GCUCUACUACUCCUUCAGG | (SEQ ID NO: 427) |
| AUGCCACCACACAGACAAC | (SEQ ID NO: 428) |
| CCUCCCUCAGUGCCAGCCC | (SEQ ID NO: 429) |
| UCUCAGUAACCCCAGAUAU | (SEQ ID NO: 430) |
| CCCCAGAUAUCCUAAUUAC | (SEQ ID NO: 431) |
| UUACAUGUUCCCGAGCCAG | (SEQ ID NO: 432) |
| UACCUCAGAACCAGCGAUU | (SEQ ID NO: 433) |
| CCAGCGAUUCAUUCCCAUC | (SEQ ID NO: 434) |
| UGGAUACCCAAUACCUCCU | (SEQ ID NO: 435) |
| UACCUCUGGAUAUGCAGC | (SEQ ID NO: 436) |
| CAGGUCCUCCCAGAGUGAU | (SEQ ID NO: 437) |
| GAGUCGUCCCCAAGCAGU | (SEQ ID NO: 438) |
| GCAGUGCCAGUGGGUCGAC | (SEQ ID NO: 439) |
| UCAGGAAGCAAAUAUUCCU | (SEQ ID NO: 440) |
| GCAAAUAUUCCUUUACUAC | (SEQ ID NO: 441) |
| AUAUUCCUUUACUACCACA | (SEQ ID NO: 442) |
| UUCCAAAUCAUCCUGGUGG | (SEQ ID NO: 443) |
| AUCAUCCUGGUGGAAUGGG | (SEQ ID NO: 444) |
| UGGGUAUCACCGUUUUUGG | (SEQ ID NO: 445) |
| CAAAUCUCAAAAACCCUAC | (SEQ ID NO: 446) |
| AUCUCAAAAACCCUACAAA | (SEQ ID NO: 447) |
| AAACCCUACAAAAUUGACU | (SEQ ID NO: 448) |
| ACCCUACAAAAUUGACUCA | (SEQ ID NO: 449) |
| AAUUGACUCAAAGCAAGCA | (SEQ ID NO: 450) |
| UUGACUCAAAGCAAGCAUC | (SEQ ID NO: 451) |
| AGCAAGCAUCUUUACUAGG | (SEQ ID NO: 452) |
| GCAUCUUUACUAGGAGACG | (SEQ ID NO: 453) |
| UAUUCAUGGACACACCGAA | (SEQ ID NO: 454) |
| UCUAUGAUUUCUGCAGAAC | (SEQ ID NO: 455) |
| CUGUAAAAUGCACAACUUU | (SEQ ID NO: 456) |
| AAUGCACAACUUUUGUAAA | (SEQ ID NO: 457) |
| UGCACAACUUUUGUAAAUG | (SEQ ID NO: 458) |
| CUUUUGUAAAUGUGGUAUA | (SEQ ID NO: 459) |
| AUGUGGUAUACAGGACAAA | (SEQ ID NO: 460) |
| ACUAGACGGCCGUAGAAAA | (SEQ ID NO: 461) |
| AAGAUUUAUAUUCAAAUGU | (SEQ ID NO: 462) |
| GAUUUAUAUUCAAAUGUUU | (SEQ ID NO: 463) |
| AUGUUUUAUUAAAGUAAG | (SEQ ID NO: 464) |
| AGUAAGGUUCUCAUUUAGC | (SEQ ID NO: 465) |
| GGUUCUCAUUUAGCAGACA | (SEQ ID NO: 466) |
| CAAGUACCUUCUGUGAAGU | (SEQ ID NO: 467) |
| GUACCUUCUGUGAAGUUUC | (SEQ ID NO: 468) |
| GUUUCACUGUGUCUUACCA | (SEQ ID NO: 469) |
| GCAGGACAGACACUCGGCC | (SEQ ID NO: 470) |

Example 9

The Expression-Suppressing Effect of Human ROR1 siRNAs in Pulmonary Adenocarcinoma Cells Assessment of Human ROR1 siRNAs for their Expression-Suppressing Effect in Pulmonary Adenocarcinoma Cells ROR1 siRNAs were prepared to perform RNA interference against human ROR1. siROR1-#1 and siROR1-#2 were selected as high-ranking human ROR1 siRNAs from 293 human ROR1 siRNAs identified by RNAi Central (siRNA design) Database [software] (siRNA & shRNA protocol: katahdin.cshl.org:9331/homepage/portal/scripts/main2.pl). siRNA-#1 and siRNA-#2 were thus designed and synthesized by SIGMA GENOSYS Co. Meanwhile, siROR1-#3 (SEQ ID NO: 471) is an HP GenomeWide siRNA purchased from QIAGEN, which was thought to be an siRNA that targets human ROR1. Furthermore, a negative control siRNA (scramble; All Stars Negative Control siRNA) that shows no siRNA effect was also purchased from QIAGEN. Cells of the pulmonary adenocarcinoma cell lines NCI-H358, SK-LC-5, NCI-H1975, and SK-LU-1, and the cervical cancer cell line HeLa, all of which express ROR1, were transfected with an ROR1 siRNA (#1, #2 or #3) or a scramble siRNA at a final concentration of 40 nM using RNAiMAX (invitrogen). 72 hours after transfection, lysates were prepared using SDS sample buffer. At the same time, samples without any treatment (non-transfected) were prepared. After SDS-PAGE, Western blotting was carried out using an anti-ROR1 antibody (Cell Signaling).

Figure 8:
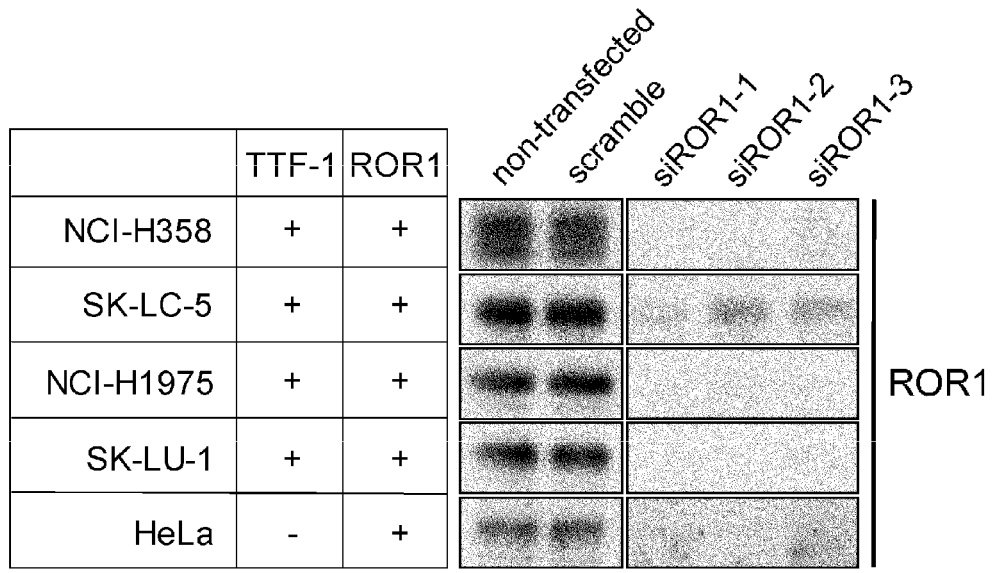
FIG. 8 shows in diagrams and a photograph the expression-suppressing effect of human ROR1 siRNAs in pulmonary adenocarcinoma cells. The ROR1 expression-suppressing effect was assessed using human ROR1 siRNAs (#1, #2, and #3). The result showed that siROR1-#1, siROR1-#2, and siROR1-#3 all decreased the expression of ROR1. The cells used were NCI-H358, SK-LC-5, NCI-H1975, and SK-LU-1 cells, which are derived from pulmonary adenocarcinoma, and HeLa cells which are derived from cervical cancer. All of these cell lines have been found to express ROR1. This finding shows that all three of the ROR1 siRNAs used exhibited an effect of suppressing ROR1 expression. The siRNAs were also demonstrated to specifically suppress the ROR1 expression in the respective cells.

Results and Discussion (FIG. 8)

To assess the expression-suppressing effect of the human ROR1 siRNAs (#1, #2, and #3) at the protein level, ROR1 expression was measured by Western blotting. The result showed that siROR1-#1, siROR1-#2, and siROR1-#3 all reduced ROR1 expression.

Furthermore, it was found that ROR1 expression was not suppressed by a similar treatment with the negative control siRNA (scramble) which shows no siRNA effect.

The cells used in this experiment were NCI-H358, SK-LC-5, NCI-H1975, and SK-LU-1 cells which are derived from pulmonary adenocarcinoma, and HeLa cells which are derived from cervical cancer. ROR1 expression is detected in all of these cell lines (non-transfected).

The above result shows that all of the three ROR1 siRNAs prepared exhibit the ROR1 expression-suppressing effect. It was also demonstrated that the siRNAs specifically suppress ROR1 expression in the cells.

Example 10

Reduction of the Ratio of Viable Pulmonary Adenocarcinoma Cells by Suppression of ROR1 Expression Suppression of ROR1 Expression in Pulmonary Adenocarcinoma Cells (by RNA Interference Using siRNAs) and MTT Assay $1 \times 10^5$ cells of the following cell lines were plated in 6-well dishes: NCI-H358, SK-LC-5, NCI-H1975, and SK-LU-1, which are pulmonary adenocarcinoma cell lines expressing both TTF-1 and ROR1; NCI-H23 and A549, which are pulmonary adenocarcinoma cell lines expressing neither TTF-1 nor ROR1; and the cervical cancer cell line HeLa. The cells were transfected with a scramble siRNA or an ROR1 siRNA (#1, #2 or #3) at a final concentration of 40 nM using RNAiMAX (Invitrogen). At the same time, control groups without any treatment (non-transfected) were prepared. 120 hours after transfection, 1/10 volume of TetraColor ONE was added to the culture medium according to the Cell Proliferation Assay System (Seikagaku Biobusiness Co.). This was incubated at 37° C. for one hour. Then, the absorbance was measured at 450 nm and 630 nm using a spectrophotometer (ARVOmx-fa system; PerkinElmer). The measured values were calculated according to the formula [assay value (450 nm-630 nm)–background (450 nm-630 nm)], and presented in a graph.

Figure 9:
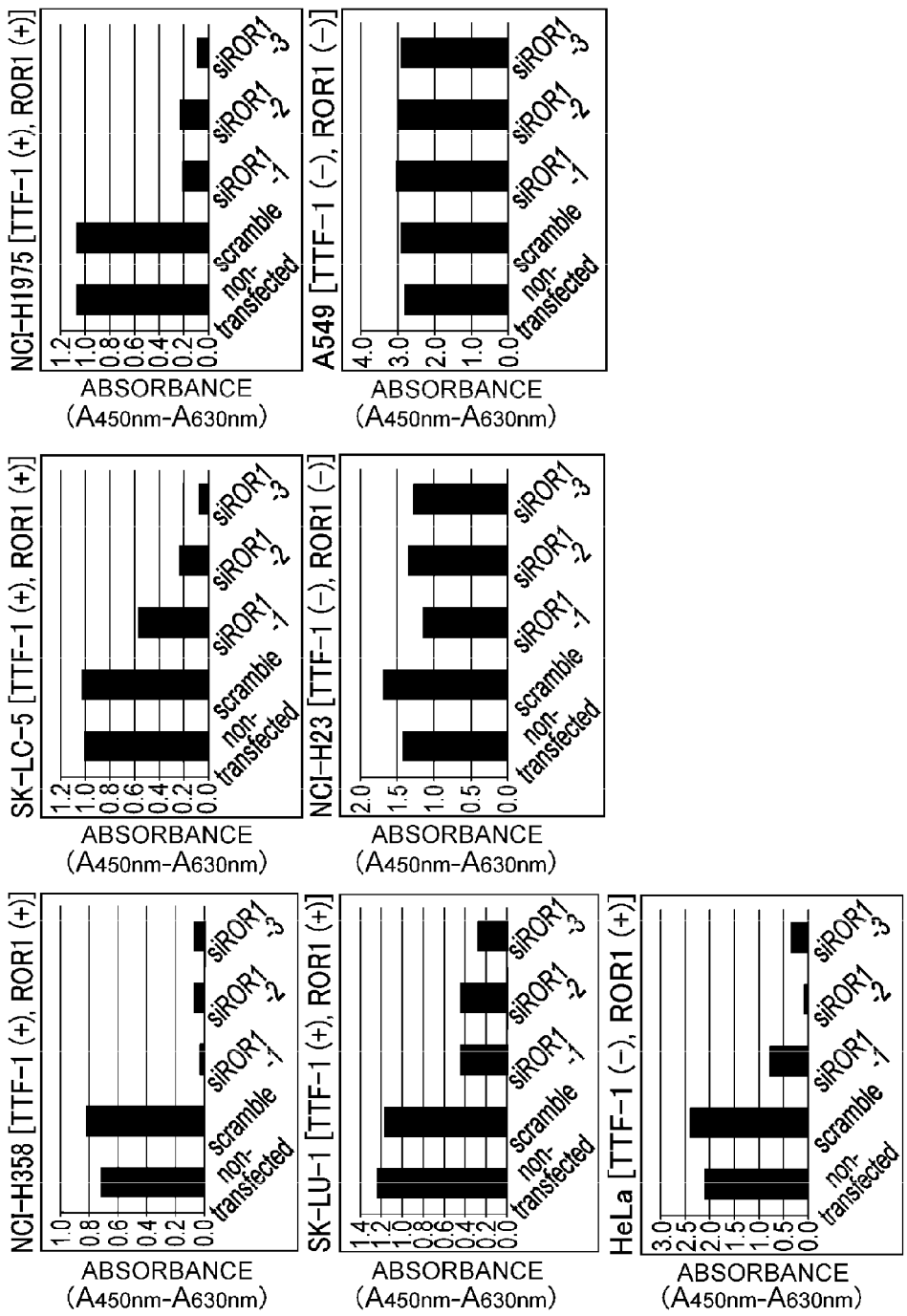
FIG. 9 shows in graphs decrease in the viability of pulmonary adenocarcinoma cells due to suppression of ROR1 expression. Pulmonary adenocarcinoma cells (NCI-H358, SK-LC-5, NCI-H1975, SK-LU-1, NCI-H23, and A549) were transfected with an ROR1 siRNA (#1, #2 or #3). The ratio of viable cells was determined by the MTT method. Each of the ROR1 siRNAs significantly decreased the ratio of viable cells in pulmonary adenocarcinoma lines (NCI-H358, SK-LC-5, NCI-H1975, and SK-LU-1) that express ROR1. By contrast, the ROR1 siRNAs did not affect pulmonary adenocarcinoma lines (NCI-H23 and A549) that do not express ROR1. Furthermore, the same effect was found to be produced in cervical cancer-derived cells (HeLa). The findings described above revealed that ROR1 (is regulated by TTF-1 and) is an essential regulatory factor involved in the survival of pulmonary adenocarcinoma expressing ROR1.

Results and Discussion (FIG. 9)

To assess the ratio of viable pulmonary adenocarcinoma cells after suppression of ROR1 expression, the cells (NCI-H358, SK-LC-5, NCI-H1975, SK-LU-1, NCI-H23, and A549) were transfected with the ROR1 siRNAs (#1, #2, and #3). The ratio of viable cells was determined by the MTT method. The result demonstrated that the ROR1 siRNAs significantly reduced the ratio of viable cells of the pulmonary adenocarcinoma cell lines NCI-H358, SK-LC-5, NCI-H1975, and SK-LU-1 which express ROR1. In contrast, the ROR1 siRNAs had no effect on cells of the pulmonary adenocarcinoma lines NCI-H23 and A549 which do not express ROR1.

"Non-transfected" refers to a control without any treatment, and "scramble" refers to a negative control treated with an siRNA having no siRNA effect. No change was found in the ratio of viable cells in these controls.

Meanwhile, the viability of cervical cancer-derived HeLa cells has been reported to be reduced by an ROR1 siRNA (MacKeigan J P, et al., Nat. Cell Biol. 2005). The ROR1 siRNAs prepared by the present inventors were also demonstrated to exert the same effect.

The above finding revealed that ROR1, which is regulated by TTF-1, is a very important regulatory factor involved in the survival of pulmonary adenocarcinoma expressing ROR1.

Example 11

Reduction of the Number of Viable Pulmonary Adenocarcinoma Cells by Suppressing ROR1 Expression Suppression of ROR1 Expression in Pulmonary Adenocarcinoma Cells (by RNA Interference Using siRNAs) and Determination of the Viable Cell Count $1 \times 10^5$ cells of the following cell lines were plated in 6-well dishes: NCI-H358, SK-LC-5, NCI-H1975, and SK-LU-1, which are pulmonary adenocarcinoma cell lines expressing both TTF-1 and ROR1; NCI-H23 and A549, which are pulmonary adenocarcinoma cell lines expressing neither TTF-1 nor ROR1; and the cervical cancer cell line HeLa. The cells were transfected with a scramble siRNA or an ROR1 siRNA (#1, #2 or #3) at a final concentration of 40 nM using RNAiMAX (Invitrogen). At the same time, a control group without any treatment (non-transfected) was prepared. 120 hours after transfection, the cells were detached by trypsin treatment. The non-transfected, and scramble-, siROR1-1-, siROR1-2-, or siROR1-3-transfected cells were each counted using a cytometer and a counter. The cell counts are presented in a graph.

Figure 10:
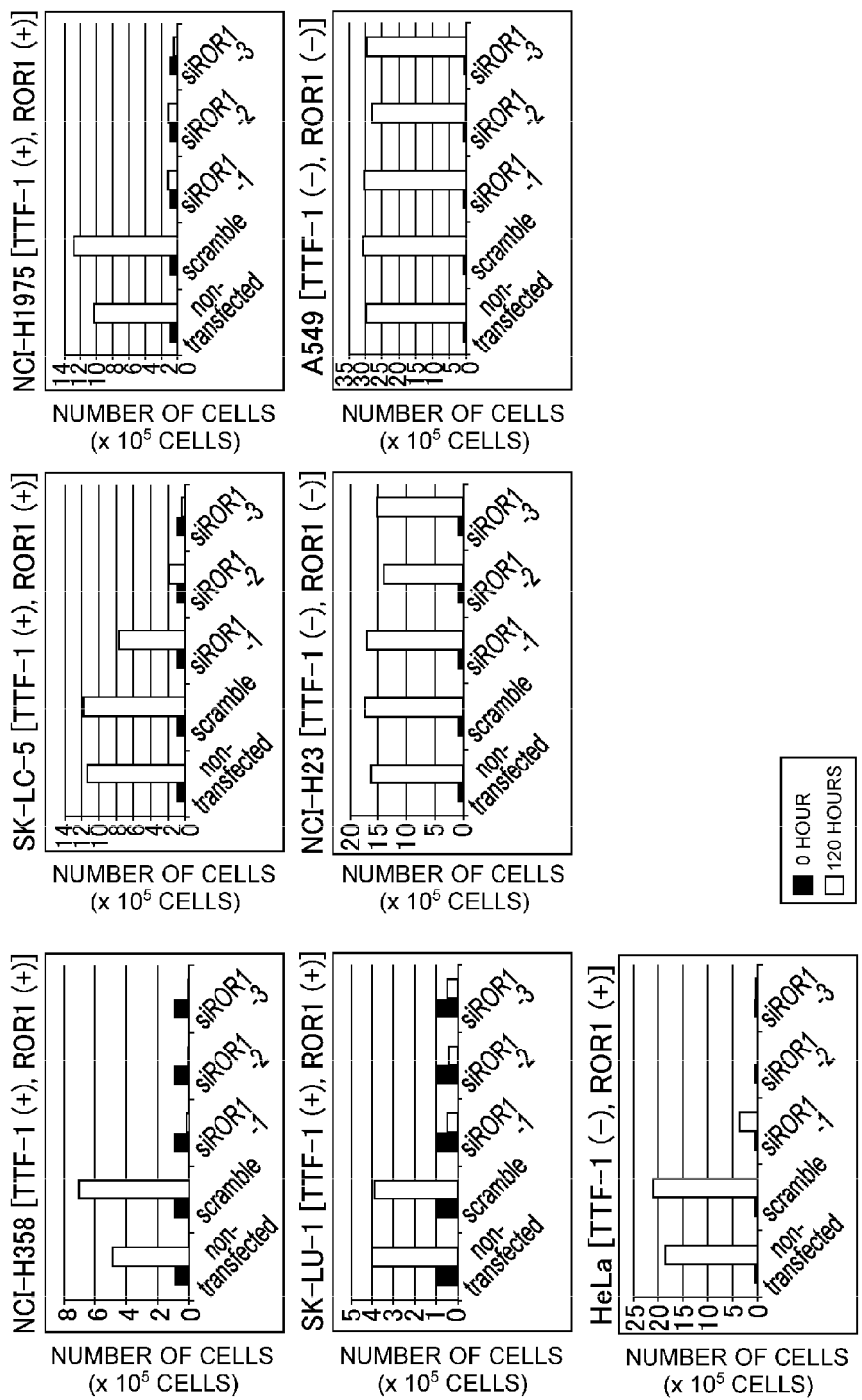
FIG. 10 shows in diagrams decrease in the number of viable pulmonary adenocarcinoma cells due to suppression of ROR1 expression. Each of the cell lines (NCI-H358, SK-LC-5, NCI-H1975, SK-LU-1, NCI-H23, or A549) was transfected with an ROR1 siRNA (#1, #2, or #3) and the number of cells was measured to assess cell count variation. The result showed that each of the ROR1 siRNAs significantly decreased the number of cells in pulmonary adenocarcinoma lines (NCI-H358, SK-LC-5, NCI-H1975, and SK-LU-1) that express ROR1. By contrast, the ROR1 siRNAs did not affect pulmonary adenocarcinoma lines (NCI-H23 and A549) that do not express ROR1. In addition, ROR1 siRNAs also decreased the number of cervical cancer-derived cells (HeLa). The reduction in the number of viable cells also demonstrates that ROR1 is an essential regulatory factor involved in the survival of ROR1-expressing pulmonary adenocarcinoma.

Results and Discussion (FIG. 10)

To determine the number of viable pulmonary adenocarcinoma cells after suppression of ROR1 expression, cells of the NCI-H358, SK-LC-5, NCI-H1975, SK-LU-1, NCI-H23, and A549 cell lines were transfected with the ROR1 siRNAs (#1, #2, and #3), and the cell count was measured. The result of assessing changes in the cell count showed that the ROR1 siRNAs significantly reduced the cell counts of the pulmonary adenocarcinoma lines NCI-H358, SK-LC-5, NCI-H1975, and SK-LU-1 which express ROR1. In contrast, the ROR1 siRNAs had no effect on cells of the pulmonary adenocarcinoma lines NCI-H23 and A549 which do not express ROR1 (the changes in cell count were comparable to those of the non-transfected and scramble-transfected cells).

The ROR1 siRNAs also reduced the number of cells derived from cervical cancer (HeLa).

Together with the result of Example 10, the reduction in the viable cell count demonstrates that ROR1 is a very important regulatory factor involved in the survival of ROR1-expressing pulmonary adenocarcinoma.

Example 12

Reduction of the Percentage of Apoptotic Cells in Pulmonary Adenocarcinoma Cells by Suppression of ROR1 Expression Suppression of ROR1 Expression in Pulmonary Adenocarcinoma Cells (by RNA Interference Using siRNAs) and the TUNEL Method (for Assessing Apoptosis/Cell Death)

$1 \times 10^5$ cells of the following cell lines were plated in 6-well dishes with cover glass: NCI-H358, SK-LC-5, NCI-H1975, and SK-LU-1, which are pulmonary adenocarcinoma cell lines expressing both TTF-1 and ROR1; NCI-H23 and A549, which are pulmonary adenocarcinoma cell lines expressing neither TTF-1 nor ROR1; and the cervical cancer cell line HeLa. The cells were transfected with a scramble siRNA or an ROR1 siRNA (#1, #2 or #3) at a final concentration of 40 nM using RNAiMAX (Invitrogen). At the same time, a control group without any treatment (non-transfected) was prepared. 72 hours after transfection, the culture medium was removed, and the cells were fixed by incubation in 3.7% formalin solution at room temperature for 10 minutes. After washing with PBS, the samples were incubated in 0.1% Triton X-100 solution at room temperature for 10 minutes for permeabilization. After washing with PBS, this was blocked with 1% BSA in PBS solution. Then, the cells were labeled and stained in a TUNEL reaction solution at room temperature for one hour using the In Situ Cell Detection Kit, Fluorescein (Roche Diagnostics). After washing with PBS, PI (Propidium Iodide; SIGMA ALDRICH) which is a nuclear fluorescent dye was dissolved in PBS at a final concentration of 1 μg/ml, and the cells were incubated in this solution at room temperature for 30 minutes to stain the cell nuclei. After washing with PBS, the cells were mounted on glass slides using an immunohistochemical staining reagent, Perma Fluor Aqueous Mounting Medium, (Thermo Shandon) for preparation. Then, this was observed under a confocal laser microscope (μRadiance). The number of stained cells was determined using a counter. The proportion of apoptotic cells was determined and presented in a graph.

Figure 11:
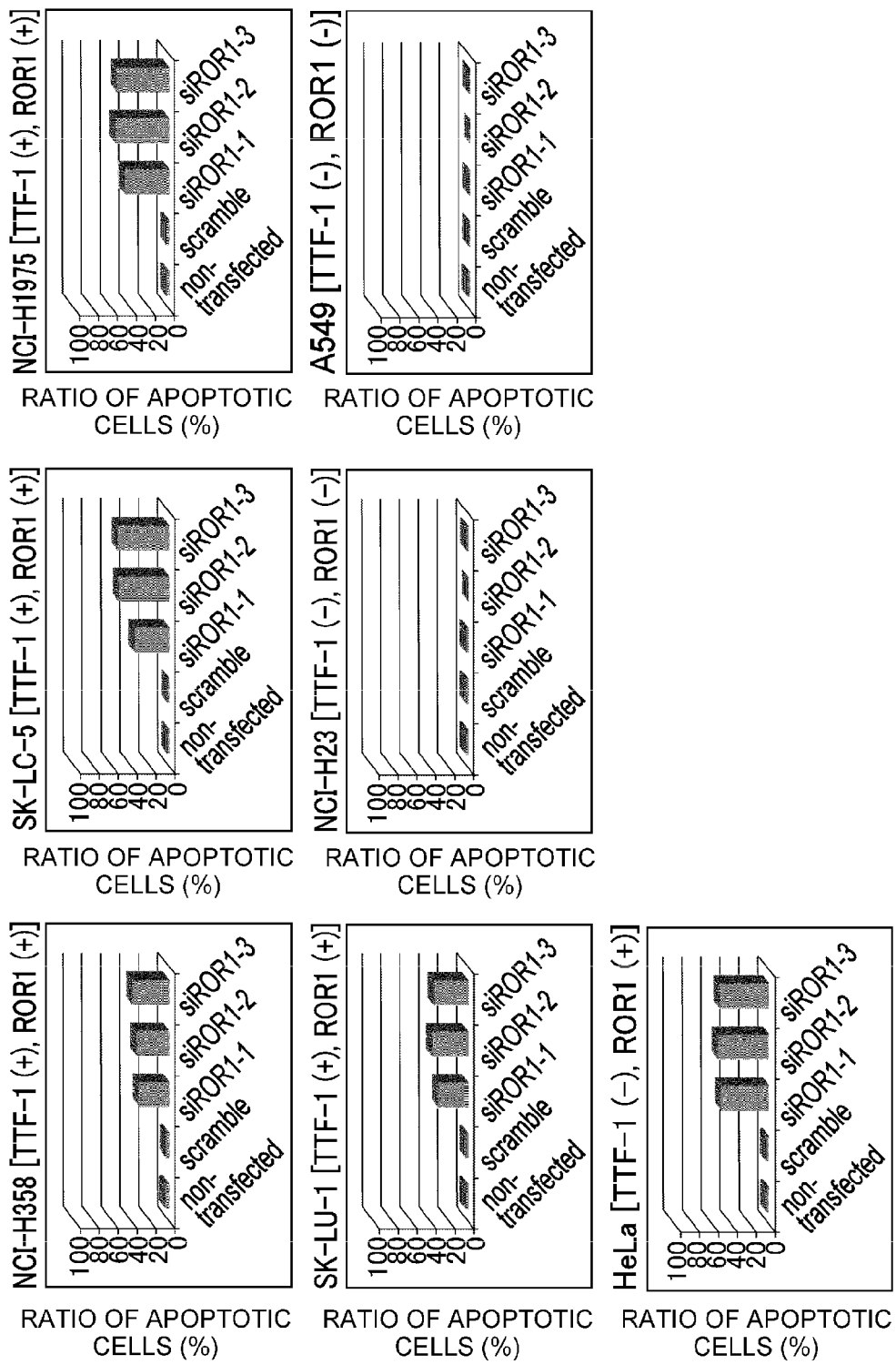
FIG. 11 shows in diagrams increase in the ratio of apoptotic cells in pulmonary adenocarcinoma cells as a result of suppressed ROR1 expression. Each of the cell lines (NCI-H358, SK-LC-5, NCI-H1975, SK-LU-1, NCI-H23, and A549) was transfected with an ROR1 siRNA (#1, #2, or #3). The cell death ratio was determined by counting apoptotic cells with the TUNEL method. The result showed that each of the ROR1 siRNAs significantly increased the number of apoptotic cells and ratio of cell death in pulmonary adenocarcinoma lines that express ROR1 (NCI-H358, SK-LC-5, NCI-H1975, and SK-LU-1). By contrast, the ROR1 siRNAs did not affect the cells of pulmonary adenocarcinoma lines that do not express ROR1 (NCI-H23 and A549). The ROR1 siRNAs also increased the ratio of apoptotic cells in cervical cancer-derived cells (HeLa). The increase in the number of apoptotic cells demonstrates that ROR1 is an essential regulatory factor involved in the survival of ROR1-expressing pulmonary adenocarcinoma.

Results and Discussion (FIG. 11)

Cells of the NCI-H358, SK-LC-5, NCI-H1975, SK-LU-1, NCI-H23, and A549 cell lines were transfected with ROR1 siRNAs (#1, #2, and #3) to determine the proportion of apoptotic cells in pulmonary adenocarcinoma cells after suppression of ROR1 expression. The percentage of cell death was determined by counting apoptotic cells using the TUNEL method. The result showed that the ROR1 siRNAs significantly increased the number of apoptotic cells and the percentage of cell death in the pulmonary adenocarcinoma lines NCI-H358, SK-LC-5, NCI-H1975, and SK-LU-1 which express ROR1. In contrast, the ROR1 siRNAs had no effect on the pulmonary adenocarcinoma lines NCI-H23 and A549 which do not express ROR1 (no apoptosis was induced in the non-transfected or scramble-transfected cells).

The ROR1 siRNAs also increased the proportion of apoptotic cells in cervical cancer-derived cells (HeLa).

Together with the results of Examples 10 and 11, the increase in the number of apoptotic cells demonstrates that ROR1 is a very important regulatory factor involved in the survival of pulmonary adenocarcinoma expressing ROR1.

Example 13

Observation of the Decrease in the Number of Viable Pulmonary Adenocarcinoma Cells after Suppression of ROR1 Expression Suppression of ROR1 Expression in Pulmonary Adenocarcinoma Cells (by RNA Interference Using siRNAs) and Imaging $1\times10^5$ cells of the following cell lines were plated in 6-well dishes: NCI-H358, SK-LC-5, NCI-H1975, and SK-LU-1, which are pulmonary adenocarcinoma cell lines expressing both TTF-1 and ROR1; NCI-H23 and A549, which are pulmonary adenocarcinoma cell lines expressing neither TTF-1 nor ROR1; and the cervical cancer cell line HeLa. The cells were transfected with a scramble siRNA or an ROR1 siRNA (#1, #2 or #3) at a final concentration of 40 nM using RNAiMAX (Invitrogen). At the same time, a control group without any treatment (non-transfected) was prepared. 120 hours after transfection, images of the cells were obtained using an all-in-one digital microscope (Nikon) to observe the conditions of the cells.

Figure 12:
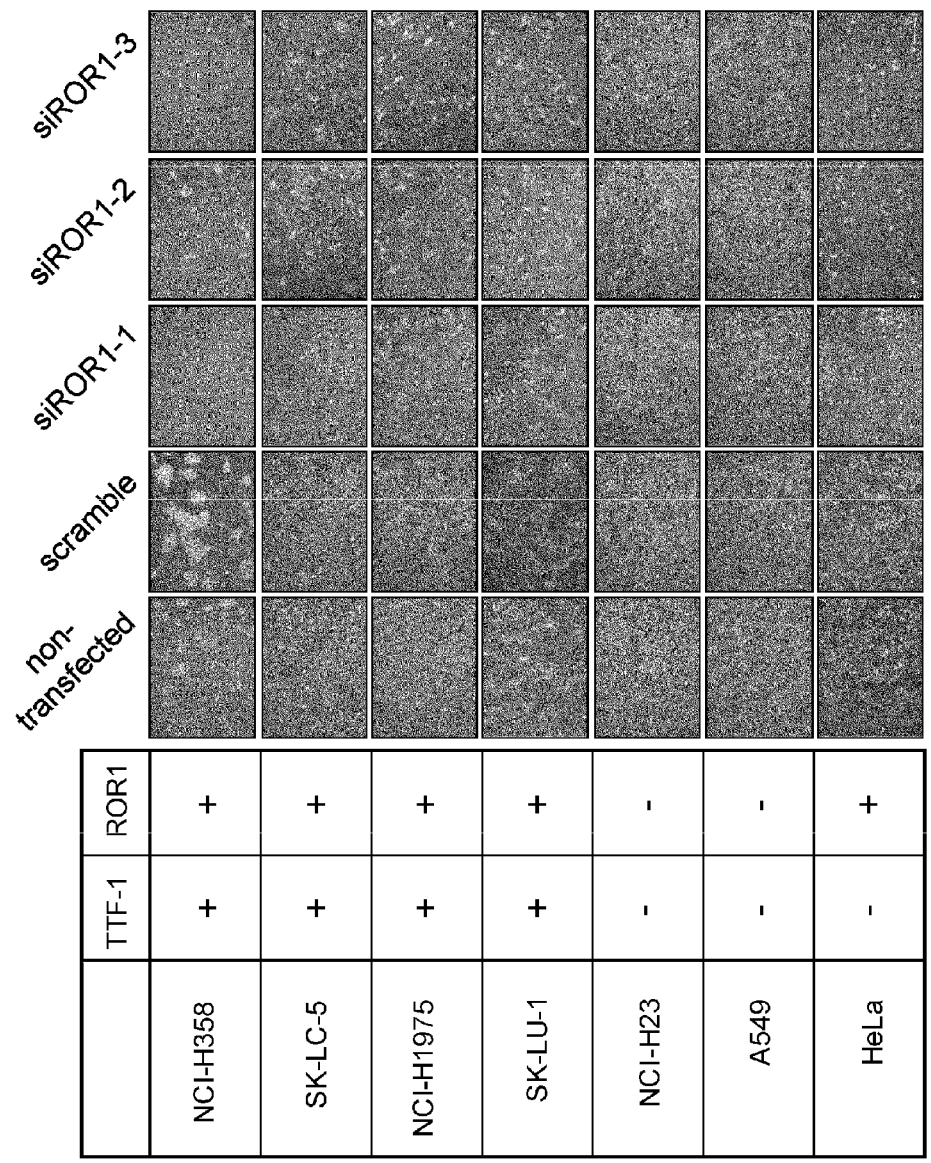
FIG. 12 shows in photographs decrease in the viable pulmonary adenocarcinoma cells as a result of suppressing ROR1 expression. Each of the cell lines NCI-H358, SK-LC-5, NCI-H1975, SK-LU-1, NCI-H23, and A549 was transfected with an ROR1 siRNA (#1, #2, or #3). Then, the states of the cells were observed. The result showed that each of the ROR1 siRNAs significantly decreased the ratio and number of viable cells in the pulmonary adenocarcinoma lines expressing ROR1 (NCI-H358, SK-LC-5, NCI-H1975, and SK-LU-1). Meanwhile, the ROR1 siRNAs did not affect pulmonary adenocarcinoma lines that do not express ROR1 (NCI-H23 and A549). Likewise, the ROR1 siRNAs decreased the ratio and number of viable cells derived from cervical cancer (HeLa). The reduction in the number of viable cells demonstrates that ROR1 is an essential regulatory factor involved in the survival of ROR1-expressing pulmonary adenocarcinoma.

Results and Discussion (FIG. 12)

As with Example 10, to assess the ratio of viable pulmonary adenocarcinoma cells after suppression of ROR1 expression, cells of the NCI-H358, SK-LC-5, NCI-H1975, SK-LU-1, NCI-H23, and A549 cell lines were transfected with an ROR1 siRNA (#1, #2 or #3). Then, the cells were observed to assess their conditions. The result showed that the ROR1 siRNAs significantly reduced the ratio and number of viable cells in the pulmonary adenocarcinoma lines NCI-H358, SK-LC-5, NCI-H1975, and SK-LU-1 which express ROR1, as compared to the non-transfected and scramble-transfected cells.

Meanwhile, the ROR1 siRNAs had no effect on the pulmonary adenocarcinoma lines NCI-H23 and A549 which do not express ROR1. This is similar to the results for the non-transfected and scramble-transfected cells.

The ROR1 siRNAs also reduced the ratio and number of viable cells derived from cervical cancer (HeLa).

Together with Examples 10 to 12, the reduced viable cell count observed demonstrates that ROR1 is a very important regulatory factor involved in the survival of pulmonary adenocarcinoma expressing ROR1.

Example 14

The Expression-Suppressing Effect of the Human ROR1 siRNAs on Various Cancer Cells Assessment of the Human ROR1 siRNAs for the Expression-Suppressing Effect in Various Cancer Cells To perform RNA interference against human ROR1, siROR1-#2 (synthesized by SIGMA GENOSYS co.) which was originally designed herein (by RNAi Central for siRNA design) was used. Furthermore, a negative control siRNA (scramble; All Stars Negative Control siRNA) that shows no siRNA effect was purchased from QIAGEN. The mesothelioma cells NCI-H28, NCI-H2052, and NCI-H2452, and the pancreatic cancer cells MIA PaCa-2 and SW-1990, and the osteosarcoma cells U-2 OS were transfected with ROR1 #2 siRNA or a scramble siRNA at a final concentration of 40 nM using RNAiMAX (Invitrogen). 72 hours after transfection, lysates were prepared using SDS sample buffer. At the same time, samples without any treatment (non-transfected) were prepared. After SDS-PAGE, Western blotting was carried out using an anti-ROR1 antibody (Cell Signaling).

Figure 13:
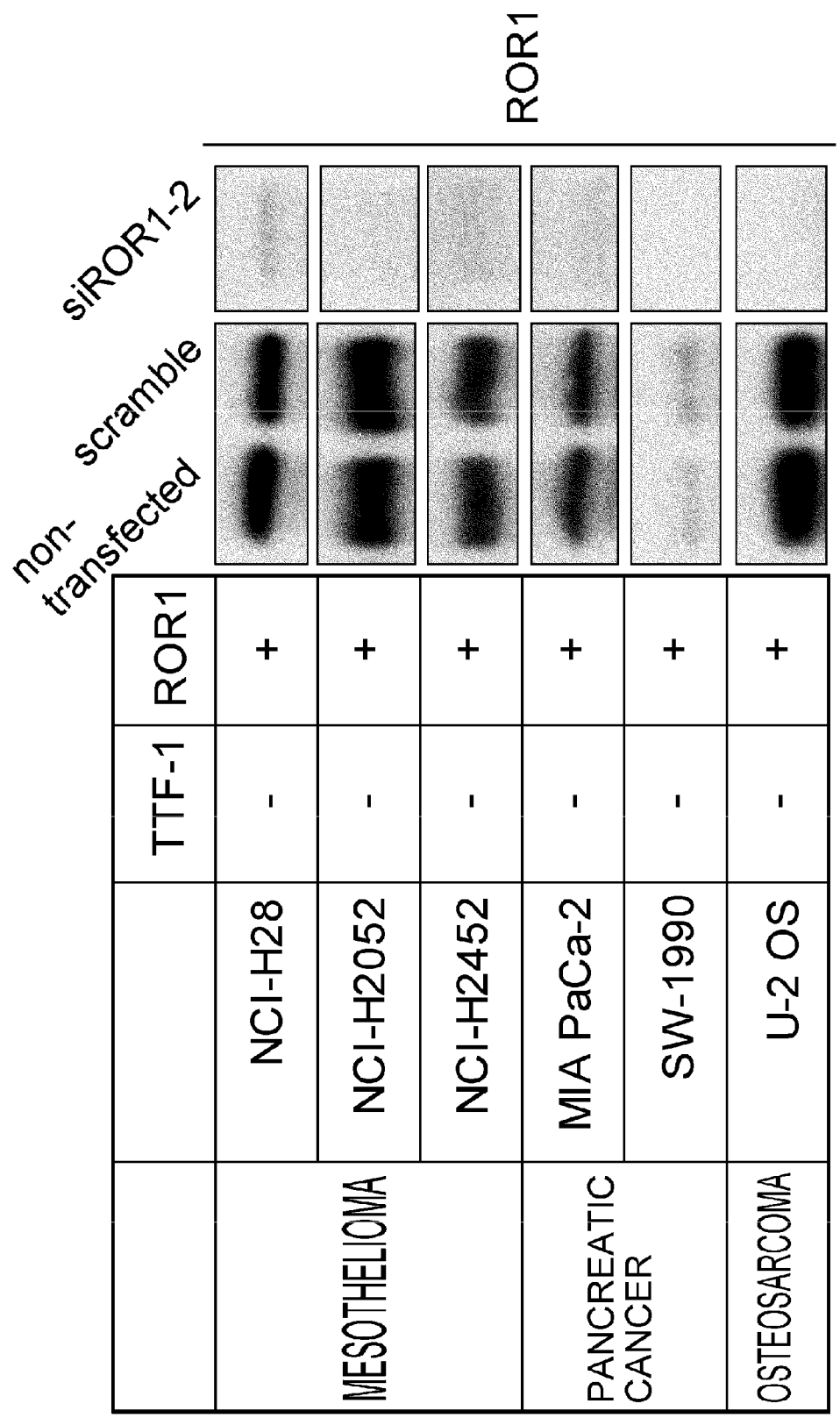
FIG. 13 shows in photographs the expression-suppressing effect of human ROR1 siRNAs in various cancer cell lines. To assess the expression-suppressing effect of human ROR1 siRNA (#2), the expression of ROR1 was examined by Western blotting. The result showed that the siRNA specifically reduced the expression of ROR1 in various cancer-derived cells. The cells used were NCI-H28, NCI-H2052, and NCI-H2452 cells which are derived from mesothelioma, MIA PaCa-2 and SW-1990 which are derived from pancreatic cancer, and U-2 OS which is derived from osteosarcoma. ROR1 expression has been detected in all of these cell lines. The result shows that ROR1 siRNA #2, which was uniquely designed by the present inventors, exhibits the effect of suppressing ROR1 expression. The siRNA was also demonstrated to specifically suppress the expression of ROR1 in various cancer-derived cells.

Results and Discussion (FIG. 13)

To assess the expression-suppressing effect of human ROR1 #2 siRNA at the protein level, ROR1 expression was evaluated by Western blotting. The result showed that ROR1 expression was specifically reduced in various cancer-derived cells.

Furthermore, it was found that ROR1 expression was not suppressed by a similar treatment with the negative control siRNA (scramble) which shows no siRNA effect.

The cells used in this experiment were NCI-H28, NCI-H2052 and NCI-H2452 cells which are derived from mesothelioma, MIA PaCa-2 and SW-1990 cells which are derived from pancreatic cancer, and U-2 OS cells which are derived from osteosarcoma. ROR1 expression is detected in all of these cell lines (non-transfected).

The above result shows that ROR1 #2 siRNA originally designed herein exhibits the effect of suppressing ROR1 expression, and the siRNA specifically suppresses ROR1 expression in various cancer-derived cells.

Example 15

Reduction in the Viable Cell Ratio of Various Cancer Cells by Suppressing ROR1 Expression Suppression of ROR1 Expression in Various Cancer Cells (by RNA Interference Using siRNAs) and MTT Assay 1×10⁵ cells of the following cell lines were plated in 6-well dishes: the NCI-H28, NCI-H2052, and TTFNCI-H2452 mesothelioma cell lines, the MIA PaCa-2 and SW-1990 pancreatic cancer cell lines, and the U-2 OS-1 osteosarcoma cell line, all of which express ROR1. The cells were transfected with a scramble RNA or ROR1 siRNA (siRNA-#2) at a final concentration of 40 nM using RNAiMAX (Invitrogen). At the same time, a control group without any treatment (non-transfected) was prepared. 120 hours after transfection, 1/10 volume of TetraColor ONE was added to the culture medium according to the Cell Proliferation Assay System (Seikagaku Biobusiness Co.). This was incubated at 37° C. for one hour. Then, absorbance was measured at 450 nm and 630 nm using a spectrophotometer (ARVOmx-fa system; PerkinElmer). The measured values were calculated according to the formula: [assay value (450 nm-630 nm)−background (450 nm-630 nm)], and presented in a graph.

Figure 14:
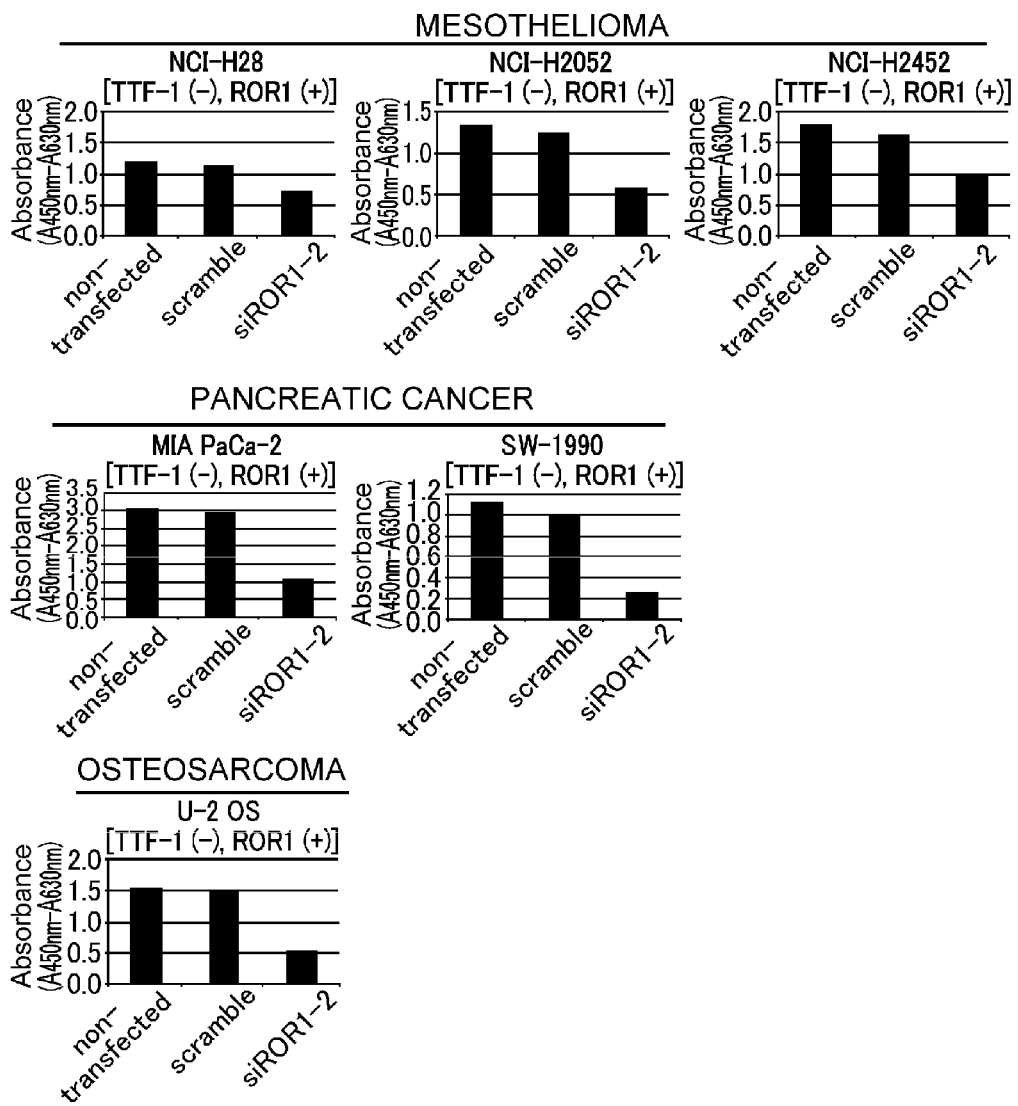
FIG. 14 shows in graphs decrease in the ratio of viable cells of various cancers as a result of suppressing ROR1 expression. Various cancer-derived cells (mesothelioma cells: NCI-H28, NCI-H2052, and NCI-H2452; pancreatic cancer cells: MIA PaCa-2 and SW-1990; and osteosarcoma cells: U-2 OS) were transfected with an ROR1 siRNA (siRNA-#2). The ratio of viable cells was determined by the MTT method. The result showed that the ROR1 siRNA reduced the ratio of viable cells in various cancer-derived cells expressing ROR1. Furthermore, it was demonstrated that the ROR1 siRNA designed by the present inventors in this invention (siROR1-#2) significantly reduce the cell viability. The finding described above revealed that ROR1 expression is an essential regulatory factor involved in the survival of various cancer cells. Suppression of ROR1 expression can be expected to be clinically applicable to a therapeutic method that targets ROR1 in treating lung cancer and osteosarcoma as well as mesothelioma and pancreatic cancer, both of which are extremely difficult to treat. Thus, there is a potential to develop a novel cancer therapy system or the like using an RNA-interference method.

Results and Discussion (FIG. 14)

To assess the viable cell ratio of various cancer-derived cells after suppression of ROR1 expression, cells of the mesothelioma cell lines NCI-H28, NCI-H2052, and NCI-H2452, the pancreatic cancer cell lines MIA PaCa-2 and SW-1990, and the osteosarcoma cell line U-2 OS, were transfected with an ROR1 siRNA (siRNA-#2). The ratio of viable cells was assessed by the MTT method. The result showed that the ROR1 siRNA reduced the viable cell ratio of the cancer-derived cells expressing ROR1. The ROR1 siRNA (siROR1-#2) designed by the present inventors was demonstrated to significantly reduce the ratio of viable cells.

"Non-transfected" refers to a control without any treatment, and "scramble" refers to a negative control treated with an siRNA having no siRNA effect. No change was found in the ratio of viable cells in these controls.

The above finding revealed that ROR1 expression is a very important regulatory factor involved in the survival of various cancer cells. Furthermore, since suppression of ROR1 expression (RNA interference using siRNAs) causes cell death in the cancer-derived cell lines, it can be expected to be clinically applicable to therapeutic methods that target ROR1 against lung cancer and osteosarcoma, as well as mesothelioma and pancreatic cancer which are extremely difficult to treat. Thus, there is a possibility to, for example, develop novel cancer therapy systems that use RNA interference.

Example 16

Reduction of the Survival Signal for Pulmonary Adenocarcinoma Cells by Suppression of ROR1 Expression Effects of Suppression of ROR1 Expression on AKT and p38 Phosphorylation in Pulmonary Adenocarcinoma Cells 1×10⁵ cells of the pulmonary adenocarcinoma line NCI-H1975 expressing ROR1 were plated in 6-well dishes, and they were transfected with a scramble siRNA or ROR1 siRNA (#2) at a final concentration of 40 nM using the transfection reagent RNAiMAX (Invitrogen). 48 hours after transfection, lysates were prepared using SDS sample buffer. After SDS-PAGE, Western blotting (WB) was carried out using an anti-ROR1 antibody (Cell Signaling), anti-phosphorylated AKT (serine 473) antibody (Cell Signaling), anti-AKT antibody (Cell Signaling), anti-phosphorylated p38 (threonine 180 and tyrosine 182) antibody (Cell Signaling), anti-p38 antibody (Cell Signaling), and anti-α-tubulin antibody (SIGMA).

Figure 15:
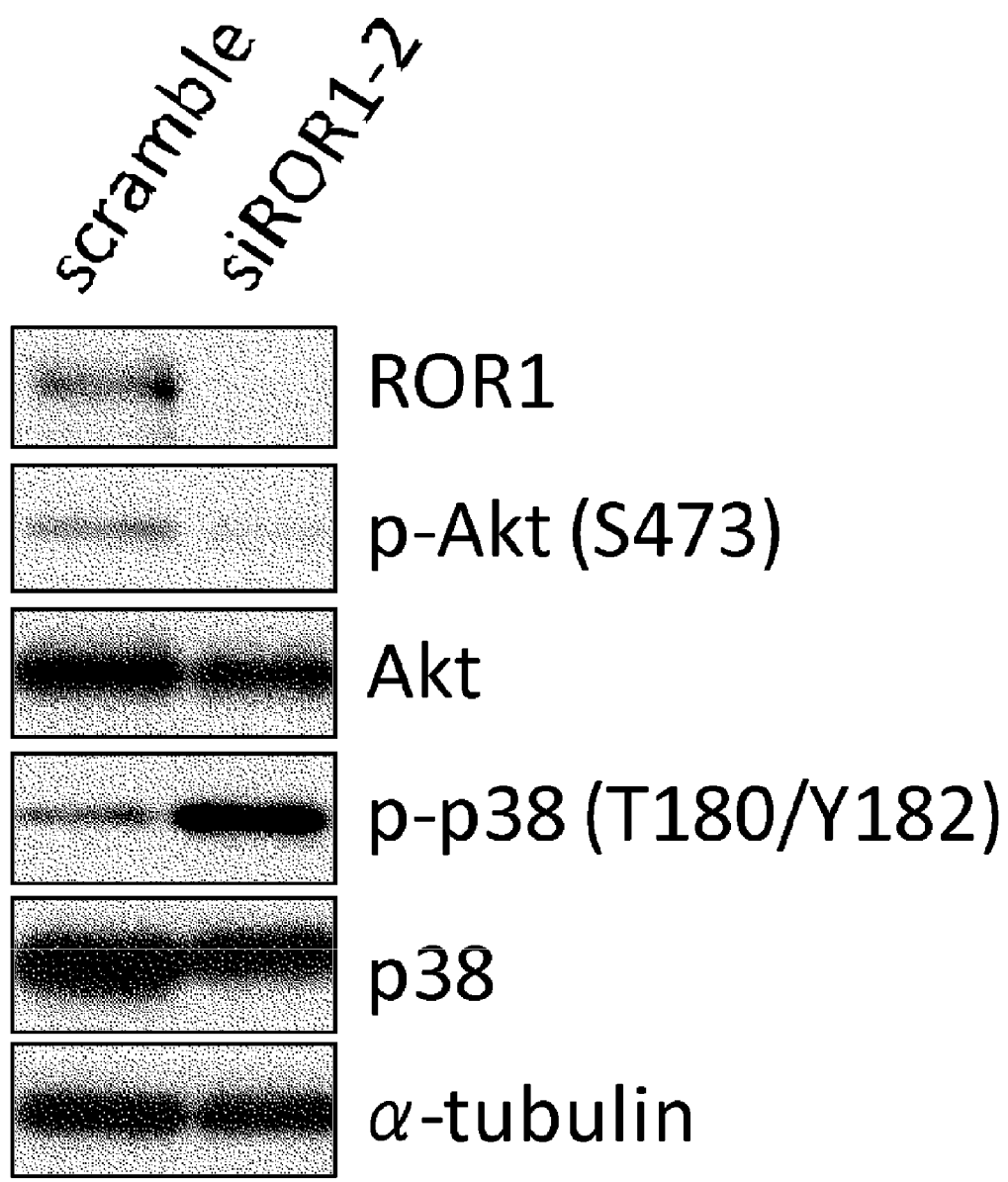
FIG. 15 shows in photographs the effect of suppressing ROR1 expression by an ROR1 siRNA (#2) on the phosphorylation of AKT and p38 in pulmonary adenocarcinoma cells (NCI-H1975). It was demonstrated that the suppression of ROR1 expression in cancer cell lines reduced the phosphorylation level of AKT, which is the most important survival signal for cancer cells, and increased the phosphorylation level of p38, which is an indicator of the most essential apoptotic signal for cell death. This result suggests that nucleic acid compositions (ROR1 siRNAs) are useful as cell growth inhibitors for cancer therapy.

Results and Discussion (FIG. 15)

To assess the effects of suppressing ROR1 expression on AKT and p38 phosphorylation in a pulmonary adenocarcinoma line, ROR1 expression in NCI-H1975 was suppressed. The result showed that AKT phosphorylation (serine 473) was significantly reduced by suppressing ROR1 expression as compared to when the scramble siRNA was used as a control (control group). On the other hand, p38 phosphorylation (threonine 180 and tyrosine 182) was significantly enhanced.

The above result demonstrates that suppressing the ROR1 expression in cancer cell lines reduces AKT phosphorylation which is the most essential survival signal for cancer cells, and also enhances p38 phosphorylation which is the most important indicator of apoptotic signals for cell death. This finding suggests use of the nucleic acid compositions (ROR1 siRNAs) as cell growth inhibitors in therapeutic methods that target cancers.

Example 17

Establishment of Cell Lines Stably Expressing ROR1, and Increase in the Expression of Cancer-Associated Proteins Increased Expression of c-myc, Cyclin D1, and c-jun in Cell Lines Stably Expressing ROR1

Cell lines stably expressing ROR1 were established from the NIH3T3 cell line (a fibroblast cell line derived from mouse embryo) and MSTO line (a cell line derived from human mesothelioma). Neither of the cell lines expresses endogenous TTF-1 or ROR1. The NIH3T3 and MSTO cell lines were forced to express ROR1 (with CMV promoter) or an empty vector (VC) (10-cm dishes). 24 hours after introduction of ROR1 or the empty vector, the cell lines were treated with puromycin for selection (6 μg/ml for NIH3T3; and 1 μg/ml for MSTO). After selection (six days for NIH3T3 and three days for MSTO), cell mass (colony) formation was confirmed for each cell line. Single colonies were individually grown and expanded to establish cell lines stably expressing ROR1. The cell lines shown in the figure are VC#8 and ROR1#24 which are derived from the NIH3T3 cell line, and VC#1, VC#2, ROR1#1, and ROR1#2 which are derived from the MSTO cell line. The mock is the NIH3T3 cell line before transfection. Then, lysates were prepared from the cell lines using SDS sample buffer. After SDS-PAGE, Western blotting (WB) was carried out using an anti-ROR1 antibody (Cell Signaling), anti-c-myc antibody (Santa Cruz), anti-cyclin D1 antibody (BD Bioscience), anti-c-jun antibody (Calbiochem), or anti-α-tubulin antibody (SIGMA).

Figure 16:
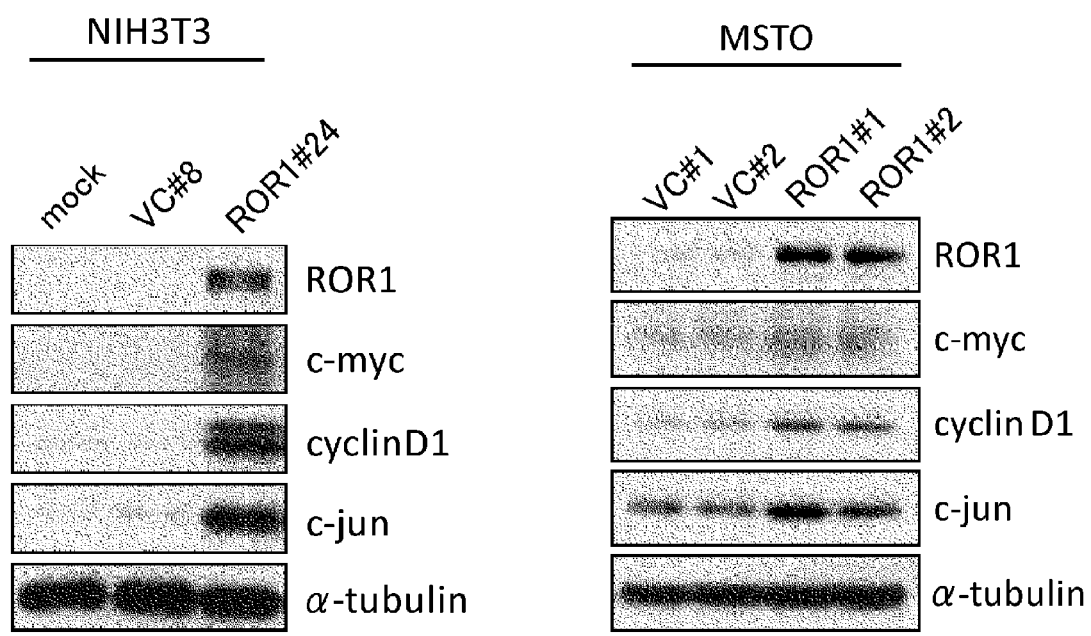
FIG. 16 shows in photographs the establishment of cell lines (NIH3T3 and MSTO cell lines) stably expressing ROR1 and increase in the expression levels of cancer-associated proteins (c-myc, cyclin D1, and c-jun) in the cell lines. Expression of the ROR1 gene was demonstrated to specifically increase the expression levels of c-myc, cyclin D1, and c-jun, which are cancer-associated proteins. This finding suggests that ROR1 specifically expressed in pulmonary adenocarcinoma is a potential oncogene and assumed to regulate c-myc, cyclin D1, and c-jun. Since the present invention targets the ROR1 gene, the above result suggests that targeting ROR1 is useful in cancer therapy.

Results and Discussion (FIG. 16)

Cell lines stably expressing ROR1 were established using the cell lines NIH3T3 and MSTO that express neither TTF-1 nor ROR1. The established cell lines were assessed for the expression of cancer-associated proteins. The result showed that the expressions of c-myc, cyclin D1, and c-jun, which are representative cancer-associated proteins, were increased in an ROR1 expression-specific manner in the two cell lines compared to the vector control (VC) cell lines.

The above result revealed that the ROR1 gene specifically regulates c-myc, cyclin D1, and c-jun which are cancer-associated proteins, and the specific ROR1 expression increases the expression levels of these proteins. Based on this finding, it is thought that ROR1 which is expressed specifically in cancer is highly likely to be an oncogene, and it regulates c-myc, cyclin D1, and c-jun. Since the present invention

Example 18

Reduction of the Expression of Cancer-Associated Proteins in Pulmonary Adenocarcinoma Cells by Suppression of ROR1 Expression Reduction of the Expression of c-myc, Cyclin D1, and c-jun in Pulmonary Adenocarcinoma Cells by Suppression of ROR1 Expression $1\times10^5$ cells of the pulmonary adenocarcinoma cell line NCI-H1975 expressing ROR1 were plated in 6-well dishes, and the cells were transfected with the scramble siRNA or ROR1 siRNA (#2) at a final concentration of 40 nM using the transfection reagent RNAiMAX (Invitrogen). 48 hours after transfection, lysates were prepared using SDS sample buffer. After SDS-PAGE, Western blotting (WB) was carried out using an anti-ROR1 antibody (Cell Signaling), anti-c-myc antibody (SantaCruz), anti-cyclin D1 antibody (BD Bioscience), anti-c-jun antibody (Calbiochem), or anti-α-tubulin antibody (SIGMA).

Figure 17:
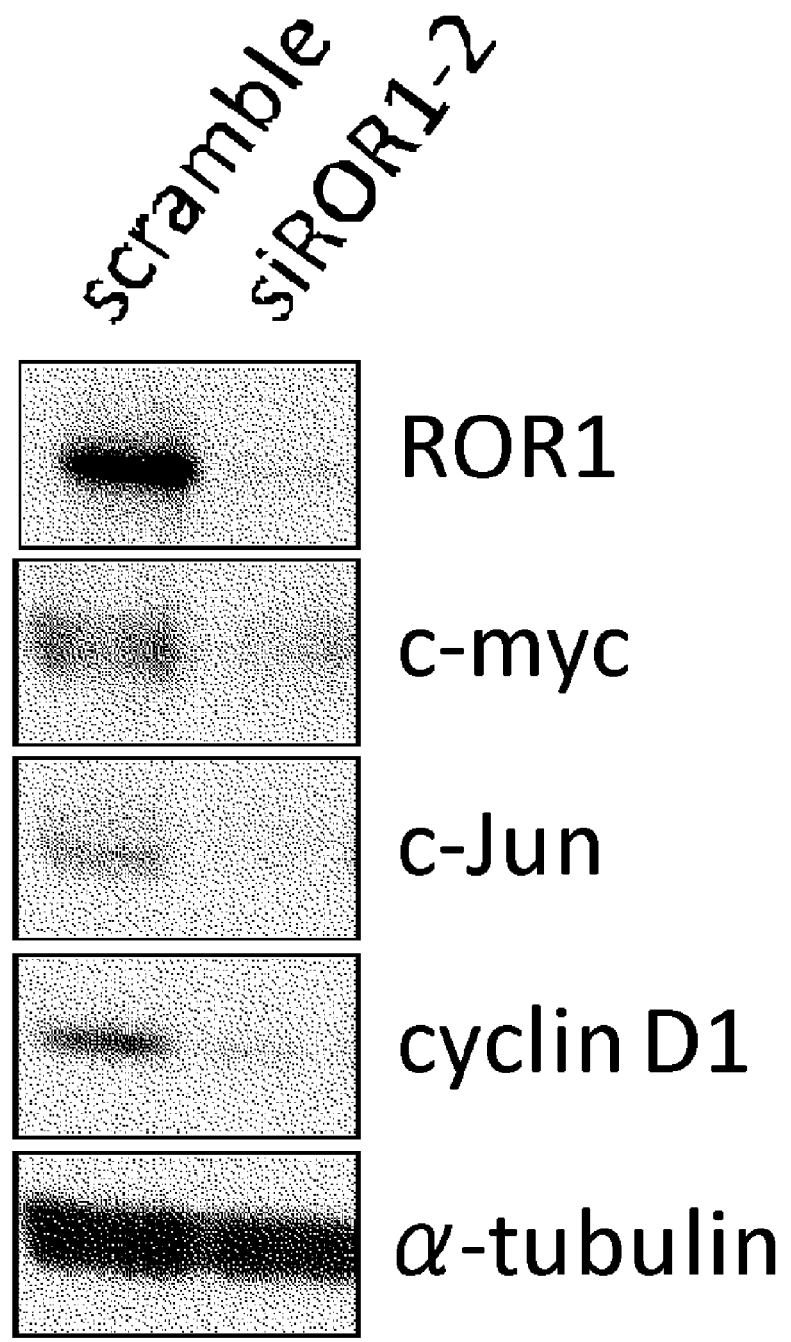
FIG. 17 shows in photographs decrease in the expression of cancer-associated proteins (c-myc, cyclin D1, and c-jun) due to suppression of ROR1 expression by ROR1 siRNA #2 in pulmonary adenocarcinoma cells (NCI-H1975). Suppression of ROR1 expression was revealed to reduce the expression levels of major cancer-associated proteins (c-myc, cyclin D1, and c-jun) in pulmonary adenocarcinoma cells. The result described above demonstrates that ROR1 expression in pulmonary adenocarcinoma cell lines specifically regulates the expression of cancer-associated proteins such as c-myc, cyclin D1, and c-jun. Furthermore, ROR1 siRNA #2 significantly reduced the expression of major cancer-associated proteins (c-myc, cyclin D1, and c-jun) in pulmonary adenocarcinoma cell lines. Thus, the result suggests that nucleic acid compositions (ROR1 siRNAs) of the present invention are useful as cell growth inhibitors for cancer therapy.

Results and Discussion (FIG. 17)

To assess the effects of suppressing ROR1 expression on cancer-associated proteins in a pulmonary adenocarcinoma cell line, ROR1 expression in NCI-H1975 was suppressed. The result showed that the expressions of c-myc, cyclin D1, and c-jun, which are major cancer-associated proteins, were significantly reduced by suppressing ROR1 expression as compared to when the scramble siRNA was used as a control (control group).

The above result demonstrates that ROR1 expression in cancer cell lines specifically regulates the expression of cancer-associated proteins such as c-myc, cyclin D1, and c-jun. This finding supports the result of the experiment using cell lines stably expressing ROR1, as described in Example 17. The ROR1 siRNA (#2) significantly reduced the expression of the major cancer-associated proteins (c-myc, cyclin D1, and c-jun) in cancer cell lines. Thus, this result strongly suggests use of the nucleic acid compositions (ROR1 siRNAs) of the present invention as cell growth inhibitors for therapeutic methods that target cancers.

Example 19

Enhancement of the Cell Growth and Colony Formation Abilities by ROR1 Oncogene Expression Enhancement of the Ability of Cell Growth and Colony Formation from a Small Cell Population of Cell Lines Stably Expressing ROR1

The cancerous property of ROR1 was assessed as its growth ability by colony formation assay and the MTT method (viable cell assay) using the MSTO cell lines stably expressing ROR1 established as described in Example 17. $1\times10^3$ cells of the ROR1 stably expressing MSTO cell lines (VC#1, VC#2, VC#5, ROR1#1, ROR1#2, and ROR1#5) were plated in 10-cm dishes. The time-course changes in the cell count and colony formation ability were assessed by two types of methods. First, on days 0, 11, 18, and 21 after plating the cells, 1/10 volume of TetraColor ONE was added to the culture medium according to the Cell Proliferation Assay System (Seikagaku Biobusiness Co.). This was incubated at 37° C. for one hour. Then, absorbance was measured at 450 nm and 630 nm using a spectrophotometer (ARVOmx-fa system; PerkinElmer). The measured values were calculated according to the formula: [assay value (450 nm-630 nm)−background (450 nm-630 nm)], and presented in a graph using Microsoft Excel. On the other hand, on day 21 after plating the cells, the culture medium was removed completely, and the cells were incubated with a Giemsa staining solution (MERCK) at room temperature for one hour. After washing twice or three times with tap water, the colonies (cell masses) were stained by drying, and assessed for the colony formation ability.

Figure 18:
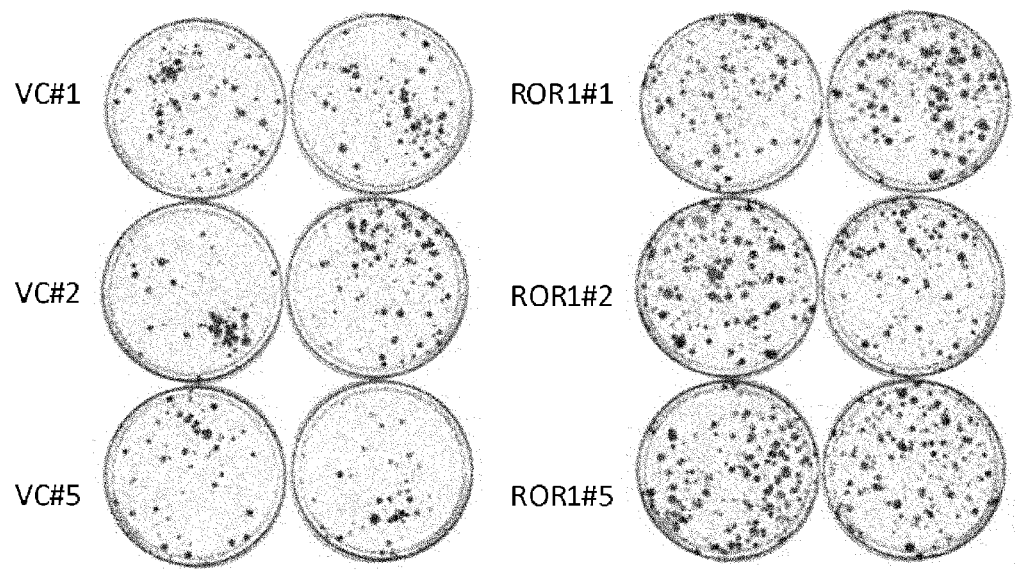
FIG. 18 shows in photographs and a graph enhancement of the abilities of cell growth and colony formation from a small cell population by expressing oncogene ROR1. The growth ability and colony formation ability were assessed using mesothelioma cell lines (MSTO cell lines) stably expressing ROR1. The result demonstrated increase in the number of cells, and enhanced growth and colony formation abilities. This result demonstrated that the ROR1 expression is related to growth ability which is a characteristics of cancer, and the cells acquire the "ability to proliferate from a small population (cell population)". This suggests that it is highly important in cancer therapy to target the ROR1 gene which has the characteristics described above. Thus, the result indicated that nucleic acid compositions (ROR1 siRNA) that target the ROR1 gene are useful for cancer therapy.
Figure 18:
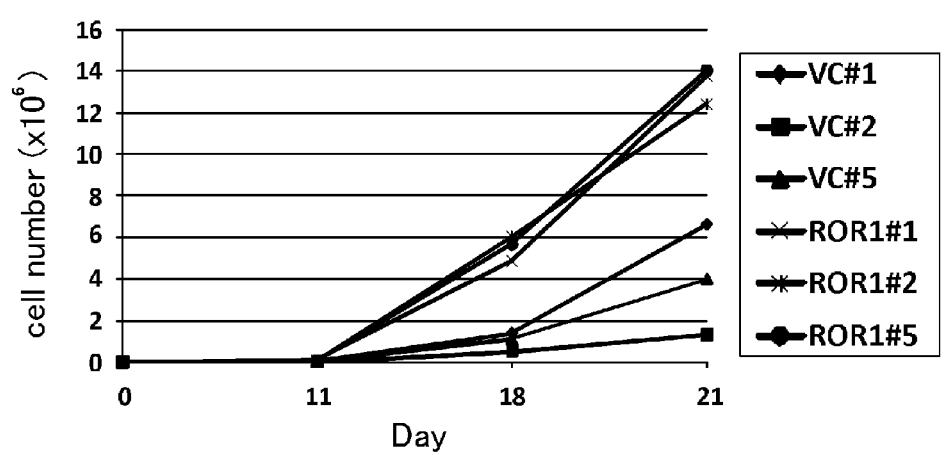

Results and Discussion (FIG. 18)

The growth ability of ROR1 which is a physiological function characteristic of cancer was assessed using the mesothelioma cell lines (MSTO cell lines) stably expressing ROR1. The result showed that starting with a cell count as small as $1\times10^3$ cells at the beginning of the measurement, the cell count was increased and the growth ability was significantly enhanced after 18 and 21 days in the cell lines stably expressing ROR1 (ROR1#1, ROR1#2, and ROR1#5) (about 4.5-fold after 21 days [MTT assay]), as compared to the vector controls (VC#1, VC#2, and VC#5). The result of colony formation assay after 21 days demonstrated that the colony formation ability was significantly increased in the cell lines stably expressing ROR1.

The experiment using the malignant mesothelioma cell lines stably expressing ROR1 revealed that ROR1 expression is involved in the growth ability which is a cancerous property. Furthermore, the cells were demonstrated to acquire the "ability to proliferate from a small cell population", which is thought to be the most important factor in cancer. This indicates that it is highly important to target the ROR1 gene which has the above properties for cancer treatment. Thus, the nucleic acid compositions (ROR1 siRNAs) that target the ROR1 gene are useful for therapeutic methods.

Example 20

Enhancement of the Anchorage-Independent Growth Ability by ROR1 Oncogene Expression Enhancement of the Anchorage-Independent Growth Ability in Cell Lines Stably Expressing ROR1

Using the ROR1 stably expressing MSTO malignant mesothelioma cell lines which were prepared as described in Example 17, the anchorage-independent growth ability of ROR1 was assessed as a cancerous property by soft agar assay. First, to perform soft agar assay, 1% agar solution was prepared by dissolving 1 g of Agar Noble (BD Bioscience) in 100 ml of sterile water. The agar solution was incubated in a 45° C. water bath. 2×RPMI medium (SIGMA) was prepared and combined with the 1% agar solution to obtain a soft agar solution. An appropriate amount of the soft agar solution was added to 6-cm dishes. Cells of the ROR1 stably expressing MSTO cell lines (VC#1, VC#5, ROR1#2, and ROR1#5) were treated with trypsin to disperse into single cells, and then they were plated at $3\times10^4$ cells each. The cells were cultured at 37° C. After two weeks, the cells were incubated with a Giemsa staining solution (MERCK) at room temperature for one whole day and night to stain colonies (cell masses), and the colony number was counted.

Figure 19:
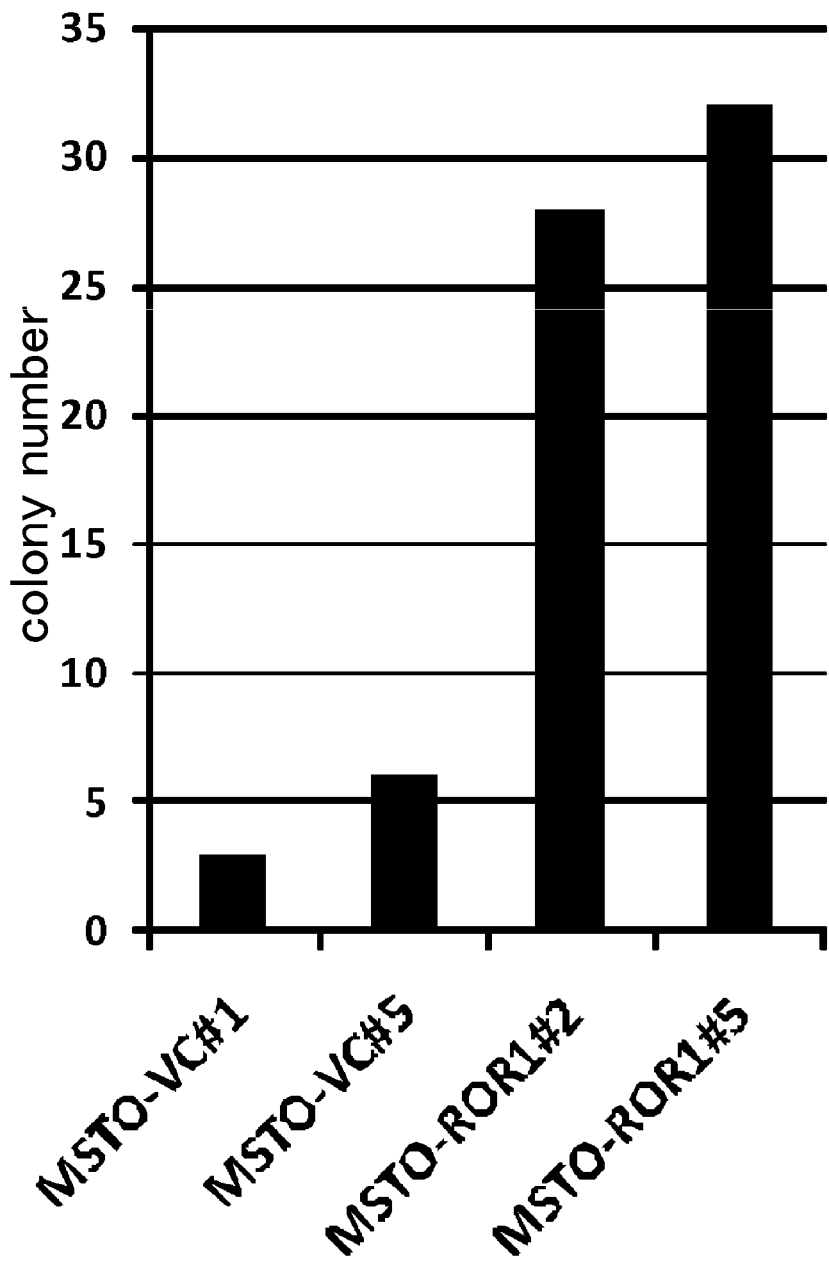
FIG. 19 shows in a graph the enhancement of anchorage-independent growth ability due to expression of oncogene ROR1. Using cell lines (MSTO cell lines) stably expressing ROR1, the anchorage-independent growth ability was assayed. The result showed increased colony counts, i.e., enhanced anchorage-independent growth ability. This result demonstrated that the expression of ROR1 is involved in the anchorage-independent growth ability which is characteristics of cancer. The result described above suggested that it is highly important in cancer therapy to target the ROR1 gene which has the characteristics described above. Thus, the result indicates that nucleic acid compositions (ROR1 siRNA) that target the ROR1 gene are useful for cancer therapy.

Results and Discussion (FIG. 19)

Using the ROR1 stably expressing malignant mesothelioma cell lines (MSTO cell lines), ROR1 was assessed for its anchorage-independent growth ability, which is a physiological function characteristic of cancer. The result showed that after 14 days the colony number of the cell lines stably expressing ROR1 (ROR1#2 and ROR1#5) was significantly increased, i.e., the anchorage-independent growth ability was significantly enhanced (about six-fold), as compared to the vector controls (VC#1 and VC#5).

The experiment using the cell lines stably expressing ROR1 demonstrated that ROR1 expression is involved in the anchorage-independent growth ability which is a cancerous property. As with the results of Example 19, this indicates that targeting the ROR1 gene which has the above characteristics is highly important for cancer treatment, and leads to development of useful therapeutic methods that utilize the nucleic acid compositions (ROR1 siRNAs) targeting the ROR1 gene.

INDUSTRIAL APPLICABILITY

By promoting the functional analysis of oncogenic signaling mediated by the receptor tyrosine kinase ROR1 from the master regulatory factor TTF-1, the essence of oncogenic mechanism can be elucidated based on the new concept. Also, provision of a key to safer cancer therapies that target only cancer cells of a specific lineage is expected, and development of clinical applications of ROR1 in diagnosis and therapy is expected.

The present invention provides cell growth inhibitors comprising nucleic acids that inhibit ROR1 gene expression. Previously, it has not been shown that the ROR1 gene is expressed in various cancer cells. The present inventors demonstrated that the ROR1 gene is expressed ubiquitously in various cancer-derived cell lines, while its expression is almost undetectable in normal cells. Furthermore, the present inventors revealed that ROR1 gene expression is inhibited in various cancer cells by RNA interference.

Thus, the nucleic acids of the present invention which inhibit ROR1 gene expression are applicable to highly safe cancer therapies that target only specific cancer cells.

Since ROR1 which is thought to play an important role in the oncogenic signaling pathway is a receptor tyrosine kinase, it is a starting point of oncogenic signaling and is involved in cancer cell survival. Thus, before ROR1 functions as the receptor, the signals downstream of ROR1 are inhibited by suppressing ROR1 gene expression at the gene level, and this enables ROR1-specific cancer therapies with few side effects.

The invention claimed is:

1. A method for treating or preventing cancer, which comprises the step of administering to a subject having a TTF-1+ ROR1+ cell population a nucleic acid that inhibits ROR1 gene expression.

2. The method of claim 1, wherein the cancer is lung cancer or pulmonary adenocarcinoma.

3. The method of claim 1, wherein the nucleic acid that inhibits ROR1 gene expression is an siRNA, a vector that expresses an siRNA, an antisense RNA, a vector that expresses an antisense RNA, an antisense DNA, a ribozyme, or a vector that expresses a ribozyme.

4. The method of claim 3, wherein the siRNA comprises a sense-strand RNA from any region of an mRNA of the ROR1 gene, and an antisense-strand RNA of the sense-strand RNA.

5. The method of claim 4, wherein a nucleic acid sequence of the sense-strand RNA is selected from the group of sequences consisting of SEQ ID NOs: 4 to 470, and 471.

6. The method of claim 4, wherein a nucleic acid sequence of the sense-strand RNA is selected from the group of sequences consisting of SEQ ID NOs: 5, 6, and 471.

* * * * *

UNITED STATES PATENT AND TRADEMARK OFFICE
CERTIFICATE OF CORRECTION

| | | |
|---|---|---|
| PATENT NO. | : 8,710,022 B2 | |
| APPLICATION NO. | : 13/054288 | |
| DATED | : April 29, 2014 | |
| INVENTOR(S) | : Takahashi et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 316 days.

Signed and Sealed this
Twenty-ninth Day of September, 2015

Michelle K. Lee
*Director of the United States Patent and Trademark Office*